US 10,537,293 B2

(12) United States Patent
Mukumoto et al.

(10) Patent No.: US 10,537,293 B2
(45) Date of Patent: Jan. 21, 2020

(54) X-RAY CT SYSTEM, IMAGE DISPLAY DEVICE, AND IMAGE DISPLAY METHOD

(71) Applicant: Toshiba Medical Systems Corporation, Otawara-shi (JP)

(72) Inventors: Go Mukumoto, Utsunomiya (JP); Katsuhito Morino, Utsunomiya (JP); Atsushi Fukano, Otawara (JP); Takahiro Yoda, Nasushiobara (JP); Masakazu Matsuura, Nasushiobara (JP)

(73) Assignee: Canon Medical Systems Corporation, Otawara-shi (JP)

(*) Notice: Subject to any disclaimer, the term of this patent is extended or adjusted under 35 U.S.C. 154(b) by 179 days.

(21) Appl. No.: 14/119,079

(22) PCT Filed: Jan. 21, 2013

(86) PCT No.: PCT/JP2013/051110
§ 371 (c)(1),
(2) Date: Nov. 20, 2013

(87) PCT Pub. No.: WO2013/125276
PCT Pub. Date: Aug. 29, 2013

(65) Prior Publication Data
US 2014/0093030 A1 Apr. 3, 2014

(30) Foreign Application Priority Data

Feb. 21, 2012 (JP) .................................. 2012-035424
Feb. 22, 2012 (JP) .................................. 2012-036148

(51) Int. Cl.
A61B 6/03 (2006.01)
(52) U.S. Cl.
CPC ..................................... A61B 6/03 (2013.01)

(58) Field of Classification Search
CPC ......... A61B 6/03; A61B 6/032; A61B 6/5205; A61B 6/5211; A61B 6/12; A61B 6/52;
(Continued)

(56) References Cited

U.S. PATENT DOCUMENTS 4,835,688 A       5/1989   Kimura
5,475,803 A *  12/1995   Stearns ..................... G06T 3/00
                                                                    345/648

(Continued)

FOREIGN PATENT DOCUMENTS

CN        1722174 A        1/2006
JP        63 186628        8/1988
(Continued)

OTHER PUBLICATIONS

International Search Report dated Apr. 2, 2013 in PCT/JP13/051110 Filed Jan. 21, 2013.

(Continued)

Primary Examiner — Carolyn A Pehlke
(74) Attorney, Agent, or Firm — Oblon, McClelland, Maier & Neustadt, L.L.P.

(57) ABSTRACT

Techniques are provided that enable displaying of medical images that depict cyclic motions in the subject. An X-ray CT system scans, with X-rays, the subject whose targeted region is experiencing a cyclic motion and acquires detection data. This X-ray CT system comprises a reconstruction processor, a moving image creator, and a display controller. The reconstruction processor generates a plurality of sets of volumetric data based on a plurality of sets of detection data that have been acquired during one cycle of the cyclic motion. The moving-image creator creates a moving image that shows the cyclic motion, on the basis of at least a part of the plural sets of volumetric data. The display controller superposes the moving image over an image based on the (Continued)

volumetric data and displays these images on the display unit.

12 Claims, 26 Drawing Sheets

(58) Field of Classification Search
CPC ... A61B 6/5223; A61B 6/5229; G06T 7/0012; G06Q 50/24; G16H 10/00; G16H 10/60; G16H 30/20; G16H 30/40
USPC ................................ 382/128–132; 600/425
See application file for complete search history.

(56) References Cited

U.S. PATENT DOCUMENTS

| | | | | |
|---|---|---|---|---|
| 5,715,385 | A * | 2/1998 | Stearns | .................... G06T 3/00 345/648 |
| 5,734,384 | A * | 3/1998 | Yanof | .................... G06T 17/10 345/419 |
| 2002/0154801 | A1 * | 10/2002 | Ohishi | .................. G06T 3/0087 382/132 |
| 2004/0021785 | A1 | 2/2004 | Pshtissky et al. | |
| 2004/0087853 | A1 * | 5/2004 | Fujisawa | ................ A61B 6/032 600/425 |
| 2005/0180540 | A1 | 8/2005 | Mukumoto | |
| 2006/0280349 | A1 | 12/2006 | Hildebrand et al. | |
| 2007/0293755 | A1 | 12/2007 | Shirahata et al. | |
| 2012/0076273 | A1 * | 3/2012 | Ida | ....................... A61B 6/4233 378/98 |
| 2013/0058545 | A1 * | 3/2013 | Pearson, Jr. | ........ G06K 9/00221 382/128 |

FOREIGN PATENT DOCUMENTS

| | | | |
|---|---|---|---|
| JP | 2002-125937 | A | 5/2002 |
| JP | 2004 358267 | | 12/2004 |
| JP | 2005 261932 | | 9/2005 |
| JP | 2006 271527 | | 10/2006 |
| JP | 2007-89871 | A | 4/2007 |
| JP | 2007-215806 | A | 8/2007 |
| JP | 2011 081607 | | 4/2011 |
| JP | 2011-217947 | A | 11/2011 |
| JP | 5315524 | B2 * | 10/2013 |
| WO | 2006 033377 | | 3/2006 |

OTHER PUBLICATIONS

Combined Office Action and Search Report dated Feb. 29, 2016 in Chinese Patent Application No. 201380002811.9.
Office Action dated Jan. 5, 2016 in Japanese Patent Application No. 2012-035424.
Office Action dated Nov. 21, 2017, in the corresponding Japanese Patent Application No. 2016-223506.

* cited by examiner

X-RAY CT SYSTEM, IMAGE DISPLAY DEVICE, AND IMAGE DISPLAY METHOD

TECHNICAL FIELD

Embodiments of the present invention relate to X-ray CT systems, image display devices and image display methods.

BACKGROUND ART

X-ray CT (Computed Tomography) systems are a type of equipment that provides imaging of the interior of a subject by scanning the subject with X-ray equipment for data acquisition and then by processing the data with a computer.

Specifically, an X-ray CT system irradiates the subject with X-rays multiple times in different directions, detects the X-rays that have passed through the subject with an X-ray detector, and acquires multiple sets of detection data. The detection data gathered are A/D converted by a data acquisition system and then transmitted to a console device. The console device performs preprocessing on the detection data and thereby generates projection data. Then, the console device executes reconstruction-processing on the projection data and generates volumetric data based on a set of tomographic data or a plurality of sets of tomographic data. Volumetric data are a data set representing a three-dimensional distribution of CT values that corresponds to a three-dimensional area in the subject.

The X-ray CT system can display an image in an MPR (Multi-Planar Reconstruction) view by rendering the volumetric data in a given direction. In the following descriptions, the sectional images that are MPR views achieved by rendering the volumetric data are also referred to as "MPR images". MPR images are, for example, axial images, which are sections slicing the subject at a right angle to the axis of the body, sagittal images, which are sections slicing the subject vertically along the body axis, and coronal images, which are sections slicing the subject horizontally along the body axis, (these three types are sometimes collectively referred to as "three-orthogonal-axis images"). Furthermore, MPR images include views in arbitrary sectional planes passing through the volumetric data (oblique images) and curved MPR images. Curved MPR images are views in curved sectional planes, for example, sectional views along the coronary arteries of the heart, and along the jawbone or the dentition. A plurality of MPR images created in such conditions can be displayed simultaneously on a display unit, etc.

There is a scanning method called CT fluoroscopy (CTF: Computed Tomography Fluoroscopy), which is performed using an X-ray CT system. CT fluoroscopy is a method of scanning in which X-rays are continually radiated on the subject to acquire real-time images of a region of interest in the subject. In CT fluoroscopy, the rate of detection data gathering is set low to shorten the time required for reconstruction-processing, so that images are displayed in real time. CT fluoroscopy is applied to monitoring, for example, positional relations between the leading end of the puncture needle and the site where a tissue sample is to be collected during biopsy or to monitoring the position of the tube in draining methods. By the way, draining methods are a type of procedure for draining, with a tube, bodily fluids that have accumulated in body cavities.

In a case where a biopsy is performed on the subject while MPR images based on the volumetric data acquired by CT fluoroscopy are being referred to, for example, scanning and puncturing are executed repeatedly one after the other. Specifically, at first, an MPR image of the subject is acquired by CT fluoroscopy, and a doctor or the like performs puncturing while the MPR image is being referred to. In the puncturing procedure, when puncturing has been executed to a certain extent, CT fluoroscopy is performed again, for example, to check the positional relation between the leading end of the puncture needle and the site where a tissue sample is to be collected. The doctor or the like proceeds with the puncturing further by referring to the MPR image created on the basis of this newly performed CT fluoroscopy. These actions are repeated until the biopsy is completed, for ensuring accurate biopsy.

PRIOR ART REFERENCES

Patent References

[Patent Reference 1] Japanese Laid-Open Patent Publication No. 2005-261932

[Patent Reference 2] Japanese Laid-Open Patent Publication No. 2004-358267

SUMMARY OF THE INVENTION

Problems to be Solved by the Invention

Organs (e.g., the lungs) and lesion sites in the subject are experiencing cyclic motions under the influence of the respiration and the heartbeat. Accordingly, in a case where a biopsy is performed on the subject with reference to an MPR image, there can be a positional deviation of the site where a tissue sample is to be collected. The site, which is shown in the MPR image, can deviate between a position at the timing when the volumetric data on which the MPR image is based are acquired and a position at the timing when the puncturing is actually being executed. However, it was difficult to identify such deviation (cyclic motion) in MPR images.

Embodiments herein have been invented to solve the above-described problem, and their objective is to provide techniques that enable the displaying of medical images that depict cyclic motions in the subject.

Means for Solving the Problems

An X-ray CT system presented as an embodiment is an X-ray CT system that scans, with X-rays, the subject whose targeted region is experiencing a cyclic motion and acquires detection data. This X-ray CT system comprises a reconstruction processor, a moving image creator, and a display controller. The reconstruction processor generates a plurality of sets of volumetric data based on a plurality of sets of detection data that have been acquired during one cycle of the cyclic motion. The moving-image creator creates a moving image that shows the cyclic motion, on the basis of at least a part of the plural sets of volumetric data. The display controller superposes the moving image over an image based on the volumetric data and displays these images on the display unit.

Another X-ray CT system presented as an embodiment is an X-ray CT system that scans, with X-rays, the subject whose targeted region is experiencing a cyclic motion and acquires detection data. This X-ray CT system comprises a reconstruction processor, a trace-image creator, and a display controller. The reconstruction processor generates a plurality of sets of volumetric data based on a plurality of sets of detection data that have been acquired during one cycle of the cyclic motion. The trace-image creator creates a trace image that shows a trace of the cyclic motion, on the basis of at least a part of the plural sets of volumetric data. The display controller superposes the trace image over an image based on the volumetric data and displays these images on the display unit.

PREFERRED EMBODIMENTS OF THE INVENTION (First Embodiment)

Now, the configuration of an X-ray CT system 1 as a first embodiment is explained with reference to FIG. 1 through FIG. 3. By the way, since the terms "image" and "image data" correspond to each other one-on-one, they may be used as identical terms for the present embodiment. Also, the term "three-dimensional image (three-dimensional moving-image)" in this embodiment includes so-called "pseudo-three-dimensional images", which are three-dimensional image data displayed in two dimensions.

<System Configuration>

Figure 1:
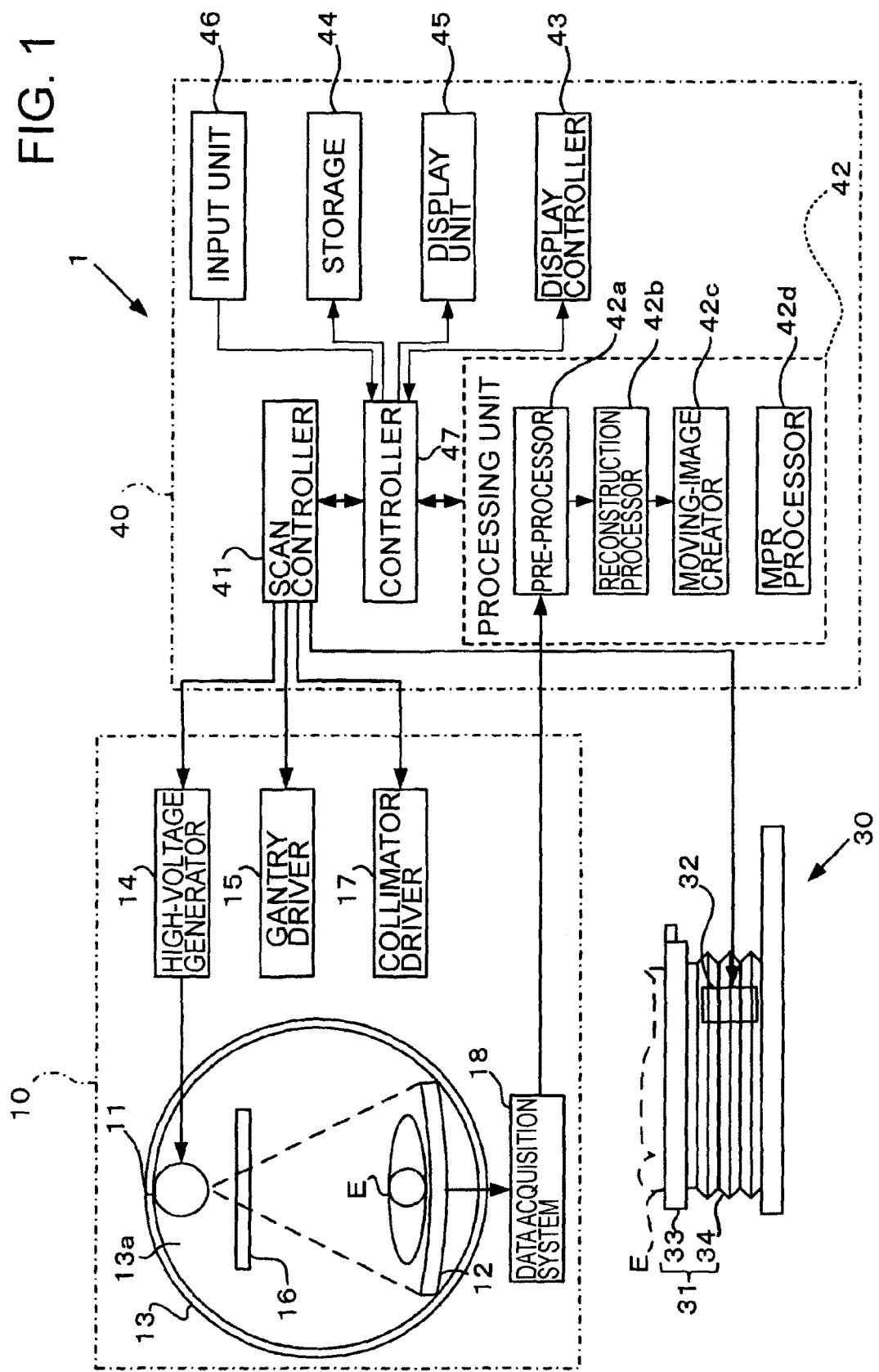
FIG. 1 is a block diagram showing an X-ray CT system as a first embodiment.

The X-ray CT system 1 is configured to include a gantry apparatus 10, a patient table 30, and a console device 40 as shown in FIG. 1.

[Gantry Apparatus]

The gantry apparatus 10 is a piece of equipment that irradiates a subject E with X-rays and gathers data detected of X-rays that have passed through the subject E. The gantry apparatus 10 comprises an X-ray generator 11, an X-ray detector 12, a rotating body 13, a high voltage generator 14, a gantry drive 15, a collimator 16, a collimator drive 17, and a data acquisition system 18.

The X-ray generator 11 is configured to include an X-ray tube, which generates X-rays (e.g., a vacuum tube that generates beams in circular cone or pyramid-shape, not shown). X-rays being generated are used for irradiating the subject E. The X-ray detector 12 is configured to include a plurality of X-ray detector elements (not shown). The X-ray detector 12 detects, with its X-ray detector elements, X-ray intensity distribution data (hereinafter also referred to as "detection data"), which show an intensity distribution of the X-rays that have passed through the subject E, and then outputs detection data in current signals. The X-ray detector 12 comprises a two-dimensional X-ray detector (area detector) in which, for example, a plurality of detector elements are disposed respectively in two inter-orthogonal directions (slicing direction and channeling direction). A plurality of X-ray detector elements are aligned, for example, in 320 lines in slicing direction. The use of an X-ray detector having such a multi-line configuration enables the scanning of a three-dimensional region, which has a width in slicing direction, per scanning rotation (volumetric scanning). By the way, the slicing direction corresponds to the rostrocaudal direction of the subject E while the channeling direction corresponds to the rotational direction of the X-ray generator 11.

The rotating body 13 is a member that supports both the X-ray generator 11 and the X-ray detector 12 facing each other with the subject E in position between them. The rotating body 13 has a through-opening 13a in the slicing direction and is disposed in the gantry apparatus 10, so that the rotating body 13 rotates around the subject E as its center in a circular orbit.

The high voltage generator 14 supplies high voltage to the X-ray generator 11, and the X-ray generator 11 generates X-rays on the high voltage. The gantry drive 15 drives the rotating body 13 to rotate. The collimator 16 has a slit (opening) with a predetermined width, which is changed to adjust the fan angle (flare angle in the channeling direction) and the cone angle (flare angle in the slicing direction) of the X-rays that have been generated and radiated by the X-ray generator 11. The collimator drive 17 drives the collimator 16 so that the X-rays generated by the X-ray generator 11 are formed in a predetermined shape.

The data acquisition system 18 (DAS) gathers detection data from the X-ray detector 12 (from each of the X-ray detector elements). Furthermore, the data acquisition system 18 converts the detection data gathered (in current signals) into voltage signals, integrates them periodically for amplification, and then converts them into digital signals. Then, the data acquisition system 18 sends the detection data that have been converted into digital signals to the console device 40 (including a processor unit 42, which is described later). By the way, in CT fluoroscopy, after the detection data have been gathered by the data acquisition system 18, it is desirable to acquire CT images in real time by executing reconstruction-processing within a very short period of time with a reconstruction processor 42b (described later). Accordingly, the rate of detection data gathering by the data acquisition system 18 is set low.

[Patient Table]

The patient table 30 is a device that is used for mounting the subject E and moving the subject for scanning. The patient table 30 comprises a bed 31 and a bed drive 32. The bed 31 comprises a couch top 33, on which the subject E is placed, and a pedestal 34, which supports the couch top 33. The couch top 33 is driven by the bed drive 32 and movable in the rostrocaudal direction of the subject E and in a direction perpendicular to the rostrocaudal direction. In other words, the bed drive 32 drives the couch top 33, which is mounted with the subject E, into and out of the opening 13a of the rotating body 13. The pedestal 34 is driven by the bed drive 32 for moving the couch top 33 in the up and down direction (i.e., in a direction perpendicular to the rostrocaudal direction of the subject E).

[Console Device]

The console device 40 is used for operational inputs to the X-ray CT system 1. In addition, the console device 40 has, for example, the function of reconstructing CT image data (tomographic data and volumetric data), which show internal structures in the subject E, on the basis of the detection data gathered by the gantry apparatus 10. The console device 40 is configured to include a scanning-control unit 41, a processing unit 42, a display controller 43, a storage 44, a display unit 45, an input unit 46, and a control unit 47.

The scanning-control unit 41 controls various actions involved in scanning with X-rays. For example, the scanning-control unit 41 controls the high voltage generator 14 to apply high voltage onto the X-ray generator 11, controls the gantry drive 15 to rotationally drive the rotating body 13, controls the collimator drive 17 to adjust the collimator 16, and controls the bed drive 32 to move the bed 31.

The processing unit 42 executes various types of processing on the detection data, which have been received from the gantry apparatus 10 (data acquisition system 18). The processing unit 42 is configured to include a preprocessor 42a, a reconstruction processor 42b, a moving-image creator 42c, and an MPR processor 42d.

The preprocessor 42a executes such preprocessing as logarithmic transformation, offset correction, sensitivity correction, and beam hardening correction on the detection data, which have been detected by the gantry apparatus 10 (X-ray detector 12), and by doing so, the preprocessor generates projection data.

The reconstruction processor 42b generates CT image data (tomographic data and volumetric data) on the basis of the projection data (detection data), which have been prepared by the preprocessor 42a. For tomographic data reconstruction, such methods as two-dimensional Fourier transformation and convolution back projection can be employed arbitrarily. Volumetric data are generated by interpolating plural sets of tomographic data, which have been reconstructed. For volumetric data reconstruction, such methods as cone-beam reconstruction, multi-slice reconstruction, and magnified reconstruction can be employed arbitrarily. Volumetric scanning executed with an X-ray detector having a multi-line configuration as mentioned above enables the reconstruction of volumetric data that cover a wide range. In CT fluoroscopy, since the rate of detection data gathering is set low, the time required for reconstruction by the reconstruction processor 42b is relatively short. As a result, real-time CT image data are generated in correspondence with the scanning.

In addition, the reconstruction processor 42b according to the present embodiment generates plural sets of volumetric data on the basis of plural sets of detection data (projection data) that have been acquired during one cycle of a cyclic motion in the subject E. The term "cyclic motion" means the motion of a target region in the subject E that repeats regularly in connection with the respiration or the heartbeat. For example, the expansion and contraction of the lungs in respiration is an example of cyclic motion. In addition, the term "cyclic motion" includes any motion of a region that results from a cyclic motion (e.g., the motion of a lesion in the lungs that moves in connection with the motion of the lungs in respiration).

As a specific example, the following case involves scanning that is executed with "n" revolutions of the rotating body (referred to as "first through n-th scanning revolutions") for a cycle of a cyclic motion, and first to n-th sets of detection data are acquired. In this case, the reconstruction processor 42b generates plural sets of tomographic data on the basis of the first set of detection data, which have been detected during the first scanning revolution. In addition, the reconstruction processor 42b generates the first set of volumetric data by interpolating these sets of tomographic data. The reconstruction processor 42b repeats the same processing on the detection data up to the n-th set of detection data and thereby generates "n" sets of volumetric data (first through n-th sets of volumetric data).

By the way, one cycle of a cyclic motion can be measured by a sensor, etc., which are provided along with the X-ray CT system 1 (or another sensing device can be used). For example, one respiratory cycle is detected by a respiration sensor, which includes, for example, a laser measuring device. The respiration sensor irradiates the abdomen of the subject E with a laser beam and measures the abdominal motion. The abdomen shows a cyclic motion under the influence of the respiration of the subject E. Thus, the respiration sensor can detect one cycle of the cyclic motion on the basis of the results of measurement. The X-ray CT system 1 (scanning-control unit 41) starts scanning with X-rays at a starting point of a cycle of the cyclic motion and stops the scanning at the ending point of the cycle, so that plural sets of detection data (data that are a source to projection data) are acquired for the one scanned cycle of the cyclic motion.

The moving-image creator 42c creates a moving image that shows a cyclic motion in the subject E, on the basis of at least a part of the plural sets of volumetric data. For example, let us suppose that the reconstruction processor 42b has generated first through n-th sets of volumetric data (plural sets of volumetric data) based on the first through n-th sets of detection data, which have been acquired for a cycle of the cyclic motion. In this case, the moving image creator 42*c* can create a moving image by arranging the first through n-th sets of volumetric data in chronological order, or the moving image creator 42*c* can create a moving image by using only a part of the plural sets of volumetric data generated by the reconstruction processor 42*b* (e.g., the first set to the (n−1)-th set of detection data). In this embodiment, the moving image creator 42*c* creates, as moving image, a three-dimensional moving-image that is achievable by constructing plural sets of volumetric data in chronological order.

The MPR processor 42*d* enables the displaying of an MPR view by rendering a three-dimensional image based on the volumetric data in a given direction (in other words, the MPR processor 42*d* creates MPR images). For example, the MPR processor 42*d* creates an MPR image by rendering, in a given direction, three-dimensional moving-images superposed one over another by the display controller 43 (details are described later). The MPR processor 42*d* can create MPR images in axial imaging, sagittal imaging, and coronal imaging, which correspond to the orthogonal three planes, and in oblique imaging, which corresponds to an arbitrary plane.

The display controller 43 executes various controls concerning image display. The display controller 43, for example, superposes a moving image over an image based on volumetric data and displays them together on the display unit 45.

The "image based on volumetric data", over which a moving image is superposed, includes, for example, an image based on an m-th set of volumetric data acquired by an m-th scanning session, which is executed at a timing different from the above mentioned session of continuous scanning (first through n-th scanning revolutions). Such image based on an m-th set of volumetric data can be, for example, an image acquired by a scanning session executed in the middle of the puncturing. Then, the image acquired by scanning in the middle of the puncturing is superposed with a moving image acquired by a session of continuous scanning performed prior to the puncturing, so that the movement of the site to be punctured (region undergoing a cyclic motion) can be monitored during the puncturing.

Instead, the "image based on volumetric data" may be based on partial volumetric data taken out from the volumetric data (first through n-th sets of volumetric data), which have been a source for creating a moving image. In other words, in a case where the first through n-th sets of volumetric data have been acquired during a session of continuous scanning, the moving image creator 42*c* creates a moving image based on the first through (n−1)-th sets of volumetric data, and the display controller 43 can superpose the moving image over the image based on the n-th set of volumetric data. An image created by superposing a moving image based on volumetric data (first through (n−1)-th sets of volumetric data) over an image based on partial volumetric data (n-th set of volumetric data) in this way is useful, for example, for determining a path of puncturing in planning a puncturing procedure. In other words, according to such an image, the cyclic motion of the site to be punctured can be recognized before actual puncturing takes place. By referring to the image, the puncturing plan can be made to reflect the cyclic motion.

By the way, it is so configured that the first through n-th sets of volumetric data and the m-th set of volumetric data are acquired, respectively, in the same frame number and the same pixel number of tomographic data as sources. It is also so configured that the same scanning conditions (the scanning position and the rotational speed of the rotating body 13) are applied both to the first through n-th scanning revolutions and to the m-th scanning revolution. In other words, the first through n-th sets of volumetric data and the m-th set of volumetric data are in the same coordinate system.

In this embodiment, the display controller 43 superposes a three-dimensional moving-image created by the moving image creator 42*c* on a three-dimensional image based on volumetric data (e.g., the m-th set of volumetric data). The MPR processor 42*d* creates an MPR image by rendering, in a given direction, the three-dimensional image that has been superposed with the three-dimensional moving-image. The display controller 43 displays the MPR image on the display unit 45. By the way, the display controller 43 may display on the display unit 45 the three-dimensional image (pseudo-three-dimensional image) that has been superposed with the three-dimensional moving-image without any additional processing.

Figure 2:
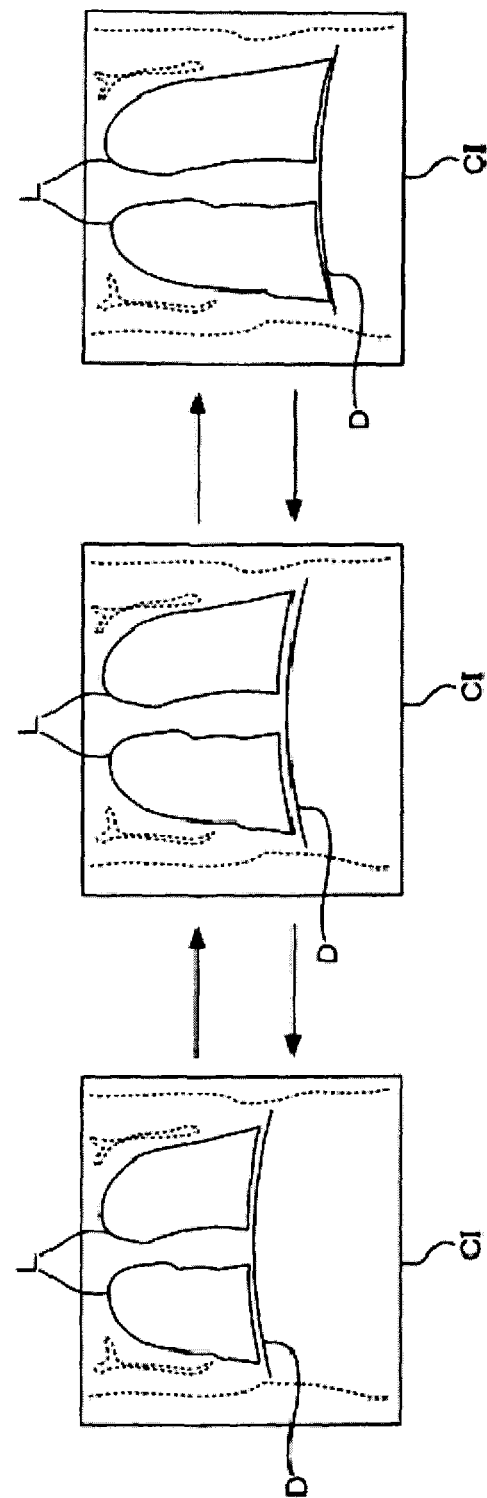
FIG. 2 is a set of drawings showing images that are displayed on a display unit according to the first embodiment.
Figure 3:
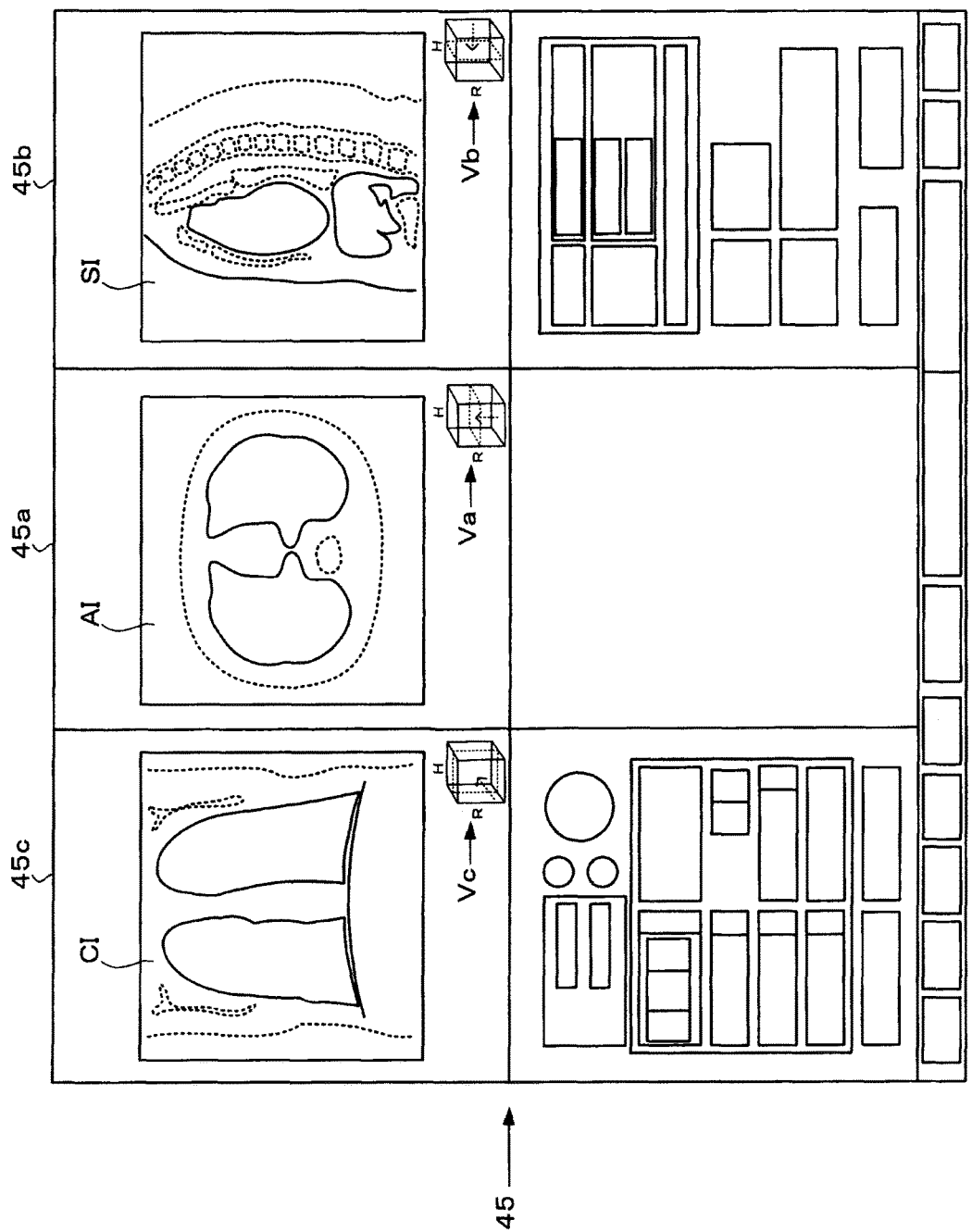
FIG. 3 is a drawing showing a display screen of the display unit according to the first embodiment.

FIG. 2 and FIG. 3 show examples of MPR image. By the way, in FIGS. 2 and 3, for the purpose of making parts displayed as moving images easily recognizable, the parts indicating moving images are shown by solid lines while the other parts are shown by dashed lines.

For example, FIG. 2 shows MPR images (coronal images CI) that have been acquired by rendering a three-dimensional image that has been superposed with a three-dimensional moving-image in the coronal direction. FIG. 2 shows the cyclic motion of the lungs L as an example. In the coronal images CI, not only the moving upward and downward of the diaphragm D under the influence of the respiration but also the cyclic change of the capacity of the lungs L are reproduced as a moving image (FIG. 2 shows views in which the capacity of the lungs L is at maximum (right-side drawing), at minimum (left-side drawing), and in the middle of the transition (drawing at the middle)).

Instead, as shown in FIG. 3, the display controller 43 can display on the display unit 45 not only coronal images CI but also MPR images that are rendered in the axial direction (axial images AI) and MPR images that are rendered in the sagittal direction (sagittal images SI), which are, for example, shown as display screens 45*a*-45*c*. MPR images are displayed in orthogonal three planes in this way, so that a cyclic motion in the subject E can be observed in these different directions. By the way, the axial image AI, the sagittal image SI, and the coronal image CI shown in FIG. 3 are images captured at a certain time point during a cycle of the cyclic motion.

The storage 44 is configured with semiconductor memory devices such as RAM and ROM. The storage 44 stores detection data and projection data, or CT image data that have been reconstruction-processed, moving images that have been created, etc.

The display unit 45 is configured with an arbitrary displaying device such as LCD (Liquid Crystal Display) or CRT (Cathode Ray Tube) display.

By the way, as shown in FIG. 3, viewing boxes Va–Vc that correspond to the MPR images are displayed on the display unit 45. The viewing boxes Va–Vc are icons that schematically indicate which imaging planes through the volumetric data the displayed MPR images represent. In the FIG. 3, viewing box Va is displayed for axial images AI in display screen 45*a*; viewing box Vb is displayed for sagittal images SI in display screen 45*b*; and viewing box Vc is displayed for coronal images CI in display screen 45*c*. In each viewing box, the area indicated by dashed line represents the sectional plane through the volumetric data. The arrow with a dashed line shown in each viewing box indicates the direction applied for the rendering. The control of displaying the viewing boxes is executed by the display controller 43.

The input unit 46 is used as input device to the console device 40 for execution of various operations. The input unit 46 comprises, for example, a key-board, a mouse, a track ball, a joystick, etc. In addition, the GUI (Graphical User Interface) used with the display unit 45 can be also used as a part of the input unit 46.

The control unit 47 controls the whole of the X-ray CT system 1 by individually controlling actions of the gantry apparatus 10, the patient table 30 and the console device 40. The control unit 47, for example, controls the scanning-control unit 41 to make the gantry apparatus 10 perform preliminary scanning and main scanning for acquisition of detection data. The control unit 47 also controls the processing unit 42 to execute various types of processing (e.g., preprocessing, reconstruction-processing, moving-image creation processing, and MPR processing) on the detection data.

<CT Fluoroscopy>

Here, an example of CT fluoroscopy is described. The following is an explanation of a biopsy that uses CT fluoroscopy.

At first, the scanning-control unit 41 starts scanning with X-rays in the state where the couch top 33 mounted with the subject E has been inserted in the through-opening 13a of the rotating body (first scanning session). The starting of scanning with X-rays is triggered by instruction input with a switch (not shown), which is provided on the gantry apparatus 10, or with a hand switch (not shown), which is connected to the X-ray CT system 1. By the way, the input unit 46 may be configured to serve such switching functions.

After the completion of the first scanning session, depending on what instruction input is given with switches, etc. the scanning-control unit 41 controls the bed drive 32 to temporarily pull out the couch top 33 out of the opening 13a of the rotating body. Then, a medical specialist performs puncturing to an attention site while referring to an image created based on the volumetric data that have been acquired during the first scanning session. In this way, in a case of puncturing, the radiation dose of the subject can be reduced by stopping the scanning with X-rays and pulling the subject E out of the opening 13a of the rotating body while a wider space is secured for the surgical operation than if the subject E would remain placed in the opening 13a of the rotating body.

After the puncturing has progressed to a certain extent, the medical specialist may want to see the state of the puncture needle (e.g., to make sure that the puncture needle is proceeding in the direction of the object of interest). In this case, the scanning-control unit 41 controls the bed drive 32 to insert the couch top 33 into the opening 13a of the rotating body, again. Then, the scanning-control unit 41 starts scanning with X-rays again (second scanning session). In other words, the scanning-control unit 41 controls the bed drive 32 to place the couch top 33 outside the opening 13a of the rotating body during the intermission between the first and second scanning sessions.

The scanning-control unit 41 repeats the actions of inserting and extracting the couch top 33 into and out of the opening 13a of the rotating body in accordance with instructions input by the medical specialist or others, until the completion of the biopsy.

By the way, it is possible to perform puncturing in the state where the couch top 33 is in the opening 13a of the rotating body (without repeating the insertion and extraction of the couch top 33). In this case also, reductions to the radiation dose can be facilitated by stopping X-ray generation during the intermission between the first and second scanning sessions.

<Actions>

Figure 4:
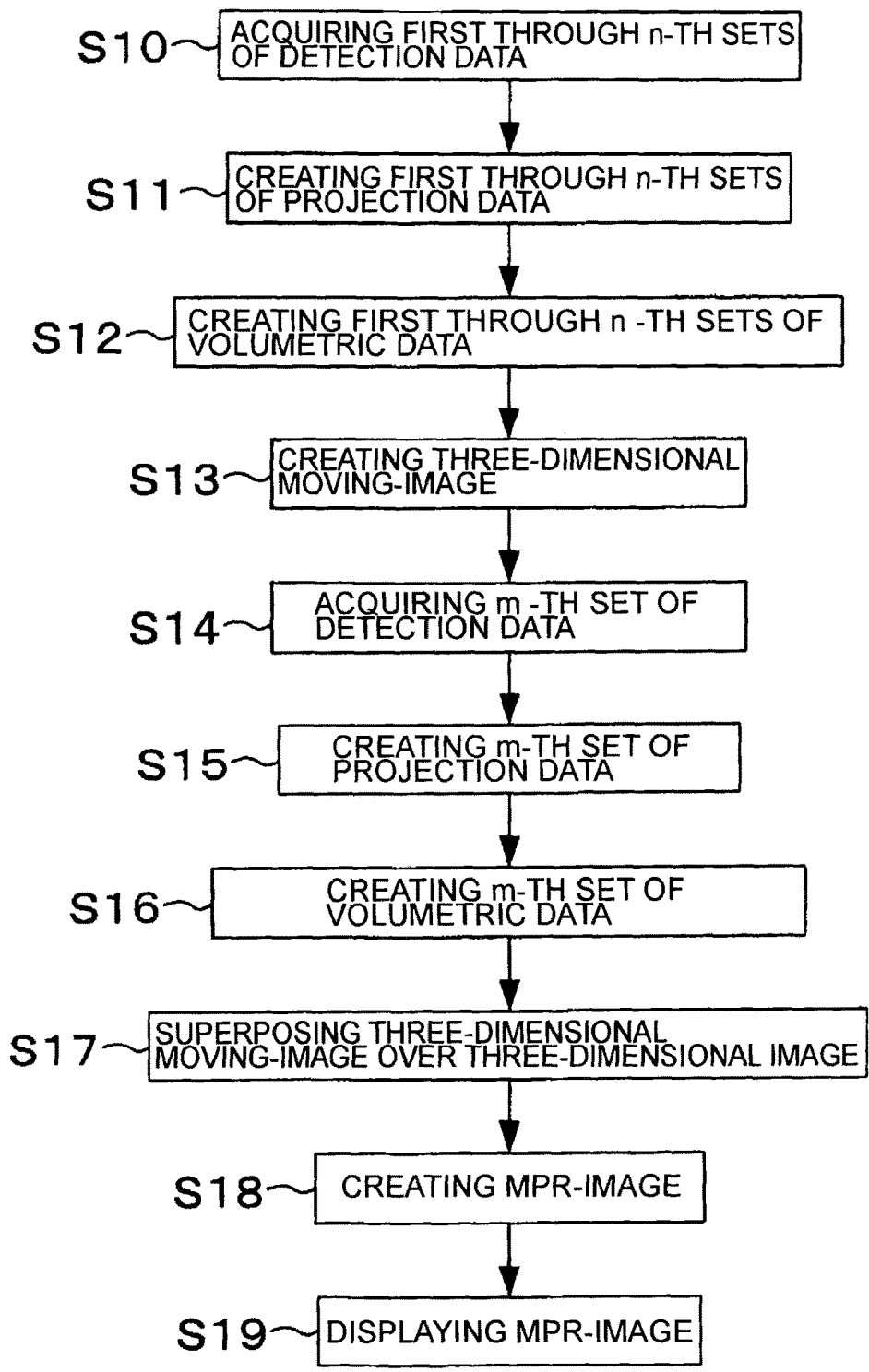
FIG. 4 is a flow chart showing an outline of actions taken by the X-ray CT system as a first embodiment.

Now, examples of action taken by an X-ray CT system 1 according to this embodiment are described with reference to FIG. 4. Here, a case of creating a moving image is described for showing a cyclic motion caused by the respiration. It is so conditioned that the volumetric data (first through n-th sets of volumetric data) on which a moving image is based and the volumetric data (m-th set of volumetric data) on which an image to be superposed with the moving image is based are, respectively, based on sets of detection data that are acquired at different timings.

At first, the X-ray CT system 1 executes scanning with X-rays by rotating the rotating body with a number of revolutions for a cycle of the respiration (first through n-th scanning revolutions) and generates a corresponding number of sets of volumetric data (first through n-th sets of volumetric data).

Specifically, the X-ray generator 11 radiates X-rays to the subject E, and the X-ray detector 12 acquires detection data by detecting X-rays that have passed through the subject E (S10). In this embodiment, the scanning is executed for "n" revolutions of the rotating body that correspond to one cycle of the respiration, so that plural sets of detection data are acquired in correspondence with the respective scanning revolutions (first through n-th sets of detection data). The data acquisition system 18 gathers the detection data detected by the X-ray detector 12 and sends them to the preprocessor 42a.

The preprocessor 42a executes preprocessing, for example, logarithmic transformation, on the first through n-th sets of detection data, which have been acquired at S10, and the preprocessor generates plural sets of projection data (first through n-th sets of projection data) (S11). The generated plural sets of projection data are sent to the reconstruction processor 42b under the control of the control unit 47.

The reconstruction processor 42b generates corresponding plural sets of volumetric data (first through n-th sets of volumetric data) based on the first through n-th sets of projection data, which have been generated at S11 (S12). The generated plural sets of volumetric data are sent to the moving image creator 42c under the control of the control unit 47.

The moving image creator 42c creates a three-dimensional moving-image based on the first through n-th sets of volumetric data, which have been generated at S12 (S13). The generated three-dimensional moving-image is a moving image that shows the cyclic motion, which is influenced by the respiration (e.g., expansion and contraction of the lungs). The three-dimensional moving-image created at S13 is stored in the storage 44.

Next, the X-ray CT system 1 executes scanning with X-rays at a timing different from the timings applied to the scanning performed at S10 and acquires a corresponding m-th set of volumetric data.

Specifically, the X-ray generator 11 radiates X-rays to the subject E, and the X-ray detector 12 acquires detection data by detecting X-rays that have passed through the subject E (S14). Here, the scanning is done for one revolution of the rotating body, and the detection data that correspond to this scanning session (m-th set of detection data) are acquired. The data acquisition system 18 gathers the detection data detected by the X-ray detector 12 and sends them to the preprocessor 42*a*. By the way, it is so configured that the same conditions are applied to the scanning executed both for the first through n-th scanning revolutions and for the m-th scanning revolution.

The preprocessor 42*a* executes such preprocessing as logarithmic transformation on the acquired m-th set of detection data and generates a set of projection data (m-th set of projection data) (S15). The generated set of projection data are sent to the reconstruction processor 42*b* under the control of the control unit 47.

The reconstruction processor 42*b* generates plural sets of tomographic data based on the m-th set of projection data, which has been generated at S15. In addition, the reconstruction processor 42*b* generates an m-th set of volumetric data by interpolating the plural sets of tomographic data (S16).

The display controller 43 superposes the three-dimensional moving-image created at S13, over a three-dimensional image based on the m-th set of volumetric data, which has been generated at S16 (S17).

The MPR processor 42*d* creates an MPR image by rendering, in a given direction, the three-dimensional image that has been superposed with the three-dimensional moving-image at S17 (S18). The created MPR image is displayed on the display unit 45 under the control of the display controller 43 (S19). For example, as shown in FIG. 3, the display controller 43 can display MPR images in three orthogonal planes (axial image AI, sagittal image SI, and coronal image CI).

By referring to the MPR image displayed at S19, the medical specialist can readily recognize the cyclic motion of the lungs under respiration from the image. While referring to this image, the medical specialist recognizing the motion of the lungs, for example, can insert a drainage tube for draining body fluids that have accumulated in the lungs.

By the way, the scanning-control unit 41, the processing unit 42, the display controller 43 and the control unit 47 may comprise such processing units as CPUs (Central Processing Units), GPUs (Graphic Processing Units), or ASICs (Application Specific Integrated Circuits), which are not shown here, and such storage devices as ROM (Read Only Memory), RAM (Random Access Memory) and/or HDDs (Hard Disc Drives), which are also not shown. The storage device stores a scanning-control program for execution of the functions of the scanning-control unit 41. The storage device also stores a processing program for execution of the functions of the processing unit 42, a display control program for execution of the functions of the display controller 43, and a control program for execution of the functions of the control unit 47. As the processing unit such as CPU executes each of the programs stored in the storage device, the functions of the respective parts are brought into realization.

For this embodiment, the configuration of the X-ray CT system 1 has been described as explained above, but the configuration to realize the actions of this embodiment is not limited to the X-ray CT system 1. For example, detection data acquired with the X-ray CT system can be sent to another device (for example, to an image display device called image viewer), which is separate from the X-ray CT system, and then the same functions as this embodiment can be realized in this separate device. In such a case, it is desirable for an image display device to be configured to include a processing unit 42, a display controller 43, and a display unit 45.

<Operation and Effects>

Now, the operation and effects of the present embodiment are described.

The X-ray CT system 1 as the present embodiment is an X-ray CT system that scans, with X-rays, an subject E whose targeted region is undergoing a cyclic motion and that thereby acquires detection data. The X-ray CT system 1 comprises a reconstruction processor 42*b*, a moving-image creator 42*c*, and a display controller 43. The reconstruction processor 42*b* generates plural sets of volumetric data based on the plural sets of detection data that have been acquired for one cycle of the cyclic motion. The moving-image creator 42*c* creates a moving image showing the cyclic motion in the subject on the basis of at least a part of the plural sets of volumetric data. The display controller 43 superposes the moving image over an image based on volumetric data and displays them together on the display unit 45.

Specifically, the moving-image creator 42*c* of the X-ray CT system 1 as this embodiment creates, as moving image, a three-dimensional moving-image based on at least a part of plural sets of volumetric data. Then, the display controller 43 superposes the three-dimensional moving-image over a three-dimensional image based on volumetric data and displays them together on the display unit 45.

In this way, the moving-image creator 42*c* creates a moving image (three-dimensional moving-image) that shows a motion in the subject E on the basis of at least a part of the plural sets of volumetric data, which have been reconstructed by the reconstruction processor 42*b*. Then, the display controller 43 superposes the moving image (three-dimensional moving-image) over an image (three-dimensional image) based on volumetric data and displays them together on the display unit 45. Thus, the real motion of the region undergoing a cyclic motion can be easily recognized with the images. In other words, the X-ray CT system of this embodiment is capable of displaying medical images that reflect a cyclic motion in the subject. Such medical images can be used to assist a medical procedure that is performed in reference to images, for example, biopsy or the above-mentioned draining method.

Furthermore, the X-ray CT system 1 of this embodiment includes an MPR processor 42*d*. The MPR processor 42*d* creates an MPR image in a predetermined plane that passes through a three-dimensional image, which has been created on the basis of volumetric data. The display controller 43 displays the MPR image on the display unit 45.

By displaying in this way an MPR view of a three-dimensional image that has been superposed with a three-dimensional moving image, the cyclic motion in the subject can be recognized in an arbitrary sectional view. In addition, if the MPR images are provided in plurality as seen in different directions, the cyclic motion in the subject can be even more readily recognized. In other words, the X-ray CT system of this embodiment is capable of displaying medical images that reflect a cyclic motion in the subject.

Moreover, the configuration of this embodiment can be applied to an image display device. In this case, the image display device comprises a display unit 45, a reconstruction processor 42*b*, a moving-image creator 42*c*, and a display controller 43. The reconstruction processor 42*b* generates plural sets of volumetric data on the basis of plural sets of detection data that have been acquired by scanning, with X-rays, a subject E including a region undergoing a cyclic motion, the scanning being executed continuously for one cycle of the cyclic motion. The moving-image creator 42*c* creates a moving image that shows the cyclic motion in the subject, on the basis of at least a part of the plural sets of volumetric data. The display controller 43 superposes the moving image over an image based on volumetric data and displays them together on the display unit 45.

Furthermore, the configuration of this embodiment can be realized as an image display method. Such image display method comprises a step where a reconstruction processor 42*b* generates plural sets of volumetric data on the basis of the plural sets of detection data that have been acquired by scanning, with X-rays, a subject E including a region undergoing a cyclic motion, the scanning being executed continuously for one cycle of the cyclic motion. The image display method further comprises a step where a moving-image creator 42*c* creates a moving image that shows the cyclic motion in the subject E, on the basis of at least a part of the plural sets of volumetric data. The image display method further comprises a step where a display controller 43 superposes the moving image over an image based on volumetric data and displays them together on a display unit 45.

Even in such an image display device or in such an image display method, the moving-image creator 42*c* creates a moving image that shows a motion in the subject E, on the basis of at least a part of the plural sets of volumetric data that have been reconstructed by the reconstruction processor 42*b*. Then, the display controller 43 superposes the moving image over an image based on volumetric data and displays them together on the display unit 45. Thus, the real motion of the region undergoing a cyclic motion can be easily recognized with the images. In other words, the image display device or the image display method of this embodiment is capable of displaying medical images that reflect a cyclic motion in the subject.

(Second Embodiment)

Now, the configuration of an X-ray CT system 1 as a second embodiment is described with reference to FIG. 5 and FIG. 6. In the second embodiment, a moving-image creator 42*c* creates a two-dimensional moving-image (MPR moving image) from a three-dimensional moving-image based on plural sets of volumetric data (for example, first through n-th sets of volumetric data). The configuration described now enables a display controller 43 to superpose the MPR moving image over a two-dimensional image based on volumetric data (for example, m-th set of volumetric data). By the way, no detailed description is given of the parts of the configuration that are the same as the first embodiment.

<System Configuration>

Figure 5:
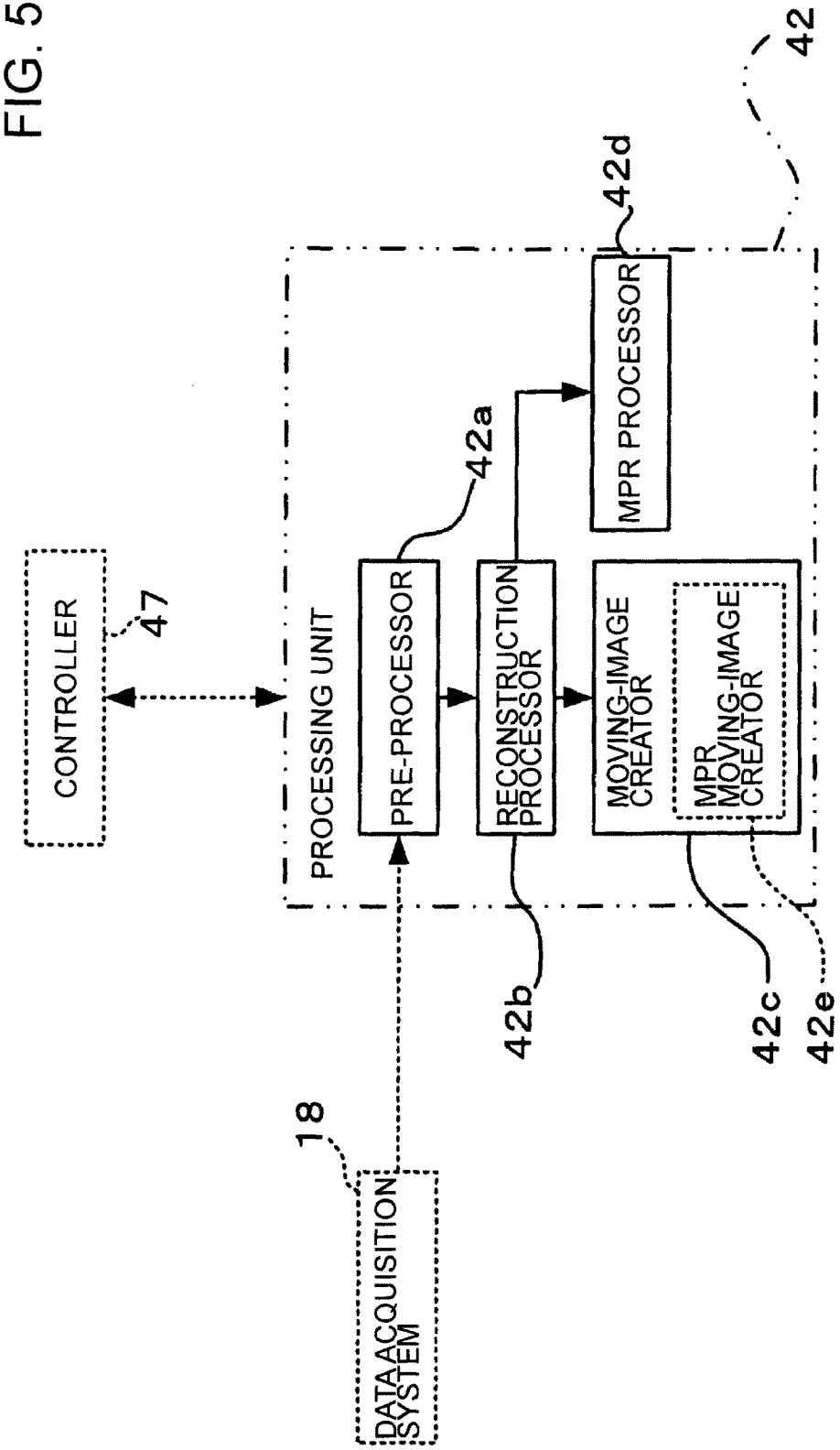
FIG. 5 is a block diagram showing the processing unit of an X-ray CT system as a second embodiment.
Figure 6:
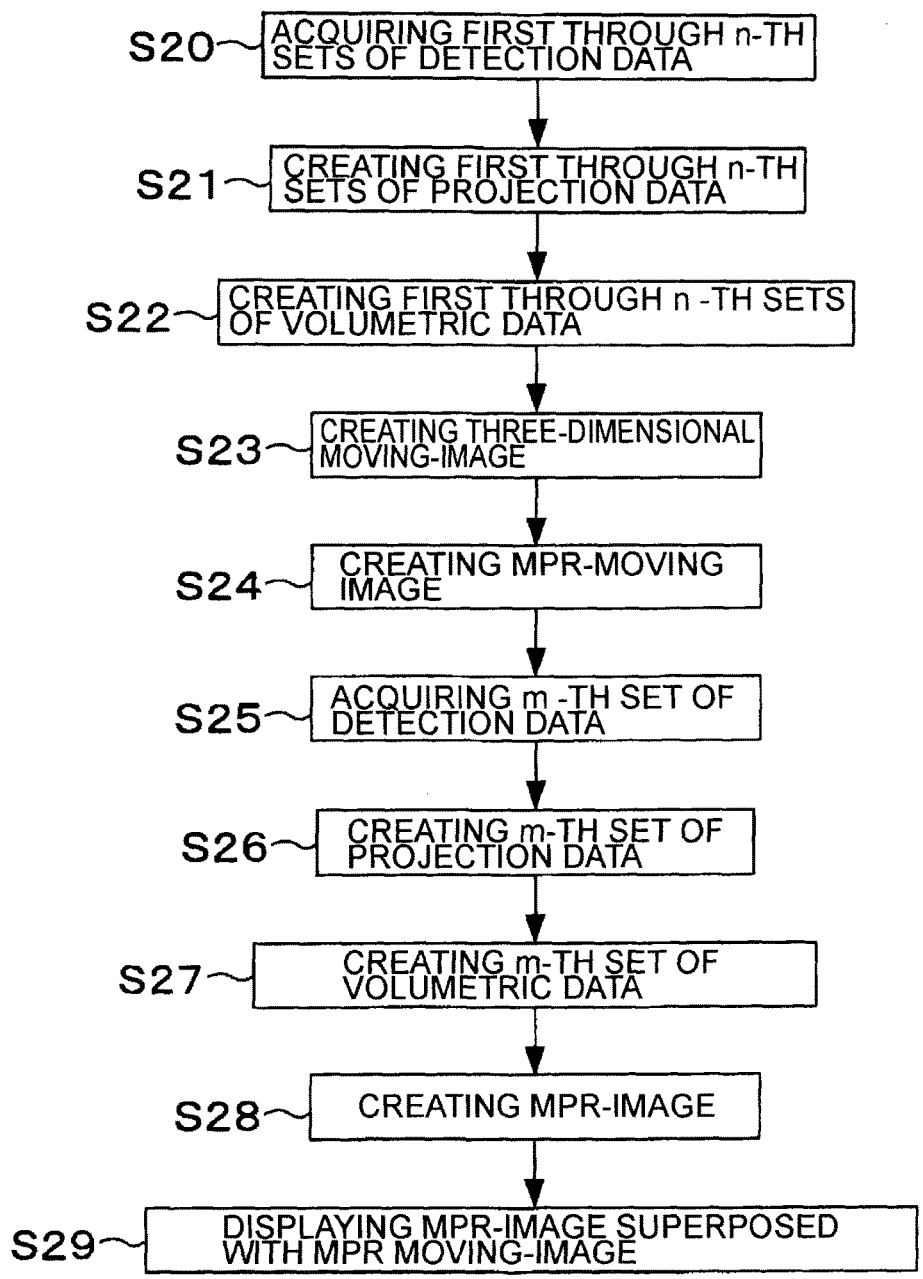
FIG. 6 is a flow chart showing an outline of actions taken by the X-ray CT system as a second embodiment.

FIG. 5 shows only the configuration of a processing unit 42 that is provided in the X-ray CT system 1 as this embodiment. The other parts of the configuration are the same as the first embodiment.

The moving-image creator 42*c* of this embodiment is configured to include an MPR moving-image creator 42*e*. The moving-image creator 42*c* creates a three-dimensional moving-image based on at least a part of plural sets of volumetric data in the same way as the first embodiment.

The MPR moving-image creator 42*e* creates an MPR moving image that is a view in a predetermined sectional plane through the three-dimensional moving-image. The MPR moving-image creator 42*e* creates a two-dimensional moving-image (i.e., MPR moving image) in a predetermined sectional plane by rendering, for example, a three-dimensional moving-image based on the first through n-th sets of volumetric data, in a given direction.

The MPR processor 42*d* of this embodiment enables the displaying of an MPR image by rendering, in a given direction, the volumetric data generated by the reconstruction processor 42*b* (i.e., the MPR processor 42*d* creates an MPR image (two-dimensional image)). The MPR processor 42*d* creates an MPR image by rendering, in a given direction, for example, an m-th set of volumetric data, which is different from the first through n-th sets of volumetric data, which are a source to a three-dimensional moving-image.

The display controller 43 superposes an MPR moving image that has been created by the MPR moving-image creator 42*e* over a two-dimensional image (MPR image) that has been crated on the basis of a set of volumetric data (e.g., m-th set of volumetric data) and display them on the display unit 45. By the way, in a case where the above mentioned MPR moving image is superposed over the MPR image based on the m-th set of volumetric data, it is desirable that the direction in which the rendering for a three-dimensional moving-image is executed through the first through n-th sets of volumetric data is the same direction as the rendering executed through the m-th set of volumetric data.

<Actions>

Now, examples of action taken by the X-ray CT system 1 as this embodiment are described with reference to FIG. 6. The following description concerns a case of creating a moving image that shows a cyclic motion caused by the respiration. It is so conditioned that the volumetric data (first through n-th sets of volumetric data) on which a moving image is based and the volumetric data (m-th set of volumetric data) on which an image to be superposed with the moving image is based are, respectively, based on sets of detection data that are acquired at different timings.

At first, the X-ray CT system 1 executes scanning with X-rays by rotating the rotating body with a number of revolutions for a cycle of the respiration (first through n-th scanning revolutions) and generates a corresponding number of sets of volumetric data (first through n-th sets of volumetric data).

Specifically, the X-ray generator 11 radiates X-rays to the subject E. The X-ray detector 12 acquires detection data by detecting X-rays that have passed through the subject E (S20). In this embodiment, the X-ray detector 12 acquires first through n-th sets of detection data in the same way as the first embodiment. The preprocessor 42*a* executes preprocessing, for example, logarithmic transformation, on the first through n-th sets of detection data, which have been acquired at S20, and the preprocessor generates plural sets of projection data (first through n-th sets of projection data) (S21). The reconstruction processor 42*b* generates corresponding plural sets of volumetric data (first through n-th sets of volumetric data) based on the first through n-th sets of projection data, which have been generated at S21 (S22). The moving image creator 42*c* creates a three-dimensional moving-image based on the first through n-th sets of volumetric data, which have been generated at S22 (S23).

Then, the MPR moving-image creator 42*e* creates an MPR moving image by rendering, in an arbitrary direction, the three-dimensional moving-image, which has been created at S23 (S24). The created MPR moving image is a two-dimensional moving-image that shows a cyclic motion caused by the respiration (e.g., expansion and contraction of the lungs). The MPR moving image created at S24 is stored in the storage 44.

Next, the X-ray CT system 1 executes scanning with X-rays at a timing different from the timing applied to the scanning performed at 520 and acquires an m-th set of volumetric data.

Specifically, the X-ray generator 11 radiates X-rays to the subject E. The X-ray detector 12 acquires detection data by detecting X-rays that have passed through the subject E (S25). Here, the scanning is done for one revolution of the rotating body, and the detection data that correspond to this scanning session (m-th set of detection data) are acquired. The preprocessor 42a executes such preprocessing as logarithmic transformation on the acquired m-th set of detection data and generates a set of projection data (m-th set of projection data) (S26). The reconstruction processor 42b generates plural sets of tomographic data based on the m-th set of projection data, which has been generated at S26. In addition, the reconstruction processor 42b generates an m-th set of volumetric data by interpolating the plural sets of tomographic data (S27).

Then, the MPR processor 42d creates an MPR image by rendering the m-th set of volumetric data, which has been generated at S27, in the same direction as the rendering done at S24 (S28). In other words, the MPR moving image created at S24 and the MPR image created at S28 are in sectional planes in the same direction.

The display controller 43 displays a two-dimensional image that results from the superposition of the MPR moving image created at S24 over the MPR image created at S28 on the display unit 45 (S29).

<Operation and Effects>

Now, the operation and effects of the present embodiment are described.

Specifically, the moving-image creator 42c of the X-ray CT system 1 as this embodiment creates a three-dimensional moving-image based on at least a part of plural sets of volumetric data. The moving-image creator 42c includes an MPR moving-image creator 42e. The MPR moving-image creator 42e creates an MPR moving image that is a view in a predetermined sectional plane through the three-dimensional moving-image. The display controller 43 superposes the MPR moving image over a two-dimensional image based on volumetric data and displays them together on the display unit 45.

In this way, in a case where an MPR moving image that has been created from a three-dimensional moving-image in advance is superposed over a corresponding MPR image (view in a sectional plane in the same direction as the MPR moving image), the real motion of a region undergoing a cyclic motion can be easily recognized with these two-dimensional views. In other words, the X-ray CT system of this embodiment is capable of displaying medical images that reflect a cyclic motion in the subject.

(Third Embodiment)

Now, the configuration of an X-ray CT system 1 as a third embodiment is described with reference to FIG. 7 and FIG. 8. In the third embodiment, a moving-image creator 42c creates a moving image on the basis of respective sets of MPR image data generated through plural sets of volumetric data (e.g., first through n-th sets of volumetric data). The configuration described now enables a display controller 43 to superpose the moving image over a two-dimensional image based on volumetric data (e.g., m-th set of volumetric data). By the way, there may be no detailed description of the parts of the configuration that are the same as the first embodiment or the second embodiment.

<System Configuration>

Figure 7:
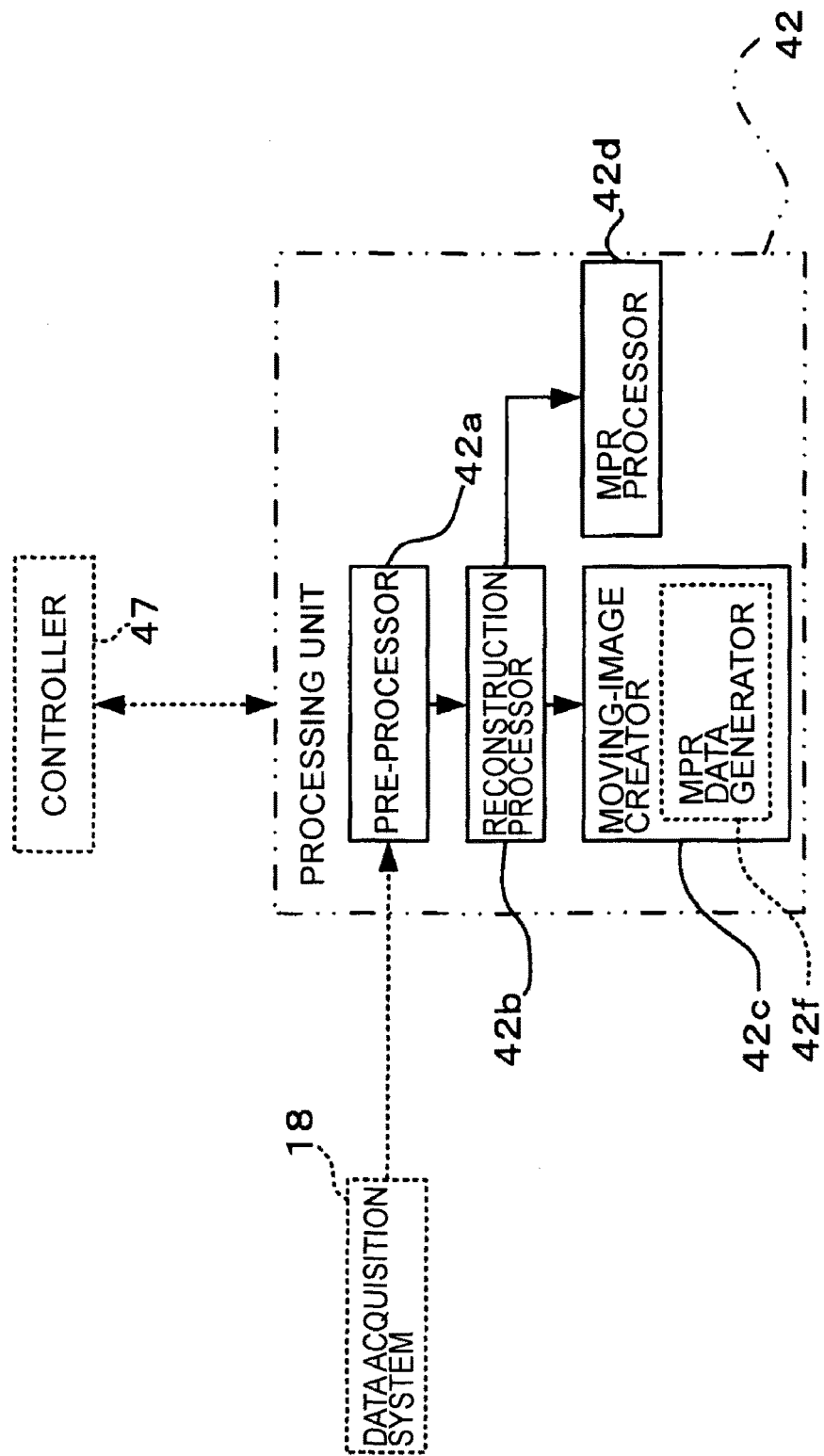
FIG. 7 is a block diagram showing the processing unit of an X-ray CT system as a third embodiment.
Figure 8:
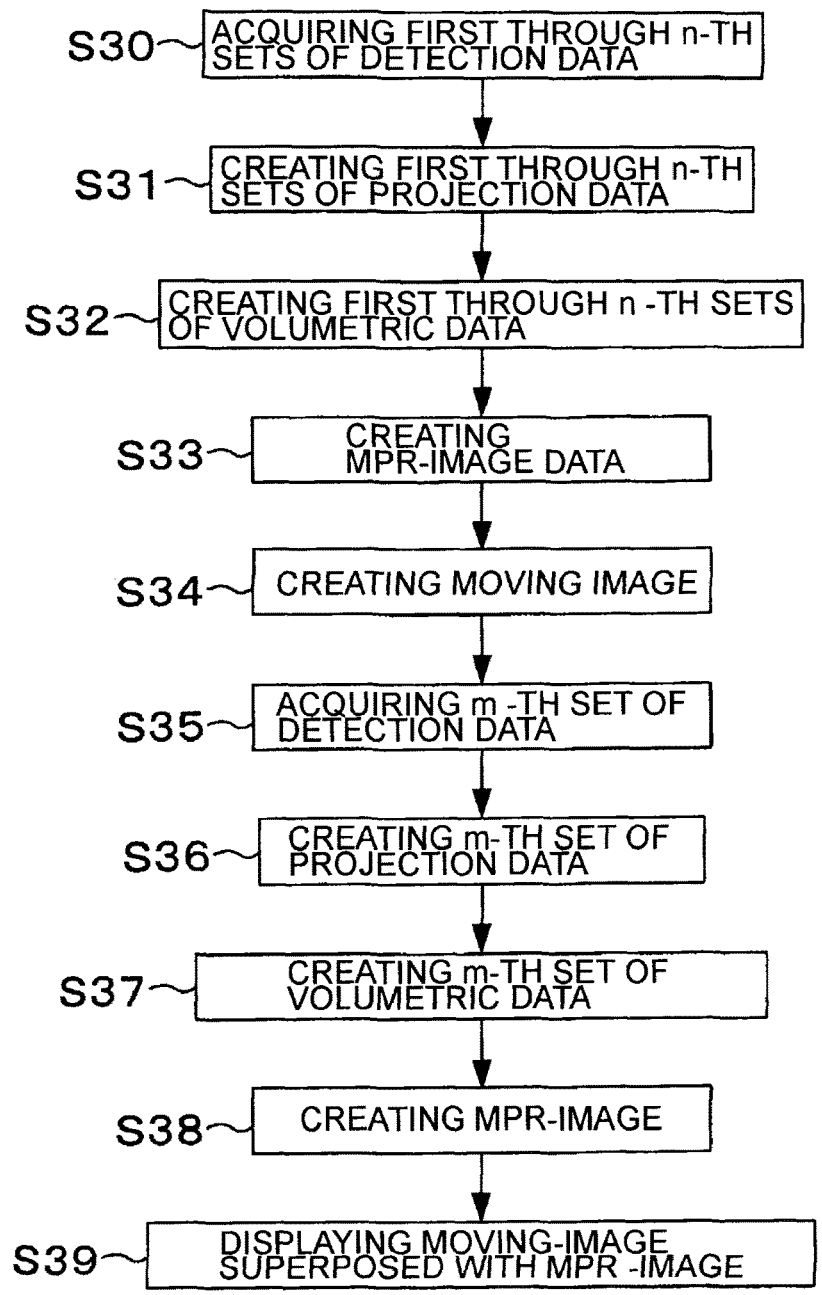
FIG. 8 is a flow chart showing an outline of actions taken by the X-ray CT system as a third embodiment.

FIG. 7 shows only the configuration of a processing unit 42 that is provided in the X-ray CT system 1 as this embodiment. The other parts of the configuration are the same as the first embodiment or the second embodiment.

The moving-image creator 42c comprises an MPR data generator 42f. The MPR data generator 42f generates plural sets of MPR image data each set representing a view in a predetermined sectional plane through a corresponding set of the plural sets of volumetric data. For example, the MPR data generator 42f generates first through n-th sets of MPR image data that correspond, respectively, to the first through n-th sets of volumetric data, by rendering in the same direction each of the first through n-th sets of volumetric data.

The moving-image creator 42c creates a two-dimensional moving-image on the basis of the plural sets of MPR image data, which have been generated by the MPR data generator 42f. For example, the moving-image creator 42c creates a moving image by arranging the first through n-th sets of MPR image data in chronological order.

The MPR processor 42d creates an MPR image (two-dimensional image) by rendering, in a given direction, a set of volumetric data (e.g., m-th set of volumetric data) generated by the reconstruction processor 42b in the same way as the second embodiment.

The display controller 43 superposes the moving image created by the moving-image creator 42c over the two-dimensional image (MPR image), which has been crated on the basis of a set of volumetric data (e.g., m-th set of volumetric data), and displays them together on the display unit 45. By the way, in a case where the above mentioned moving image is superposed over the MPR image based on the m-th set of volumetric data, it is desirable that the direction in which the rendering is executed through the first through n-th sets of volumetric data is the same direction as the rendering executed through the m-th set of volumetric data.

<Actions>

Now, examples of action taken by the X-ray CT system 1 as this embodiment are described with reference to FIG. 8. The following description concerns a case of creating a moving image that shows a cyclic motion caused by the respiration. It is so conditioned that the volumetric data (first through n-th sets of volumetric data) on which a moving image is based and the volumetric data (m-th set of volumetric data) on which an image to be superposed with the moving image is based are, respectively, based on sets of detection data that are acquired at different timings.

At first, the X-ray CT system 1 executes scanning with X-rays by rotating the rotating body with a number of revolutions for a cycle of the respiration (first through n-th scanning revolutions) and generates a corresponding number of sets of volumetric data (first through n-th sets of volumetric data).

Specifically, the X-ray generator 11 radiates X-rays to the subject E. The X-ray detector 12 acquires detection data by detecting X-rays that have passed through the subject E (S30). In this embodiment, the X-ray detector 12 acquires first through n-th sets of detection data in the same way as the first embodiment and the second embodiment. The preprocessor 42a executes preprocessing, for example, logarithmic transformation, on the first through n-th sets of detection data, which have been acquired at S30, and the preprocessor generates plural sets of projection data (first through n-th sets of projection data) (S31). The reconstruction processor 42b generates corresponding plural sets of volumetric data (first through n-th sets of volumetric data) on the basis of the first through n-th sets of projection data, which have been generated at S31 (S32).

Then, the MPR data generator 42f generates first through n-th sets of MPR image data that correspond, respectively, to the first through n-th sets of volumetric data by rendering in the same direction each of the first through n-th sets of volumetric data. The moving-image creator 42c creates a moving image based on the first through n-th sets of MPR image data, which have been generated at S33 (S34). The created moving image is a two-dimensional moving-image that shows a cyclic motion caused by the respiration (e.g., expansion and contraction of the lungs). The MPR moving image created at S34 is stored in the storage 44.

Next, the X-ray CT system 1 executes scanning with X-rays at a timing different from the timing applied to the scanning performed at S30 and acquires an m-th set of volumetric data.

Specifically, the X-ray generator 11 radiates X-rays to the subject E. The X-ray detector 12 acquires detection data by detecting X-rays that have passed through the subject E (S35). Here, the scanning is done for one revolution of the rotating body, and the detection data that correspond to this scanning session (m-th set of detection data) are acquired. The preprocessor 42a executes such preprocessing as logarithmic transformation on the acquired m-th set of detection data and generates a set of projection data (m-th set of projection data) (S36). The reconstruction processor 42b generates plural sets of tomographic data based on the m-th set of projection data, which has been generated at S36. In addition, the reconstruction processor 42b generates an m-th set of volumetric data by interpolating the plural sets of tomographic data (S37).

Then, the MPR processor 42d creates an MPR image by rendering the m-th set of volumetric data in the same direction as the rendering done at S33 (S38). In other words, the MPR image data (or the image based on the MPR image data) generated at S33 and the MPR image created at S38 are in sectional planes in the same direction.

The display controller 43 creates a two-dimensional image by superposing the moving image created at S34 over the MPR image created at S38, and the display controller displays the two-dimensional image on the display unit 45 (S39).

<Operation and Effects>

Now, the operation and effects of the present embodiment are described.

The moving-image creator 42c of the X-ray CT system 1 as this embodiment comprises an MPR data generator 42f. The MPR data generator 42f generates plural sets of MPR image data each set representing a view in a predetermined sectional plane through a corresponding set of plural sets of volumetric data. The moving-image creator 42c creates a moving image based on the plural sets of MPR image data. The display controller 43 superposes the moving image over a two-dimensional image based on volumetric data and displays them together on the display unit 45.

In this way, in a case where a moving image that has been created from plural sets of MPR image data is superposed over a corresponding two-dimensional image (MPR image, which is a view in a sectional plane in the same direction as the moving image), the real motion of a region undergoing a cyclic motion can be easily recognized with the two-dimensional images. In other words, the X-ray CT system of this embodiment is capable of displaying medical images that reflect a cyclic motion in the subject.

(Variant Embodiment 1 of the First Through Third Embodiments)

The above-mentioned embodiments have been described in relation to an example in which all plural sets of volumetric data are used for creation of a moving image. According to such example, the region undergoing a cyclic motion can be recognized as a whole. On the other hand, there is a case where it is desirable to observe only part of the region undergoing a cyclic motion. For example, in a case where puncturing is performed for a lesion site in the lungs, the lesion site also moves in synchronization with the motion of the lungs under respiration. In this case, it may be desirable to observe only the motion of the lesion site. This variant embodiment is described as an X-ray CT system that is capable of displaying the motion of a part (e.g., a lesion site) of a region undergoing a cyclic motion.

Figure 9:
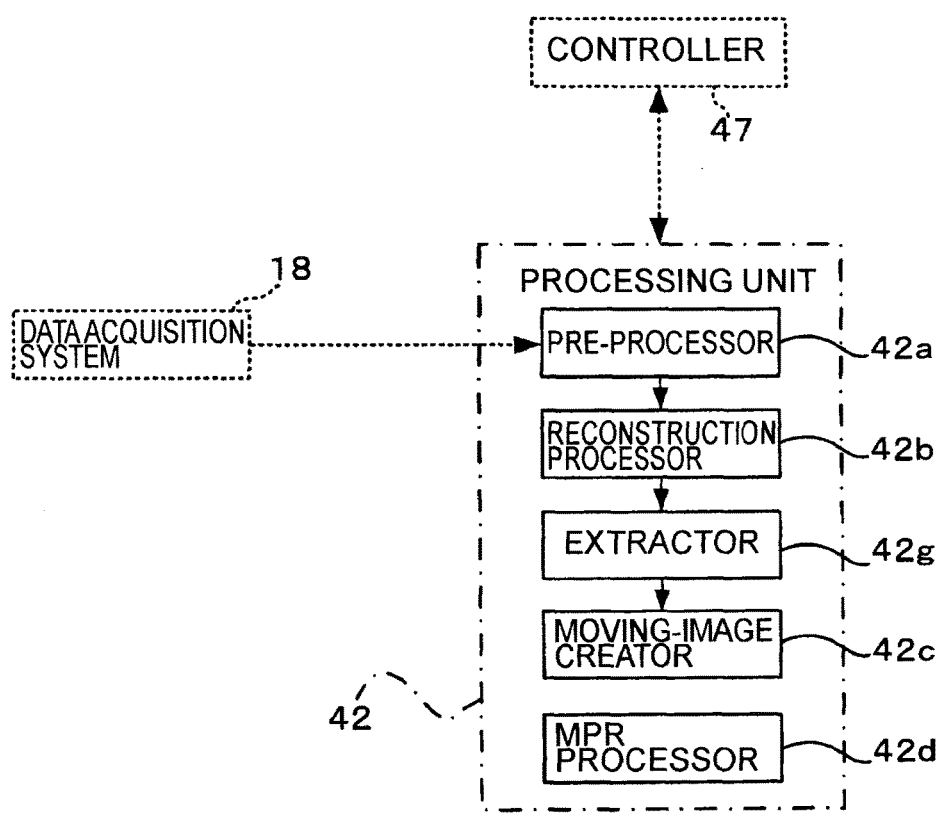
FIG. 9 is a block diagram showing the processing unit of an X-ray CT system as a variant embodiment 1 of the first through third embodiments.

FIG. 9 is a block diagram showing the configuration of a processing unit 42 provided in the X-ray CT system 1 as this variant embodiment. The processing unit 42 of the X-ray CT system 1 is configured to include an extractor 42g. The extractor 42g extracts data that correspond to an arbitrarily selected part of the region undergoing a cyclic motion from plural sets of volumetric data, which have been reconstructed by the reconstruction processor 42b. Specifically, the extractor 42g executes image-processing on each set of volumetric data and specifies an area that corresponds to the part of the region, in each set of volumetric data. Then, the extractor 42g extracts the part of the volumetric data that correspond to the area. For the image-processing, such methods as lesion-glowing and threshold processing can be applied to the gradation value of each voxel.

On the basis of the part of the volumetric data extracted by the extractor 42g, the moving-image creator 42c can create a moving image based on extracted volumetric data by executing any one of the methods of moving-image creation processing described in the first through third embodiments. The display controller 43 superposes the moving image based on extracted volumetric data over a three-dimensional image or an MPR image and displays the superposed images on the display unit 45. By the way, although the configuration shown in FIG. 9 is based on the configuration of the first embodiment, it is also possible to provide an extractor 42g in the configuration of the second embodiment or the third embodiment.

(Variant Embodiment 2 of the First Through Third Embodiments)

In a case where an image based on volumetric data and a moving image are superposed one over the other, it is desirable that they be displayed distinctively from each other. This variant embodiment is described as an X-ray CT system that is capable of changing displaying conditions applied to the image based on volumetric data and to the moving image.

Figure 10:
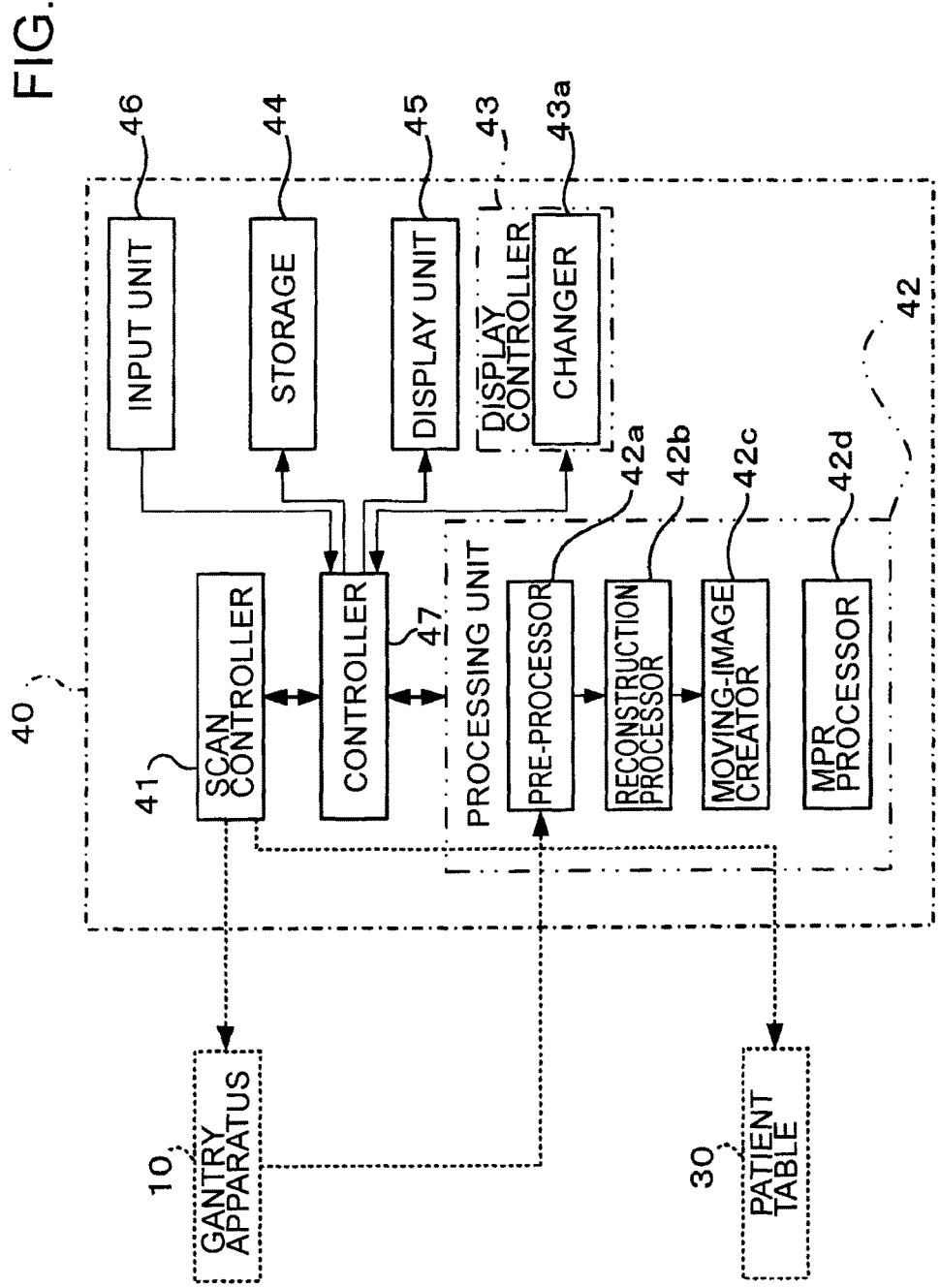
FIG. 10 is a block diagram showing the console device of an X-ray CT system as another variant embodiment 2 of the first through third embodiments.

FIG. 10 is a block diagram showing the configuration of a console device 40 provided in the X-ray CT system 1 as this variant embodiment. The display controller 43 of the X-ray CT system 1 is configured to include a changer 43a, which changes the displaying conditions applied to the image based on volumetric data and to the moving image. Specifically, the changer 43a changes at least one of the following conditions: colors used for the image (and moving image), transparency, and CT values. For example, the changer 43a so changes the conditions that the image based on volumetric data is displayed in grayscale, and the moving image is displayed in color. If the images are displayed in differing colors in such a way, then the region undergoing a cyclic motion is made readily recognizable in the images. Instead, the changer 43a can raise the transparency of the image based on volumetric data and lower the transparency of the moving image. If the moving image is displayed at a lowered transparency in such a way, then the region undergoing a cyclic motion can be enhanced in the images. By the way, although the configuration shown in FIG. 10 is based on the configuration of the first embodiment, it is also possible to provide a changer 43a in the configuration of the second embodiment or the third embodiment.

(Fourth Embodiment)

Now, the configuration of an X-ray CT system 1 as a fourth embodiment is described with reference to FIG. 11 through FIG. 13. The fourth embodiment is described as a configuration in which the display controller 43 displays images by superposing a trace image that shows a trace of a cyclic motion in the subject over an image based on volumetric data. The term "trace" used for this embodiment means an area that indicates the range where the region undergoing a cyclic motion moves (or part of the range). By the way, there may be no detailed description of the parts of the configuration that are the same as the first through third embodiments.

<System Configuration>

Figure 11:
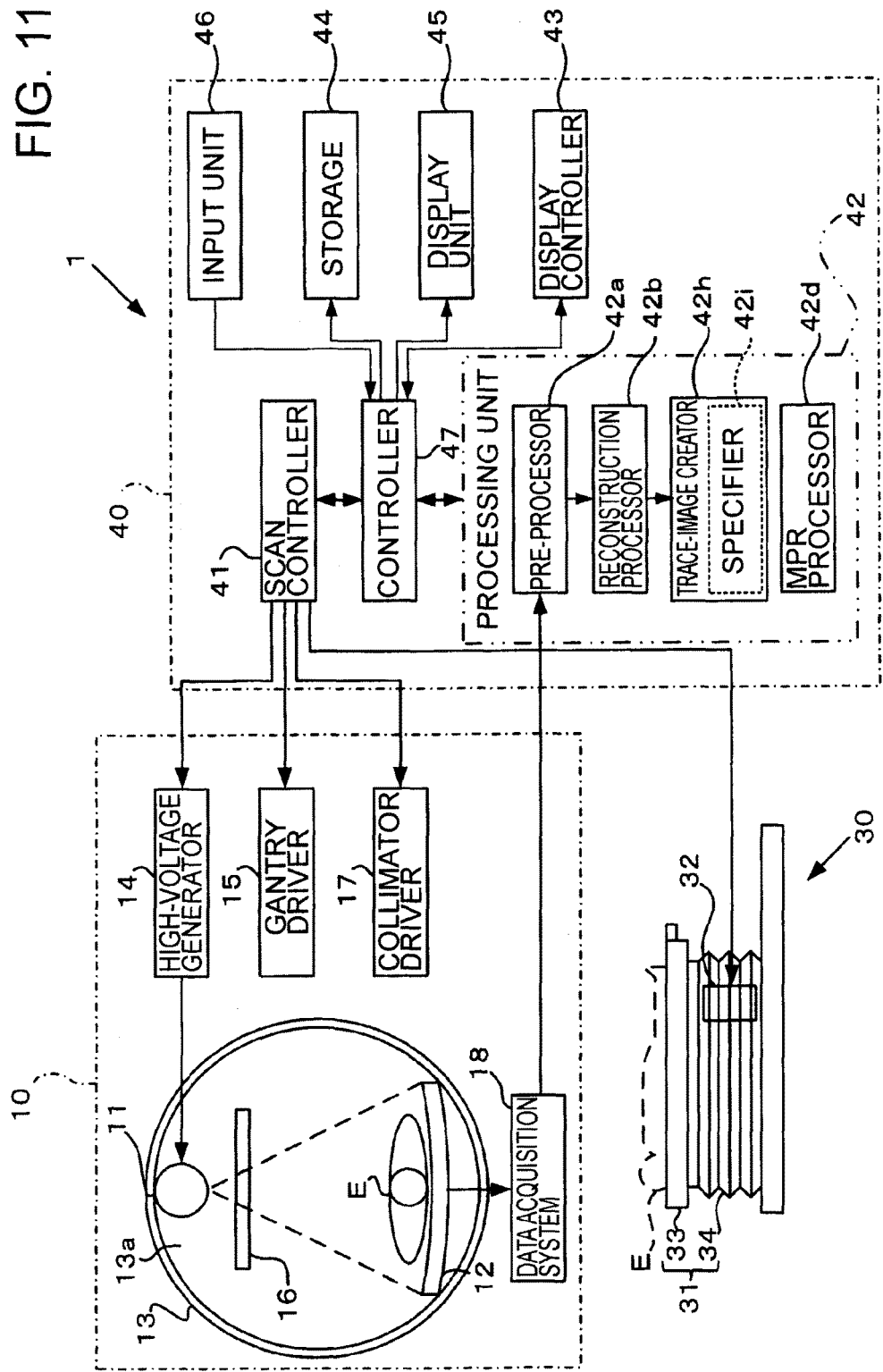
FIG. 11 is a block diagram showing an X-ray CT system as a fourth embodiment.

FIG. 11 is a block diagram showing the configuration of the X-ray CT system 1 as this embodiment.

The processing unit 42 of the X-ray CT system 1 as this embodiment is configured to include a preprocessor 42a, a reconstruction processor 42b, a trace-image creator 42h, and an MPR processor 42d. Since the preprocessor 42a and the reconstruction processor 42b are the same in configuration as the first through third embodiments, detailed description is not provided here.

The trace-image creator 42h creates a trace image that shows a trace of a cyclic motion in the subject E, on the basis of at least a part of the plurality of sets of volumetric data created by the reconstruction processor 42b. In this embodiment, the trace-image creator 42h includes a specifier 42i.

The specifier 42i locates a region undergoing a cyclic motion in each of the plural sets of volumetric data. For example, let us suppose that the reconstruction processor 42b has generated first through n-th sets of volumetric data based on the first through n-th sets of detection data, which have been acquired for a cycle of the cyclic motion. The specifier 42i performs such image-processing as lesion-glowing on each set of volumetric data and thereby specifies the three-dimensional position (coordinates) of a region undergoing a cyclic motion (e.g., lesion site).

The trace-image creator 42h creates a three-dimensional trace image that indicates the trace of the region undergoing a cyclic motion by connecting a plurality of three-dimensional positions specified by the specifier 42i. By the way, the specifier 42i specifies the three-dimensional position of the region undergoing a cyclic motion on the basis of parts of the first through n-th sets of volumetric data (e.g., on every other set of volumetric data). Then, the trace-image creator 42h achieves a rough trace image by connecting these specified positions.

The MPR processor 42d of this embodiment creates an MPR image by rendering, in a given direction, a three-dimensional image (details are described later) that is superposed with a three-dimensional trace image by the display controller 43.

The display controller 43 superposes a trace image over an image based on volumetric data and displays them together on the display unit 45. For example, the display controller 43 superposes a three-dimensional trace image created by the trace-image creator 42h over a three-dimensional image based on the m-th set of volumetric data. The MPR processor 42d creates an MPR image by rendering, in a given direction, the three-dimensional image that has been superposed with the three-dimensional trace image. The display controller 43 displays the MPR image on the display unit 45. By the way, the display controller 43 may display, on the display unit 45, the three-dimensional image (pseudo-three-dimensional image) that has been superposed with the three-dimensional trace image without any additional processing.

Figure 12:
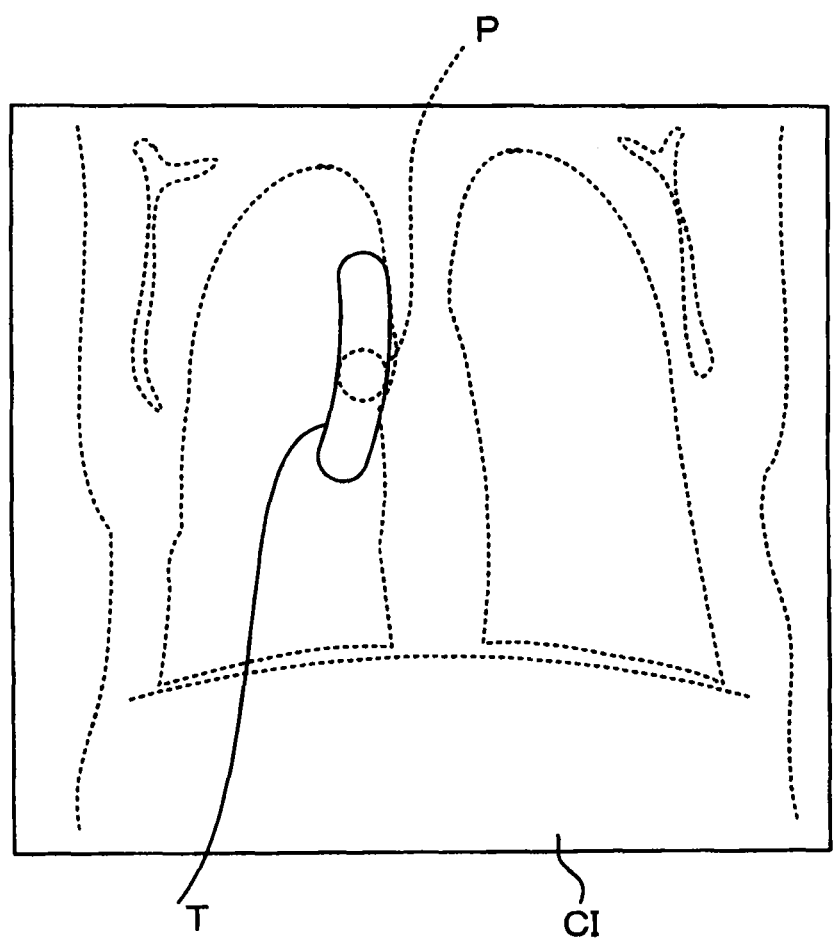
FIG. 12 is a drawing showing images that are displayed on a display unit according to the fourth embodiment.
Figure 13:
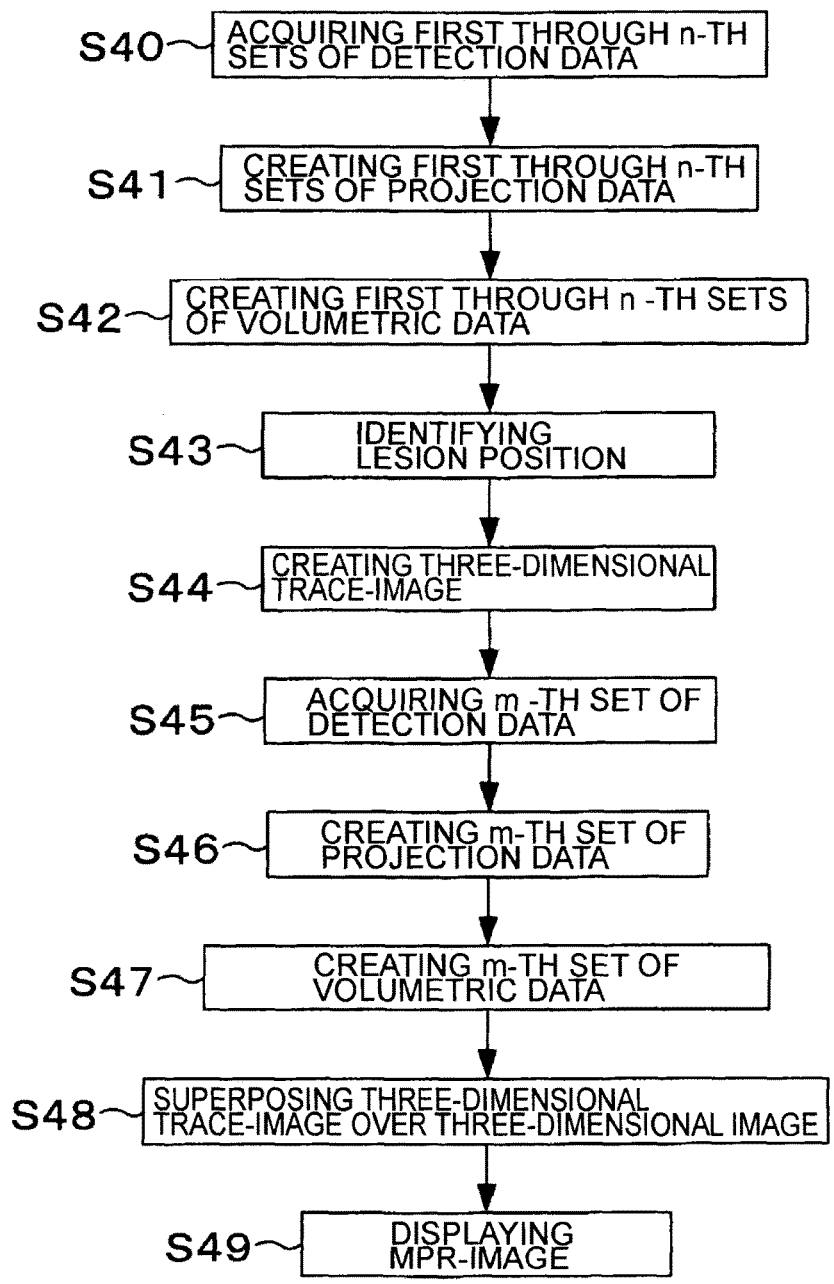
FIG. 13 is a flow chart showing an outline of actions taken by the X-ray CT system as a fourth embodiment.

FIG. 12 shows an example of MPR image superposed with a trace image. This is an MPR image (coronal image CI) acquired by rendering a three-dimensional image that has been superposed with a three-dimensional trace image in the coronal direction. In the coronal image CI, the range of the motion of a lesion site P (region undergoing a cyclic motion) is shown as a trace image T. By the way, in FIG. 12, for the purpose of making the traced part easily understandable, the trace image T is indicated by solid line while the other parts are indicated by dashed line. In addition, the MPR processor 42d can create three MPR images by rendering a three-dimensional image that has been superposed with a three-dimensional trace image, respectively in the axial, sagittal, and coronal directions.

<Actions>

Now, examples of action taken by the X-ray CT system 1 as this embodiment are described with reference to FIG. 13. Here, the description is made on a case of creating a trace image that indicates a trace of a lesion site P undergoing a cyclic motion. Furthermore, it is so conditioned that the volumetric data (first through n-th sets of volumetric data) on which a trace image is based and the volumetric data (m-th set of volumetric data) on which an image to be superposed with the trace image is based are, respectively, based on sets of detection data that are acquired at different timings.

At first, the X-ray CT system 1 executes scanning with X-rays by rotating the rotating body with a number of revolutions for a cycle of the respiration (first through n-th scanning revolutions) and generates a corresponding number of sets of volumetric data (first through n-th sets of volumetric data).

Specifically, the X-ray generator 11 radiates X-rays to the subject E. The X-ray detector 12 acquires detection data by detecting X-rays that have passed through the subject E (S40). In this embodiment, the X-ray detector 12 acquires first through n-th sets of detection data in the same way as the first through third embodiments. The preprocessor 42a executes preprocessing, for example, logarithmic transformation, on the first through n-th sets of detection data, which have been acquired at S40, and the preprocessor generates plural sets of projection data (first through n-th sets of projection data) (S41). The reconstruction processor 42b generates corresponding plural sets of volumetric data (first through n-th sets of volumetric data) based on the first through n-th sets of projection data, which have been generated at S41 (S42).

Then, the specifier 42i specifies positions (P1-Pn) of a lesion site P undergoing a cyclic motion in each of the first through n-th sets of volumetric data, which have been generated at S42 (S43). The trace-image creator 42h creates a three-dimensional trace image by connecting the positions P1-Pn specified by the specifier 42i (S44). The created trace image is a three-dimensional image that shows a trace of the motion of a lesion site P. The trace image created at S44 is stored in the storage 44.

Next, the X-ray CT system 1 executes scanning with X-rays at a timing different from the timing applied to the scanning performed at S40 and acquires an m-th set of volumetric data.

Specifically, the X-ray generator 11 radiates X-rays to the subject E. The X-ray detector 12 acquires detection data by detecting X-rays that have passed through the subject E (S45). Here, the scanning is done for one revolution of the rotating body, and the detection data that correspond to this scanning session (m-th set of detection data) are acquired. The preprocessor 42a executes such preprocessing as logarithmic transformation on the acquired m-th set of detection data and generates a set of projection data (m-th set of projection data) (S46). The reconstruction processor 42b generates plural sets of tomographic data based on the m-th set of projection data, which has been generated at S46. In addition, the reconstruction processor 42b generates an m-th set of volumetric data by interpolating the plural sets of tomographic data (S47).

The display controller 43 superposes the three-dimensional trace image, which has been created at S44, over a three-dimensional image based on the m-th set of volumetric data, which have been generated at S47 (S48).

The MPR processor 42d creates an MPR image by rendering, in a given direction, the three-dimensional image, which has been superposed with the three-dimensional trace image at S48. The created MPR image is displayed on the display unit 45 under the control of the display controller 43 (S49).

By referring to the MPR image displayed at S49, the medical specialist can easily recognize the trace of a lesion site P undergoing a cyclic motion in the image. For example, in a case of puncturing performed to the lesion site P, the medical specialist, by referring to this image, can expect the actual motion of the lesion site P on the basis of the trace shown in the image. This results in an improvement to the accuracy of the puncturing.

<Operation and Effects>

Now, the operation and effects of the present embodiment are described.

The X-ray CT system 1 as the present embodiment is an X-ray CT system that scans, with X-rays, a subject E including a region undergoing a cyclic motion and that thereby acquires detection data. The X-ray CT system 1 comprises a reconstruction processor 42b, a trace-image creator 42h, and a display controller 43. The reconstruction processor 42b generates plural sets of volumetric data based on the plural sets of detection data that have been acquired for one cycle of the cyclic motion. The trace-image creator 42h creates a trace image that shows a trace of the cyclic motion, on the basis of at least a part of the plural sets of volumetric data. The display controller 43 superposes the trace image over an image based on volumetric data and displays them together on the display unit 45.

Specifically, the trace-image creator 42h of the X-ray CT system 1 as this embodiment comprises a specifier 42i, which specifies the positions of a region undergoing a cyclic motion in the respective plural sets of volumetric data. The trace-image creator 42h creates a three-dimensional trace image based on the specified positions of the region. The display controller 43 superposes the three-dimensional trace image over a three-dimensional image based on volumetric data and displays them together on the display unit 45.

In this way, the trace-image creator 42h creates a trace image that shows a trace of a region undergoing a cyclic motion, on the basis of at least a part of the plural sets of volumetric data that have been reconstructed by the reconstruction processor 42b. Then, the display controller 43 superposes the trace image over an image based on volumetric data and displays them on the display unit 45. Thus, the range of the real motion of the region undergoing a cyclic motion can be easily recognized in the images. In other words, the X-ray CT system of this embodiment is capable of displaying medical images that reflect a cyclic motion in the subject.

Furthermore, the X-ray CT system 1 of this embodiment includes an MPR processor 42d. The MPR processor 42d creates an MPR image in a predetermined plane that passes through a three-dimensional image that has been created on the basis of volumetric data. The display controller 43 displays the MPR image on the display unit 45.

By displaying, in MPR image, a three-dimensional image that has been superposed with a three-dimensional trace image in this way, the range where the region undergoing a cyclic motion can actually move can be recognized in a given direction. In addition, if a plurality of MPR images in different directions are provided, then the range of the actual motion of the region undergoing a cyclic motion can be more easily understood. In other words, the X-ray CT system of this embodiment is capable of displaying medical images that reflect a cyclic motion in the subject.

Furthermore, the configuration of this embodiment can be applied to an image display device. Such image display device comprises a display unit 45, a reconstruction processor 42b, a trace-image creator 42h, and a display controller 43. The reconstruction processor 42b generates plural sets of volumetric data based on the plural sets of detection data that have been acquired by scanning, with X-rays, a subject E including a region undergoing a cyclic motion, the scanning being executed continuously for one cycle of the cyclic motion. The trace-image creator 42h creates a trace image that shows a trace of the cyclic motion, on the basis of at least a part of the plural sets of volumetric data. The display controller 43 superposes the trace image over an image based on volumetric data and displays them on the display unit 45.

Moreover, the configuration of this embodiment can be realized as an image display method. Such image display method comprises a step where a reconstruction processor 42b generates plural sets of volumetric data on the basis of the plural sets of detection data that have been acquired by scanning, with X-rays, a subject E including a region undergoing a cyclic motion, the scanning being executed continuously for one cycle of the cyclic motion. The method further comprises a step where a trace-image creator 42h creates a trace image that shows a trace of the cyclic motion on the basis of at least a part of the plural sets of volumetric data. The image display method further comprises a step where a display controller 43 superposes the trace image over an image based on volumetric data and displays them on a display unit 45.

Even in such an image display device or such an image display method, the trace-image creator 42h creates a trace image that shows a trace of a region undergoing a cyclic motion, on the basis of at least a part of the plural sets of volumetric data that have been reconstructed by the reconstruction processor 42b. Then, the display controller 43 superposes the trace image over an image based on volumetric data and displays them on the display unit 45. Thus, the range of the real motion of the region undergoing a cyclic motion can be easily recognized in the images. In other words, the image display device or the image display method of this embodiment is capable of displaying medical images that reflect a cyclic motion in the subject.

(Fifth Embodiment)

Now, the configuration of an X-ray CT system 1 as a fifth embodiment is described with reference to FIG. 14 and FIG. 15. The fifth embodiment is described as a configuration in which a display controller 43 superposes and displays a two-dimensional trace image based on first through n-th sets of volumetric data over a two-dimensional image (MPR image) based on volumetric data (m-th set of volumetric data). By the way, there may be no detailed description of the parts of the configuration that are the same as the first through fourth embodiments.

<System Configuration>

Figure 14:
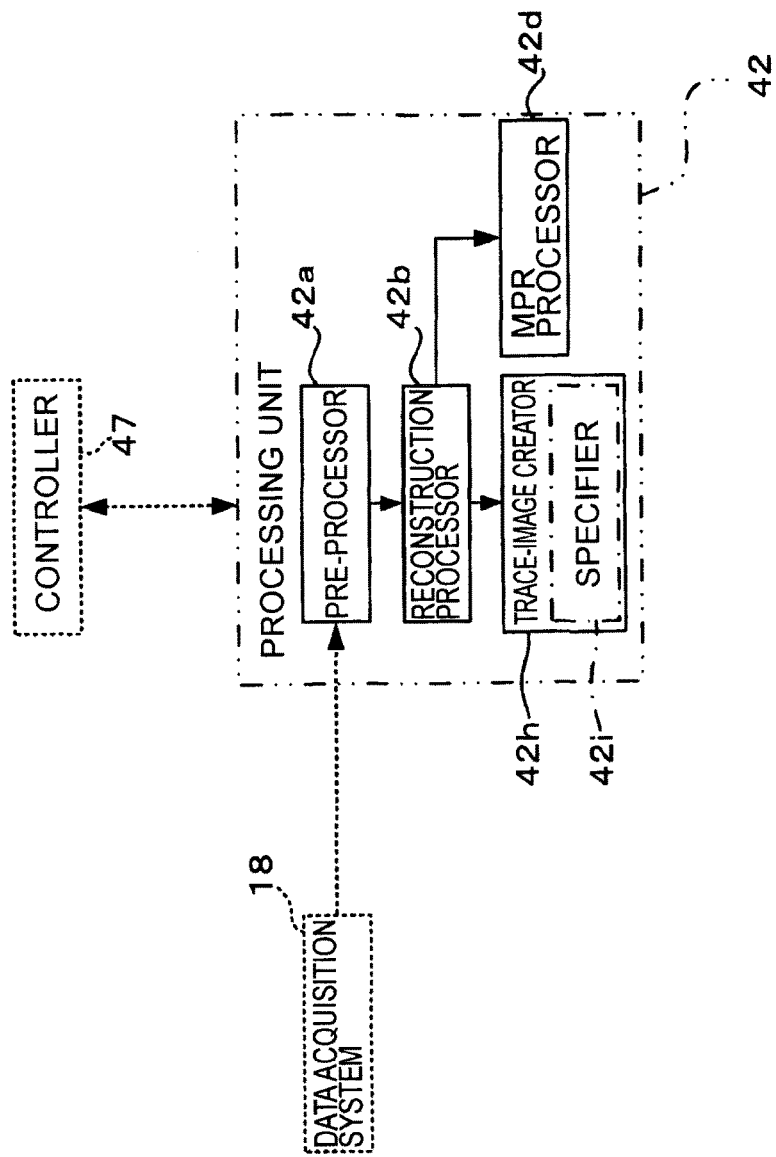
FIG. 14 is a block diagram showing the processing unit of an X-ray CT system as a fifth embodiment.
Figure 15:
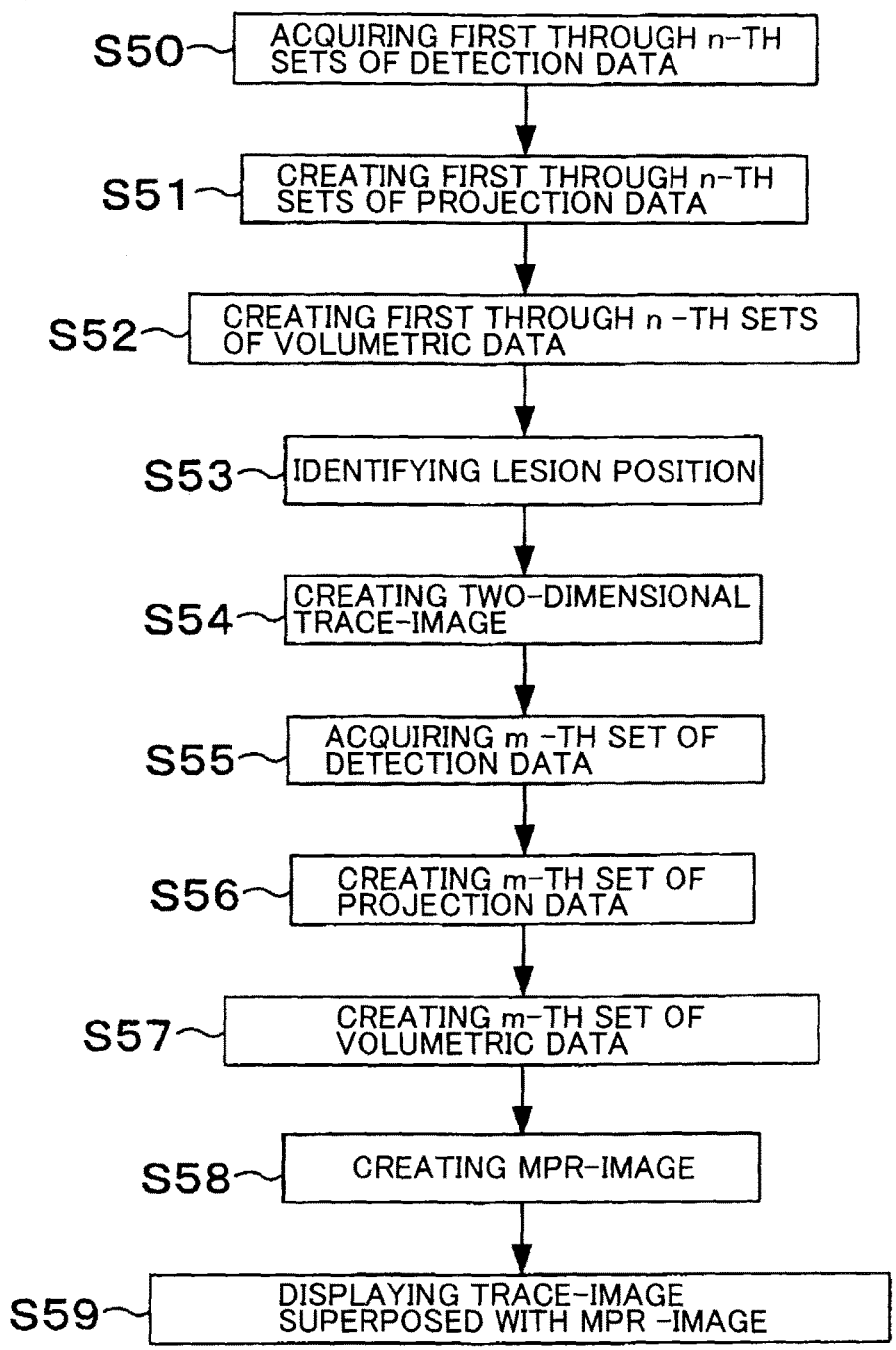
FIG. 15 is a flow chart showing an outline of actions taken by the X-ray CT system as a fifth embodiment.

FIG. 14 shows only the configuration of a processing unit 42 that is provided in the X-ray CT system 1 as this embodiment. The other parts of the configuration are the same as the first through fourth embodiments.

The trace-image creator 42h in this embodiment comprises a specifier 42i. Since the configuration of the specifier 42i is the same as the fourth embodiment, detailed description is not provided here.

The trace-image creator 42h creates a three-dimensional image that indicates a trace of a region undergoing a cyclic motion based on the positions of the region specified by the specifier 42i. The trace-image creator, then, creates as trace image a two-dimensional image that is a view of the three-dimensional image in a predetermined direction. For example, let's suppose that the specifier 42i has executed a predetermined image-processing on plural sets of volumetric data, and that the three-dimensional positions (coordinates) of a region undergoing a cyclic motion (e.g., lesion site) have been specified. The trace-image creator 42h, at first, creates a three-dimensional trace image by connecting the positions specified by the specifier 42i. Then, the trace-image creator 42h, by rendering the three-dimensional trace image in a predetermined direction, creates a two-dimensional trace image that is a view in the rendered direction.

The MPR processor 42d of this embodiment enables the displaying of an MPR image by rendering, in a given direction, the volumetric data generated by the reconstruction processor 42b (i.e., the MPR processor 42d creates an MPR image (two-dimensional image)). For example, the MPR processor 42d creates an MPR image by rendering, in a given direction, an m-th set of volumetric data, which is different from the first through n-th sets of volumetric data, which are a source to a three-dimensional trace image.

The display controller 43 superposes and displays the two-dimensional trace image over a two-dimensional image achieved by rendering a set of volumetric data, on the display unit 45. For example, the display controller 43 superposes a two-dimensional trace image created by the trace-image creator 42h over a two-dimensional image achieved by rendering the m-th set of volumetric data. The display controller 43 displays the two-dimensional image (MPR image) superposed with the trace image, on the display unit 45. By the way, if the two-dimensional trace image is superposed over the two-dimensional image based on the m-th set of volumetric data, then it is desirable that the rendering of the three-dimensional trace image and the rendering of the m-th set of volumetric data are done in the same direction.

<Actions>

Now, examples of action taken by the X-ray CT system 1 as this embodiment are described with reference to FIG. 15. Here, the description is made on a case of creating a trace image that indicates a trace of a lesion site P undergoing a cyclic motion. Furthermore, it is so conditioned that the volumetric data (first through n-th sets of volumetric data) on which a trace image is based and the volumetric data (m-th set of volumetric data) on which an image to be superposed with the trace image is based are, respectively, based on sets of detection data that are acquired at different timings.

At first, the X-ray CT system 1 executes scanning with X-rays by rotating the rotating body with a number of revolutions for a cycle of the respiration (first through n-th scanning revolutions) and generates a corresponding number of sets of volumetric data (first through n-th sets of volumetric data).

Specifically, the X-ray generator 11 radiates X-rays to the subject E. The X-ray detector 12 acquires detection data by detecting X-rays that have passed through the subject E (S50). In this embodiment, the X-ray detector 12 acquires first through n-th sets of detection data in the same way as the first through fourth embodiments. The preprocessor 42a executes preprocessing, for example, logarithmic transformation, on the first through n-th sets of detection data, which have been acquired at S50, and the preprocessor generates plural sets of projection data (first through n-th sets of projection data) (S51). The reconstruction processor 42b generates corresponding plural sets of volumetric data (first through n-th sets of volumetric data) based on the first through n-th sets of projection data, which have been generated at S51 (S52).

Then, the specifier 42i specifies positions (P1-Pn) of a lesion site P undergoing a cyclic motion in the respective first through n-th sets of volumetric data generated at S52 (S53). The trace-image creator 42h creates a three-dimensional image that shows a trace of the lesion by connecting the positions P1-Pn specified by the specifier 42i. Then, the trace-image creator 42h creates a two-dimensional trace image by rendering the three-dimensional image in a predetermined direction (S54). The created trace image is a two-dimensional image that shows a trace of the lesion site P. The trace image created at S54 is stored in the storage 44.

Next, the X-ray CT system 1 executes scanning with X-rays at a timing different from the timing applied to the scanning performed at S50 and acquires an m-th set of volumetric data.

Specifically, the X-ray generator 11 radiates X-rays to the subject E. The X-ray detector 12 acquires detection data by detecting X-rays that have passed through the subject E (S55). Here, the scanning is done for one revolution of the rotating body, and the detection data that correspond to this scanning session (m-th set of detection data) are acquired. The preprocessor 42a executes such preprocessing as logarithmic transformation on the acquired m-th set of detection data and generates a set of projection data (m-th set of projection data) (S56). The reconstruction processor 42b generates plural sets of tomographic data based on the m-th set of projection data, which has been generated at S56. Furthermore, the reconstruction processor 42b generates an m-th set of volumetric data by interpolating the plural sets of tomographic data (S57).

Then, the MPR processor 42d creates an MPR image by rendering the m-th set of volumetric data in the same direction as the rendering done at S54 (S58). In other words, the trace image created at S54 and the MPR image created at S58 are views in the same direction.

The display controller 43 superposes and displays the two-dimensional trace image created at S54 over the MPR image based on the m-th set of volumetric data created at S58, on the display unit 45 (S59).

<Operation and Effects>

Now, the operation and effects of the present embodiment are described.

The trace-image creator 42h of the X-ray CT system 1 as this embodiment comprises a specifier 42i, which specifies the position of a region undergoing a cyclic motion in each of the plural sets of volumetric data. The trace-image creator 42h creates a three-dimensional image that shows a trace of the region based on the specified positions of the region, and then, creates as trace image a two-dimensional image that is a view of the three-dimensional image in a predetermined direction. The display controller 43 superposes the two-dimensional trace image over a two-dimensional image based on volumetric data and displays them on the display unit 45.

In this way, the trace-image creator 42h creates a three-dimensional trace image that shows a trace of a cyclic motion in the subject E, on the basis of the three-dimensional positions of the region specified by the specifier 42i. Furthermore, the trace-image creator 42h creates a two-dimensional trace image from the three-dimensional trace image. Then, the display controller 43 superposes the two-dimensional trace image over a two-dimensional image based on volumetric data and displays them on the display unit 45. Thus, the range of the real motion of the region undergoing a cyclic motion can be easily recognized in the two-dimensional images. In other words, the X-ray CT system of this embodiment is capable of displaying medical images that reflect a cyclic motion in the subject.

(Sixth Embodiment)

Now, the configuration of an X-ray CT system 1 as a sixth embodiment is described with reference to FIG. 16 and FIG. 17. In the sixth embodiment, the trace-image creator 42h creates a two-dimensional trace image based on respective sets of MPR image data generated from plural sets of volumetric data (e.g., first through n-th sets of volumetric data). The configuration described here enables the display controller 43 to superpose the two-dimensional trace image over a two-dimensional image based on volumetric data (e.g., m-th set of volumetric data). By the way, there may be no detailed description of the parts of the configuration that are the same as the first through fifth embodiments.

<System Configuration>

Figure 16:
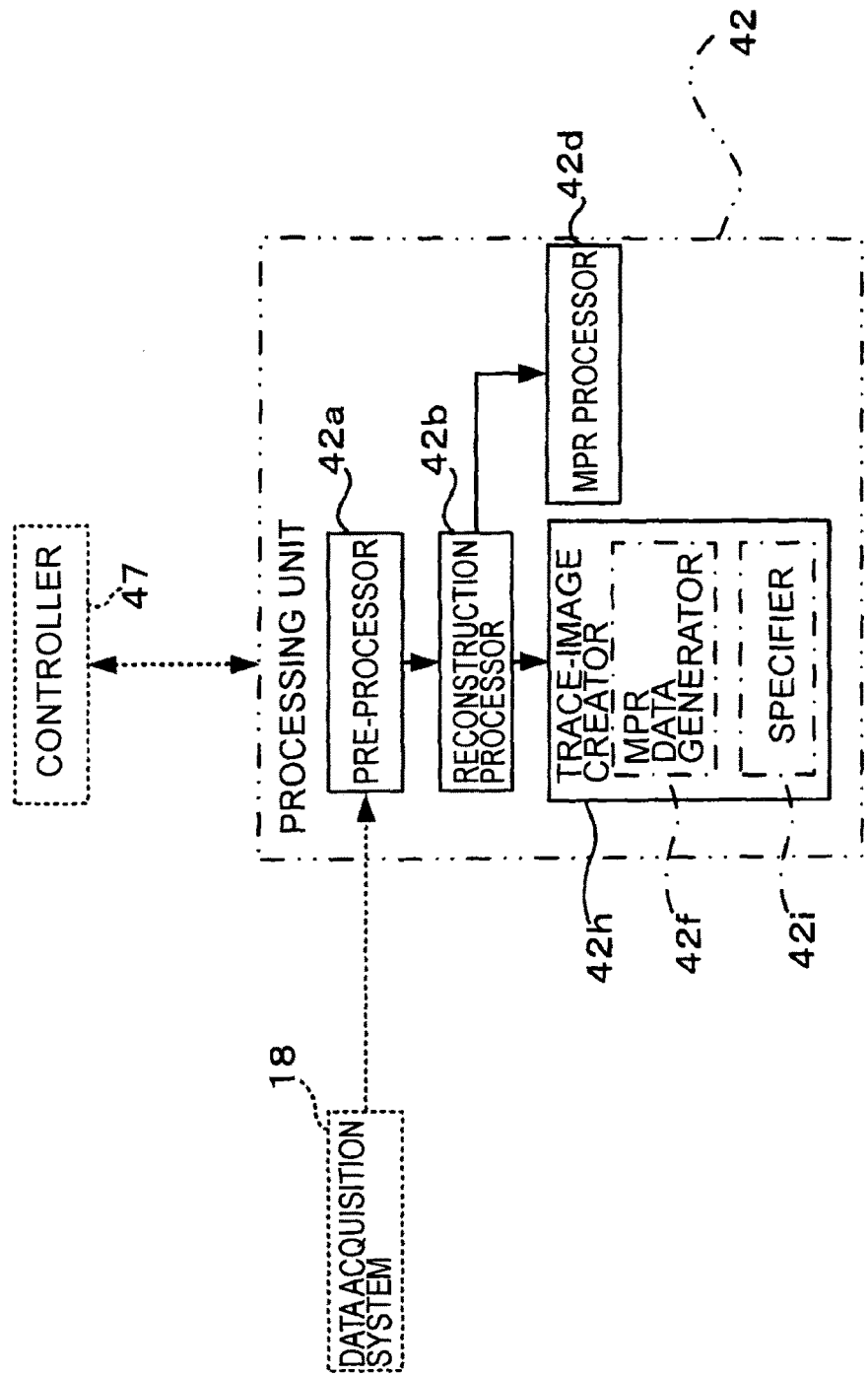
FIG. 16 is a block diagram showing the processing unit of an X-ray CT system as a sixth embodiment.
Figure 17:
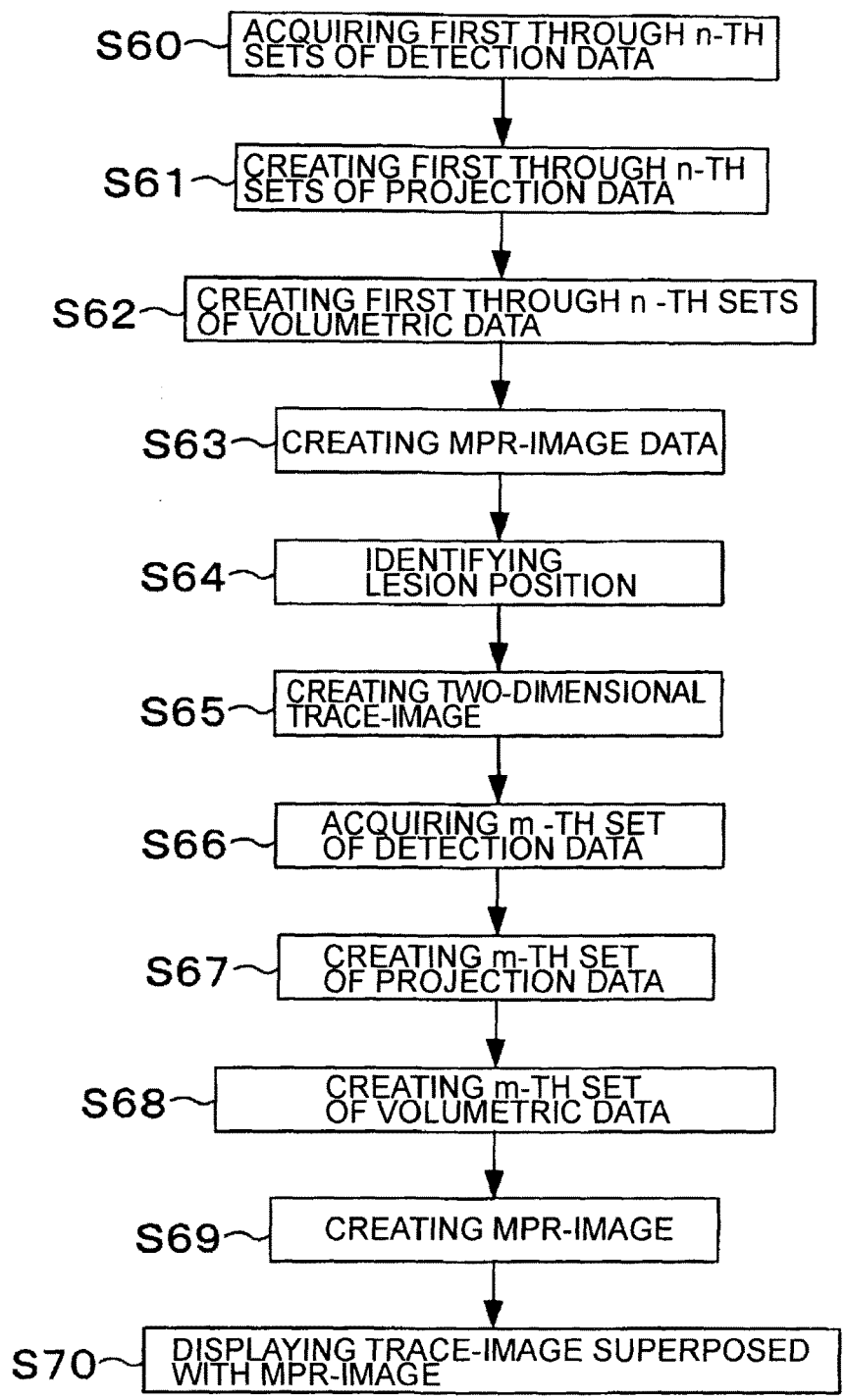
FIG. 17 is a flow chart showing an outline of actions taken by the X-ray CT system as a sixth embodiment.

FIG. 16 shows only the configuration of a processing unit 42 that is provided in the X-ray CT system 1 as this embodiment. The other parts of the configuration are the same as the first through fifth embodiments.

The trace-image creator 42h of this embodiment comprises an MPR data generator 42f and a specifier 42i. Since the configuration of the MPR data generator 42f is the same as the third embodiment, detailed description is not provided here.

The specifier 42i in this embodiment specifies the positions of a region undergoing a cyclic motion in the respective plural sets of MPR image data generated by the MPR data generator 42f. For example, let's suppose that the MPR data generator 42f has created first through n-th sets of MPR image data that show views in a predetermined sectional plane respectively through the first through n-th sets of volumetric data. The specifier 42i executes such image-processing as lesion-glowing or edge-detection on each of the first through n-th sets of MPR image data, and then, the specifier specifies two-dimensional positions (coordinates) of a region undergoing a cyclic motion (e.g., lesion site).

The trace-image creator 42h creates a two-dimensional trace image that shows a trace of the region on the basis of the positions specified by the specifier 42i. For example, let's suppose that the specifier 42i has specified two-dimensional positions (coordinates) of a region undergoing a cyclic motion (e.g., lesion site) in each of the first through n-th sets of MPR image data. The trace-image creator 42h creates a two-dimensional trace image by connecting the positions specified by the specifier 42i.

The display controller 43 superposes and displays the two-dimensional trace image over a two-dimensional image achieved by rendering volumetric data, on the display unit 45. For example, the display controller 43 superposes a two-dimensional trace image created by the trace-image creator 42h over a two-dimensional image achieved by rendering the m-th set of volumetric data. The display controller 43 displays the two-dimensional image superposed with the trace image, on the display unit 45. By the way, in a case where a two-dimensional trace image is superposed over the two-dimensional image based on the m-th set of volumetric data, it is desirable that the direction in which the rendering is executed through the first through n-th sets of volumetric data is the same direction as the rendering executed through the m-th set of volumetric data.

<Actions>

Now, examples of action taken by the X-ray CT system 1 as this embodiment are described with reference to FIG. 17. Here, the description is made on a case of creating a trace image that indicates a trace of a lesion site P undergoing a cyclic motion. Furthermore, it is so conditioned that the volumetric data (first through n-th sets of volumetric data) on which a trace image is based and the volumetric data (m-th set of volumetric data) on which an image to be superposed with the trace image is based are, respectively, based on sets of detection data that are acquired at different timings.

At first, the X-ray CT system 1 executes scanning with X-rays by rotating the rotating body with a number of revolutions for a cycle of the respiration (first through n-th scanning revolutions) and generates a corresponding number of sets of volumetric data (first through n-th sets of volumetric data).

Specifically, the X-ray generator 11 radiates X-rays to the subject E. The X-ray detector 12 acquires detection data by detecting X-rays that have passed through the subject E (S60). In this embodiment, the X-ray detector 12 acquires first through n-th sets of detection data in the same way as the first through fourth embodiments. The preprocessor 42a executes preprocessing, for example, logarithmic transformation, on the first through n-th sets of detection data, which have been acquired at S60, and the preprocessor generates plural sets of projection data (first through n-th sets of projection data) (S61). The reconstruction processor 42b generates corresponding plural sets of volumetric data (first through n-th sets of volumetric data) based on the first through n-th sets of projection data, which have been generated at S61 (S62).

Then, the MPR data generator 42f generates first through n-th sets of MPR image data that correspond, respectively, to the first through n-th sets of volumetric data, by rendering in the same direction each of the first through n-th sets of volumetric data (S63). The specifier 42i specifies positions (P1-Pn) of a lesion site P undergoing a cyclic motion in each of the first through n-th sets of MPR image data, which have been generated at S63 (S64). The trace-image creator 42h creates a two-dimensional image that shows a trace of the lesion site by connecting the positions P1-Pn specified by the specifier 42i (S65). The created trace image is a two-dimensional image that shows a trace of the lesion site P. The trace image created at S65 is stored in the storage 44.

Next, the X-ray CT system 1 executes scanning with X-rays at a timing different from the timing applied to the scanning performed at S60 and acquires an m-th set of volumetric data.

Specifically, the X-ray generator 11 radiates X-rays to the subject E. The X-ray detector 12 acquires detection data by detecting X-rays that have passed through the subject E (S66). Here, the scanning is done for one revolution of the rotating body, and the detection data that correspond to this scanning session (m-th set of detection data) are acquired.

The preprocessor 42a executes such preprocessing as logarithmic transformation on the acquired m-th set of detection data and generates a set of projection data (m-th set of projection data) (S67). The reconstruction processor 42b generates plural sets of tomographic data based on the m-th set of projection data, which has been generated at S67. Furthermore, the reconstruction processor 42b generates an m-th set of volumetric data by interpolating the plural sets of tomographic data (S68).

Then, the MPR processor 42d creates an MPR image by rendering the m-th set of volumetric data in the same direction as the rendering done at S68 (S69). In other words, the trace image created at S65 and the MPR image created at S69 are views in the same direction.

The display controller 43 superposes the two-dimensional trace image created at S65 over the MPR image created at S69 and displays them on the display unit 45 (S70).

<Operation and Effects>

Now, the operation and effects of the present embodiment are described.

The trace-image creator 42h of the X-ray CT system 1 in this embodiment comprises an MPR data generator 42f and a specifier 42i. The MPR data generator 42f creates plural sets of MPR image data each set representing a view in a predetermined sectional plane through a corresponding set of the plural sets of volumetric data. The specifier 42i specifies the position of a region undergoing a cyclic motion in each of the plural sets of MPR image data. The trace-image creator 42h creates a two-dimensional trace image on the basis of the specified positions of the region. The display controller 43 superposes the two-dimensional trace image over a two-dimensional image based on volumetric data and displays them on the display unit 45.

In this way, the trace-image creator 42h creates a two-dimensional trace image that shows a trace of a cyclic motion in the subject E, on the basis of the two-dimensional positions of the region specified by the specifier 42i. As a result, the display controller 43 superposes the trace image over a two-dimensional image based on volumetric data and displays them on the display unit 45. Thus, the range of the real motion of the region undergoing a cyclic motion can be easily recognized in the two-dimensional images. In other words, the X-ray CT system of this embodiment is capable of displaying medical images that reflect a cyclic motion in the subject.

(Variant Embodiment from the Fourth Through Sixth Embodiment)

In a case where an image based on volumetric data and a trace image are superposed one over the other, it is desirable that these images be displayed distinctively from each other. This variant embodiment is described as an X-ray CT system that is capable of changing displaying conditions applied to the image based on volumetric data and to the trace image.

Figure 18:
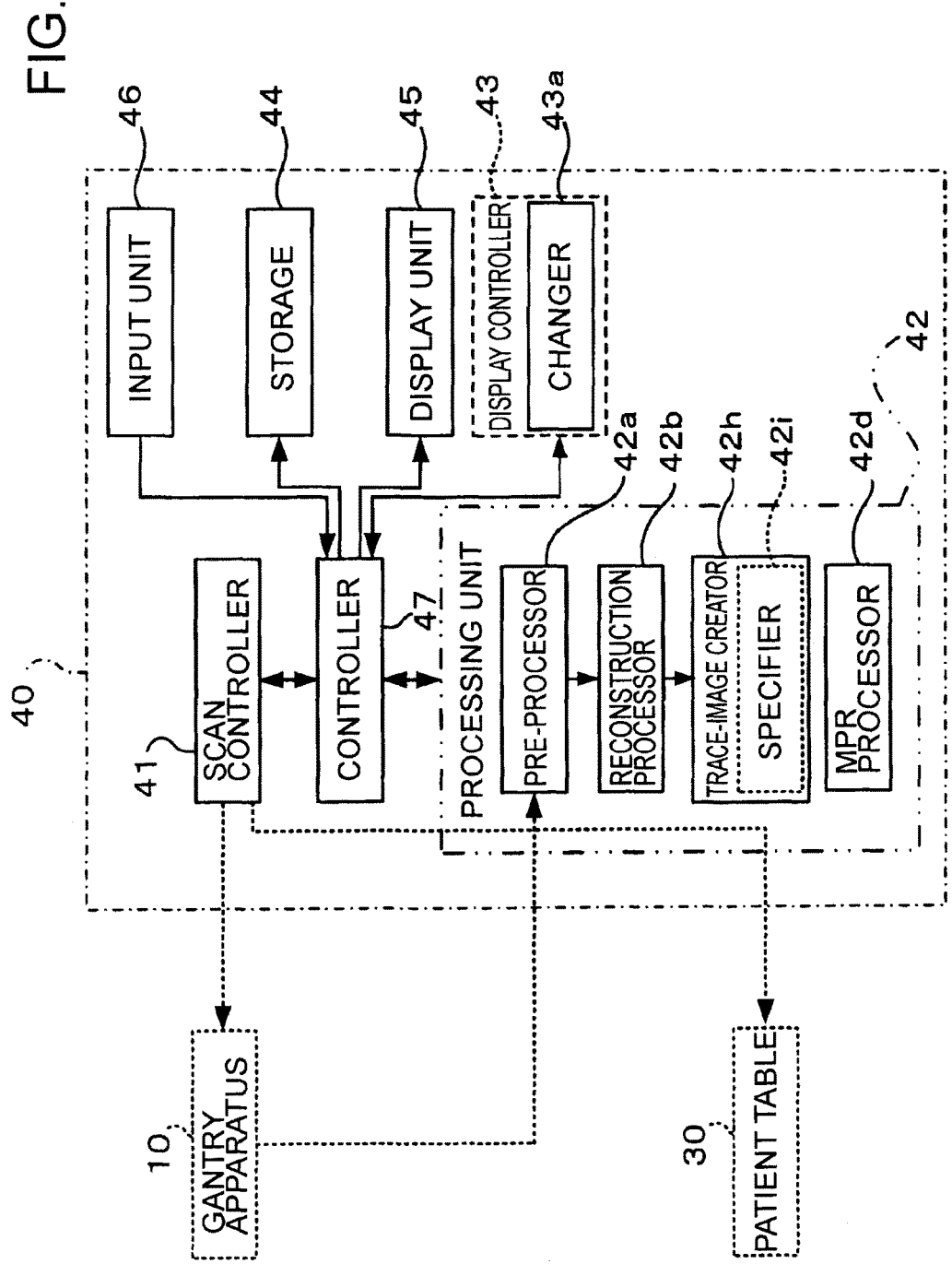
FIG. 18 is a block diagram showing the console device of an X-ray CT system as a variant embodiment of the fourth through sixth embodiments.

FIG. 18 is a block diagram showing the configuration of a console device 40 provided in the X-ray CT system 1 as this variant embodiment. The display controller 43 of the X-ray CT system 1 is configured to include a changer 43a, which changes the displaying conditions that are applied to the image based on volumetric data and to the trace image. Specifically, the changer 43a changes at least one of the following conditions: colors used for the images (trace image), transparency, and CT values. For example, the changer 43a so changes the conditions that the image based on volumetric data is displayed in grayscale while the trace image is displayed in color. If the images are displayed in differing colors in such a way, then the region undergoing a cyclic motion is made readily recognizable in the images.

Instead, the changer 43a can raise the transparency of the image based on volumetric data and lower the transparency of the trace image. If the trace image is displayed at a lowered transparency, then the region undergoing a cyclic motion can be enhanced in the images. By the way, although the configuration shown in FIG. 18 is based on the configuration of the fourth embodiment, it is also possible to provide such a changer 43a in the configuration of the fifth embodiment or the sixth embodiment.

Figure 19:
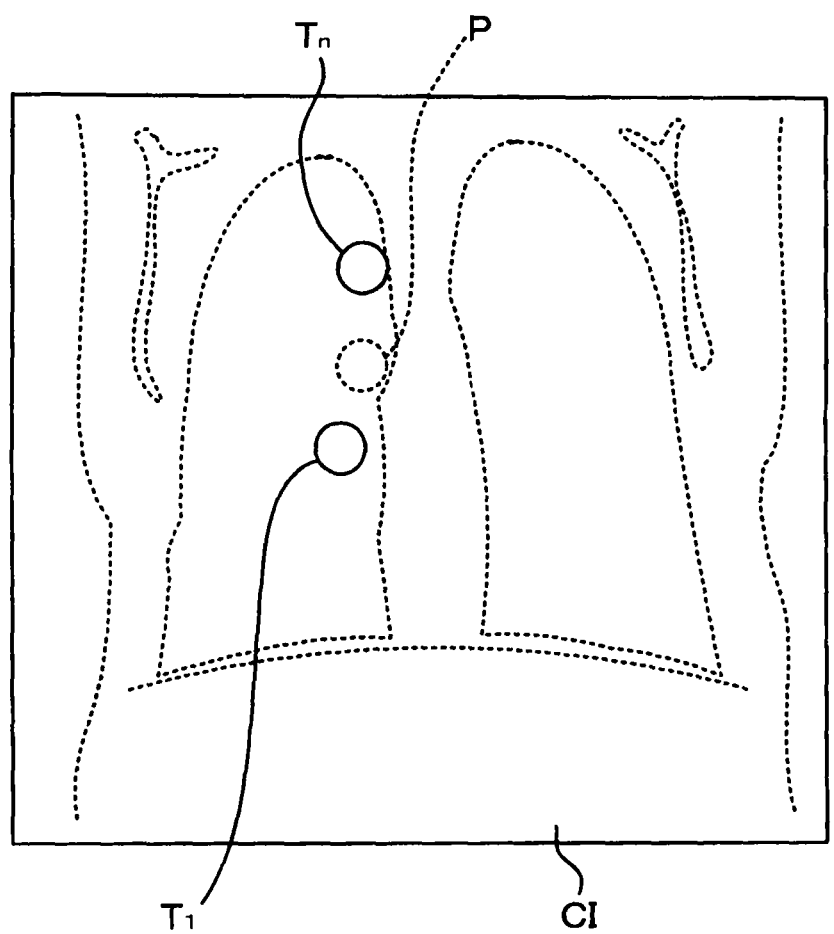
FIG. 19 is a drawing showing images that are displayed on a display unit according to the variant embodiment of the fourth through sixth embodiments.

Furthermore, the changer 43a can change the displaying conditions so as to show only part of the trace image, which is superposed. FIG. 19 shows an MPR image (coronal image CI) acquired by rendering, in the coronal direction, a three-dimensional image that has been superposed with a three-dimensional trace image. Let's suppose that the changer 43a has changed the displaying conditions so as to show only the positions of the trace image whose displacement is at the maximum in the cyclic motion of a lesion site P. As a result, the display controller 43 displays only the parts (T1 and Tn) of the trace image that are at the maximum in displacement in the cyclic motion of a lesion site P. Even if only parts of a trace image are displayed in this way, a cyclic motion in the subject is still roughly recognizable. Furthermore, in a case where a cyclic motion being observed is complex, the superposition of the trace image over an MPR image, etc. may make the images as a whole hard to recognize. In such a case, by showing only part of the trace image, the region undergoing a cyclic motion can be made recognizable with the image being kept displayed in clarity.

<Effects Common Throughout the First Through Sixth Embodiments>

According to the X-ray CT system presented as at least one of the embodiments described above, an image (in two dimensions or in three dimensions) based on volumetric data is superposed and displayed with a moving image or a trace image (in two dimensions or in three dimensions). As a result, the actual motion of or a trace of a region undergoing a cyclic motion is made easily recognizable in the images. In other words, an X-ray CT system according to any of the embodiments is capable of displaying medical images that reflect a cyclic motion in the subject.

(Seventh Embodiment)

In diagnostic imaging, a plurality of MPR images are aligned with one another or switched one after another in display. In such a case, it is desirable that the subject in the MPR images be presented at the same position, in the same direction, and at the same magnification in picture frames. In addition, the user may arbitrarily modify the position, direction and magnification applied for projecting the subject in a picture frame. In such a case, in prior-art technologies, the position, direction and magnification applied for projecting the subject had to be modified for each of the MPR images. This was a very troublesome operation and was an obstacle to image-browsing work.

In addition, the body position taken by the subject for scanning varies depending on which region to be scanned or on what manual technique to be applied, but in prior-art technologies, MPR images were displayed all in the same direction. Specifically, the body positions taken around the body axis include supine position, prone position, lateral decubitus position (rightward or leftward) while the body positions taken along the rostrocaudal axis include position with the head of the subject toward the gantry and position with the feet toward the gantry. Notwithstanding such various body positions applied for scanning, the MPR images were always displayed under the following conditions: axial images are displayed such that the abdomen is positioned to the upper side of the display screen while the back of the subject is positioned to the lower side; sagittal images are displayed such that the front of the subject is positioned to the left side of the display screen while the back is positioned to the right side; and coronal images are displayed such that the front of the subject is shown forward in the screen while the back is shown farther away. Such displaying conditions do not cause any particular inconvenience in simple image browsing. However, for example, in a case where puncturing is performed for a biopsy, divergence can occur between the direction of the subject actually seen (i.e., the direction of the subject in real space) and the direction of the subject being displayed in images. This divergence was an obstacle to and interfered in the smooth execution of such procedures.

The objective of the present embodiment is to provide an X-ray CT system that is capable of facilitating the execution of such work as mentioned above by automatically modifying the conditions applied for projecting the subject in MPR images.

<System Configuration>

Figure 20:
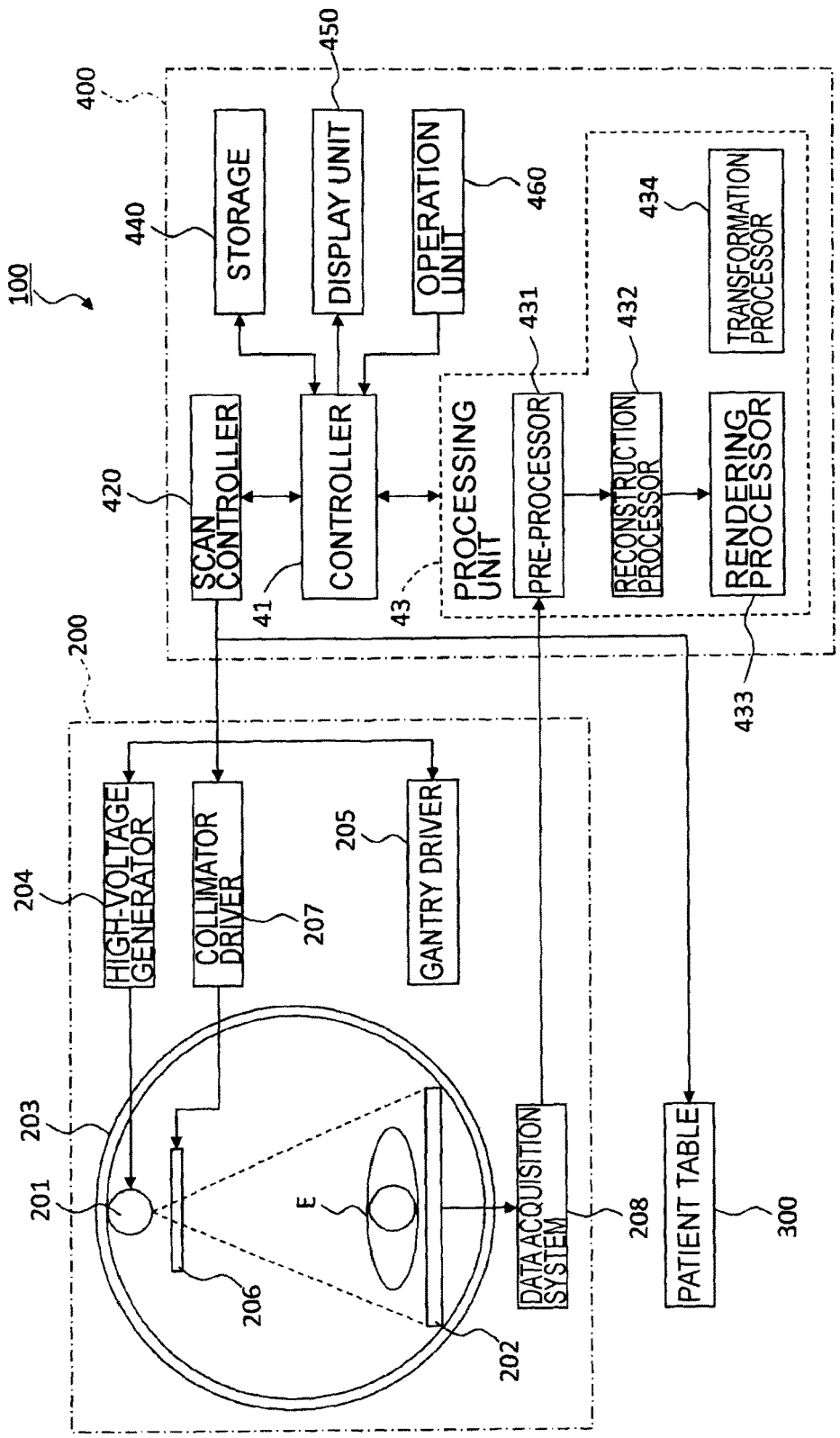
FIG. 20 is a block diagram showing the configuration of an X-ray CT system as a seventh embodiment.
Figure 21:
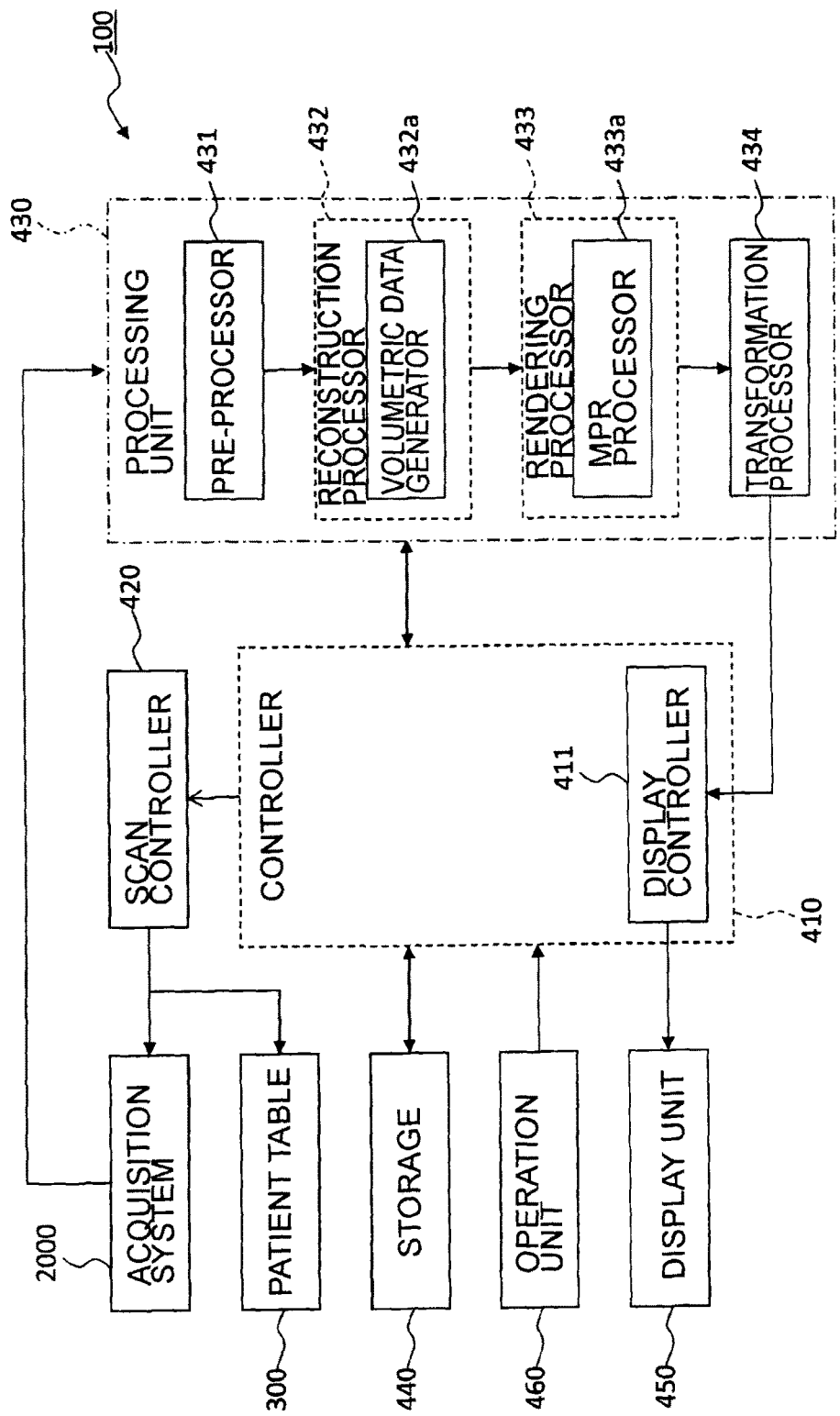
FIG. 21 is another block diagram showing the configuration of the X-ray CT system as a seventh embodiment.

In this embodiment, the description concerns an example of executing affine transformation for constant magnification or an example of executing the same affine transformation on plural sets of MPR image data. FIG. 20 and FIG. 21 show an exemplary configuration of the X-ray CT system as this embodiment. The terms "image" and "image data" may be used interchangeably in the following description.

The X-ray CT system 100 is configured to include a gantry apparatus 200, a patient table 300, and a console device 400.

[Gantry Apparatus]

The gantry apparatus 200 is a piece of equipment that irradiates the subject E with X-rays and gathers detection data of X-rays that have passed through the subject E. The gantry apparatus 200 comprises an X-ray generator 201, an X-ray detector 202, a rotating body 203, a high voltage generator 204, a gantry drive 205, a collimator 206, a collimator drive 207, and a data acquisition system 208.

The X-ray generator 201 is configured to include an X-ray tube, which generates X-rays (e.g., a vacuum tube that generates beams in circular cone or in pyramid-shape, not shown). X-rays being generated are used for irradiating the subject E.

The X-ray detector 202 is configured to include a plurality of X-ray detector elements (not shown). The X-ray detector 202 detects X-ray intensity distribution data (detection data) that indicate an intensity distribution of X-rays that have passed through the subject E by using the X-ray detector elements, and the X-ray detector outputs the detection data in current signals.

The X-ray detector 202 comprises a two-dimensional X-ray detector (area detector) in which, for example, a plurality of detector elements are disposed, respectively, in two inter-orthogonal directions (slicing direction and channeling direction). A plurality of X-ray detector elements are aligned, for example, in 320 lines in slicing direction. The use of an X-ray detector having such a multi-line configuration enables the scanning of a three-dimensional region, which has a width in slicing direction, per scanning rotation (volumetric scanning). By the way, the slicing direction corresponds to the rostrocaudal direction of the subject E while the channeling direction corresponds to the rotational direction of the X-ray generator 201.

The rotating body 203 is a member that supports both the X-ray generator 201 and the X-ray detector 202 facing each other, with the subject E to be placed between them. The rotating body 203 has a through-opening in the slicing direction. Into this opening, a top plate mounted with the subject E is inserted. The rotating body 203 is rotated by the gantry drive 205, in a circular orbit around the subject E as center.

The high voltage generator 204 supplies high voltage to the X-ray generator 201, and the X-ray generator 201 generates X-rays on the high voltage. The collimator 206 forms a slit (opening) for adjusting the fan angle (flare angle in the channeling direction) and the cone angle (flare angle in the slicing direction) of the X-rays output from the X-ray generator 201. The collimator drive 207 drives the collimator 206 to change the size and shape of the slit.

The data acquisition system 208 (DAS) gathers detection data from the X-ray detector 202 (from each of the X-ray detector elements). Furthermore, the data acquisition system 208 converts the detection data gathered (in current signals) into voltage signals, integrates them periodically for amplification, and then converts them into digital signals. Then, the data acquisition system 208 sends the detection data that have been converted into digital signals to the console device 400.

The acquisition system 2000 shown in FIG. 21 is configured to include at least a gantry apparatus 200. If the subject needs to be moved during the scanning (i.e., during the data gathering), for example, for helical scanning, then the acquisition system 2000 should include a patient table 300.

[Patient Table]

The subject E is placed on the top plate (not shown) of the patient table 300, and the patient table 300 moves the subject E mounted on the top plate in the rostrocaudal direction. The patient table 300 moves the top plate also in the up and down direction.

[Console Device]

The console device 400 is used for operational inputs to the X-ray CT system 100. In addition, the console device 400 is configured to reconstruct CT image data (tomographic data and volumetric data), which show internal structures in the subject E, on the basis of the detection data acquired by the gantry apparatus 200. The console device 400 is configured to include a control unit 410, a scanning-control unit 420, a processing unit 430, a storage 440, a display unit 450, and an operation unit 460.

The control unit 410, the scanning-control unit 420 and the processing unit 430 are configured to include, for example, processors and storage devices. For the processors, for example, CPUs, GPUs or ASICs are used, and the storage devices comprise, for example, ROM, RAM, and HDDs. The storage devices store computer programs, which are compiled for execution of the functions of all parts of the X-ray CT system 100. The processors are to execute these computer programs for realization of the functions, and the control unit 410 controls every aspect of the system. For example, the control unit 410 comprises a display controller 411, which controls the display unit 450 to display information (refer to FIG. 21).

The scanning-control unit 420 controls integrally all actions of scanning with X-rays. This integrated control involves controlling the high voltage generator 204, the gantry drive 205, the collimator drive 207, and the patient table 300. The control of the high voltage generator 204 involves controlling the high voltage generator 204 to apply a predetermined high voltage to the X-ray generator 201 at a predetermined timing. The control of the gantry drive 205 involves controlling the gantry drive 205 to drive the rotating body 203 to rotate at a predetermined timing and at a predetermined velocity. The control of the collimator drive 207 involves controlling the collimator drive 207 to drive the collimator 206 so as to form a slit in a predetermined size and in a predetermined shape. The control of the patient table 300 involves controlling the patient table 300 to move the top plate to a predetermined position at a predetermined timing. By the way, in volumetric scanning, scanning is performed in the state where the position of the top plate is fixed. In helical scanning, however, scanning is performed while the top plate is being moved.

The processing unit 430 executes various types of processing on the detection data, which have been received from the gantry apparatus 200 (data acquisition system 208). The processing unit 430 is configured to include a preprocessor 431, a reconstruction processor 432, a rendering processor 433, and a conversion processor 434.

The preprocessor 431 executes such preprocessing as logarithmic transformation, offset correction, sensitivity correction, and beam-hardening correction on the detection data, which have been received from the gantry apparatus 200, and the preprocessor generates projection data.

The reconstruction processor 432 generates CT image data (tomographic data and volumetric data) on the basis of the projection data generated by the preprocessor 431. As reconstruction-processing for tomographic data, such methods as two-dimensional Fourier transformation and convolution-back-projection can be applied arbitrarily. Volumetric data are generated by interpolating plural sets of tomographic data that have been reconstructed. For volumetric data reconstruction, such methods as cone-beam reconstruction, multi-slice reconstruction, and magnified reconstruction can be employed arbitrarily. Volumetric scanning executed with the above-mentioned multi-line X-ray detector elements enables reconstruction of volumetric data that cover a wide range. Processing for generating volumetric data is executed by a volumetric data generator 432a, which is shown in FIG. 21.

The rendering processor 433 can execute, for example, MPR processing and volume rendering. MPR processing is an image-rendering method for generating MPR image data that represent a view in a particular sectional plane through volumetric data, and it is used here for creating a view in a sectional plane that is arbitrarily set through the volumetric data generated by the volumetric data generator 432a. MPR processing is executed by an MPR processor 433a, which is shown in FIG. 21. Volume rendering is an image-processing method for generating pseudo-three-dimensional image data by sampling volumetric data along an arbitrary eyeline (ray) and by adding the values (CT values) of the sampled data, and it is used here for creating three-dimensional image data that represent a three-dimensional region in the subject E.

The conversion processor 434 executes affine transformation on the MPR image data generated by the MPR processor 433a. The conversion processor 434 executes a similar affine transformation on each set of MPR image data particularly in the case where sets of MPR image data are generated one after another. The term "similar affine transformation" includes not only identical affine transformations but also affine transformations that are only partially identical in characteristics. Here, the word "characteristics" means the effects that the affine transformation produces on the object. Specifically, since affine transformations are such coordinate transformations as parallel displacement, rotational transfer, magnification modification, and inversion (or mirror image), which are executed on the object, the characteristics include amount of parallel displacement, amount of rotational transfer, rate of magnification, direction of inversion, etc. Examples of such affine transformations are described in the following:

A first example to be described is a case where an affine transformation for constant magnification is executed on plural sets of MPR image data. The affine transformation can be expressed, for example, as a matrix, and the storage 440 stores information that indicates a preset magnification for the affine transformation (magnification information). Magnification information may be expressed in a matrix that represents, for example, an affine transformation. It may be the absolute value of the determinant of the matrix (magnification of the area or the volume), or it may be a magnification applied to each of the direction (e.g., x direction, y direction (and z direction)). The affine transformation here is set arbitrarily, for example, by the user. The followings are examples of method for setting up an affine transformation: setting up an affine transformation by specifying the elements of the matrix; setting up an affine transformation by specifying the above-mentioned characteristics individually; and setting up an affine transformation by actually transferring, rotating, and inverting the image manually. These methods are applied by using the operation unit 460 (and the display unit 450). Furthermore, the affine transformation to be set up may be two-dimensional or three-dimensional. If a two-dimensional affine transformation is set up, then, of course, it can be applied not only to the set of MPR image data for which the affine transformation is intended but also to other sets of MPR image data that share the same sectional plane. Moreover, for example, if this two-dimensional affine transformation is embedded in a three-dimensional affine transformation, which deals with volumetric data, then the resultant affine transformation can be applied as an affine transformation to other sets of MPR image data that do not share the same sectional plane as well as to volumetric data. In addition, if a three-dimensional affine transformation is set up, then it can be applied to volumetric data and to MPR image data that represent an arbitrary section.

After new MPR image data are generated by the MPR processor 433a, the conversion processor 434 executes a new affine transformation on the new MPR image data, the affine transformation being magnification or reduction at the rate of magnification that is specified in the magnification information stored in the storage 440. This process automatically generates and displays MPR images at the same magnification.

A second example is a case where an affine transformation for constant transformation is executed on plural sets of MPR image data. The storage 440 stores information that indicates a preset affine transformation (affine transformation information). The affine transformation information is, for example, a matrix that represents an affine transformation itself. By the way, the matrix that represents an affine transformation actually includes the magnification information discussed for the first example (i.e., magnification can be calculated from the matrix). After new MPR image data are generated by the MPR processor 433a, the conversion processor 434 executes a new affine transformation on the new MPR image data, the affine transformation being in accordance with the affine transformation information stored in the storage 440. This process automatically generates and displays MPR images that have been processed through the same constant transformation. The term "same constant transformation" means that the above-mentioned characteristics of affine transformation are constantly applied in the same way to the transformation-processing executed on all sets of MPR image data.

By the way, here, only two examples have been discussed. However, another affine transformation with some of the above-mentioned characteristics may be executed on plural sets of MPR image data, or another affine transformation with an arbitrary combination of the above-mentioned characteristics may be executed on plural sets of MPR image data. Furthermore, two or more affine transformations may be applied selectively.

The storage 440 stores the above-mentioned magnification information and affine transformation information. In addition, the storage 440 stores detection data, projection data, reconstructed image data, etc. The display unit 450 comprises a displaying device such as an LCD. The operation unit 460 is used for inputting various instructions and information to the X-ray CT system 100. The operation unit 460 comprises, for example, a key-board, a mouse, a track ball, a joystick, etc. In addition, the operation unit 460 may include the GUI used for the display unit 450.

<Actions>

Figure 22:
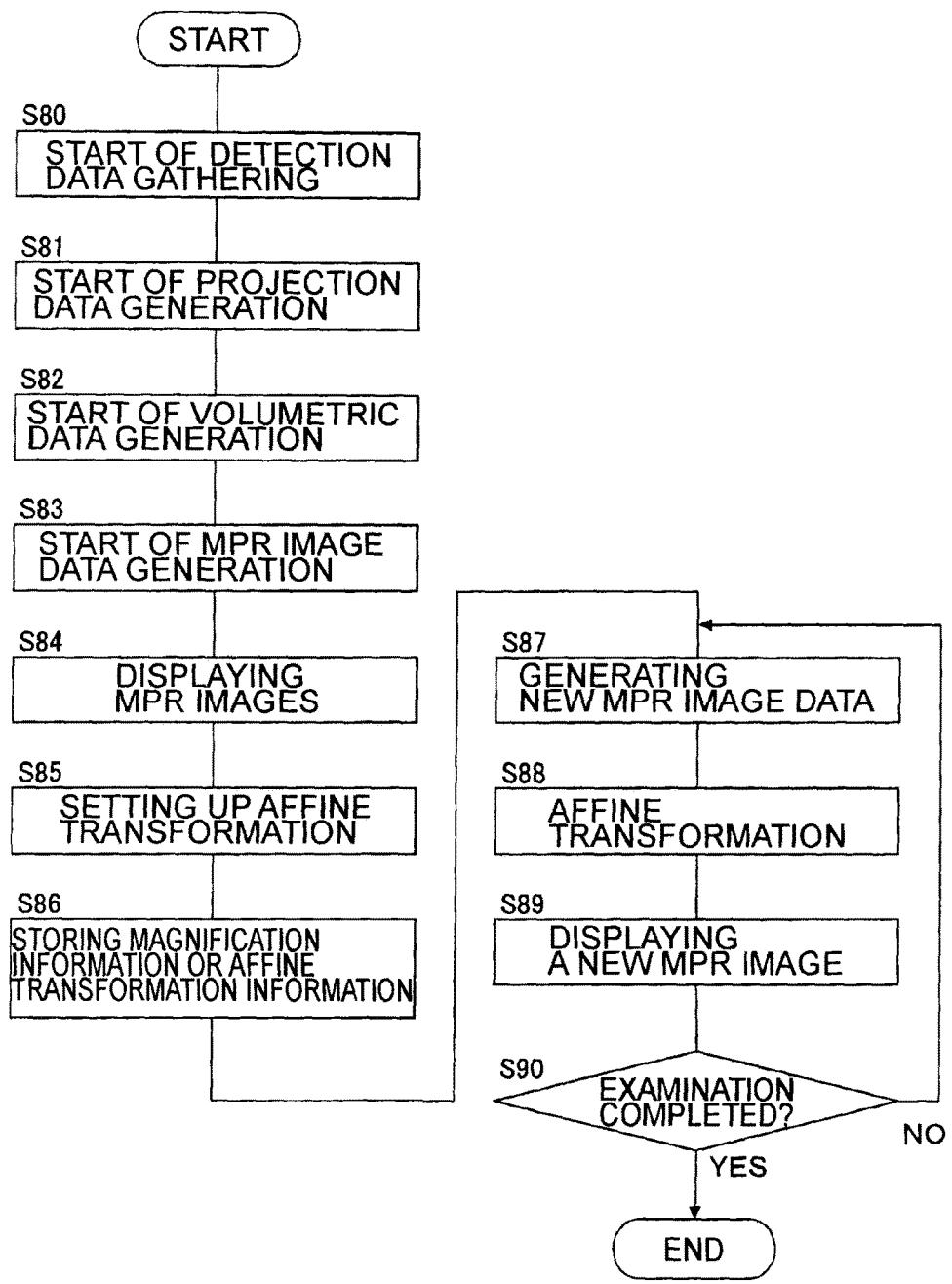
FIG. 22 is a flow chart showing exemplary actions taken by the X-ray CT system as a seventh embodiment.

Now, actions taken by the X-ray CT system 100 as this embodiment are described. FIG. 22 shows exemplary actions taken by the X-ray CT system 100.

(S80: Start of Detection Data Gathering)

At first, a subject E is placed on the top plate of the patient table 300 and inserted into the through-opening of the gantry apparatus 200. When a predetermined scanning-initiation operation is made, the control unit 410 sends control signals to the scanning-control unit 420. The scanning-control unit 420, upon receiving the control signals, controls the high voltage generator 204, the gantry drive 205, and the collimator drive 207 to irradiate the subject E with X-rays for scanning. The X-ray detector 202 detects X-rays that have passed through the subject E. The data acquisition system 208 gathers detection data being generated by the X-ray detector 202 during the scanning. The data acquisition system 208 sends the gathered detection data to the preprocessor 431.

(S81: Start of Projection Data Generation)

The preprocessor 431 executes the above-described preprocessing on the detection data, which have been received from the data acquisition system 208, and the preprocessor generates projection data.

(S82: Start of Volumetric Data Generation)

The reconstruction processor 432 executes reconstruction-processing on the projection data, which have been generated by the preprocessor 431, and the reconstruction processor generates plural sets of tomographic data. Furthermore, the volumetric data generator 432a generates volumetric data based on the sets of tomographic data.

(S83: Start of MPR Image Data Generation)

The MPR processor 433a generates MPR image data based on the volumetric data, which have been generated by the volumetric data generator 432a. The MPR image data may be any set of image data that represents a view along any of the three-orthogonal axes or a set of image data that represents an oblique view in an arbitrarily set sectional plane.

(S84: Displaying MPR Images)

The display controller 411 displays an MPR image based on the MPR image data, which have been generated by the MPR processor 433a, on the display unit 450.

At this stage, for the purpose of minimizing the radiation dose of the subject E, detection data gathering, projection data generation, volumetric data generation, and MPR image data generation can be stopped temporarily. In this case, these processes can be restarted at an arbitrary timing before step 87.

(S85: Setting Up Affine Transformation)

The user sets up an affine transformation based on the displayed MPR image. As a specific example of this processing, the user processes the displayed MPR image by using the operation unit 460. This "processing" comprises at least one of rotational transfer, parallel displacement, magnification modification, and inversion (i.e., affine transformation). The processing unit 430 creates an affine transformation that corresponds to the processing contents and generates magnification information or affine transformation information based on this affine transformation.

(S86: Storing Magnification Information or Affine Transformation Information)

The control unit 410 stores the magnification information or affine transformation information, which has been generated by the processing unit 430, in the storage 440.

(S87: Generating New MPR Image Data)

The MPR processor 433a generates new MPR image data. This set of MPR image data may be based on the volumetric data that have been generated at step 82 or may be based on the volumetric data that have been acquired by newly executing detection data gathering, projection data generation, and volumetric data generation.

(S88: Affine Transformation)

The conversion processor 434 executes an affine transformation based on the magnification information or affine transformation information stored in the storage 440 at step 86 on the new MPR image data, which has been generated at step 87.

Now, this process is described more specifically. If magnification information is stored at step 86, then, the conversion processor 434 executes an affine transformation on the new MPR image data, the affine transformation being magnification or reduction at the rate of magnification that is specified in the magnification information. This case of affine transformation concerns only that at least magnification should be the same throughout the sets of MPR image data, and therefore, such characteristics as amount of rotational transfer, amount of parallel displacement, and direction of inversion are optional. The affine transformation is determined by the conversion processor 434 on the basis of the magnification information (and other conditions). In this case, the affine transformation can be determined by analyzing MPR image data that are targeted for the affine transformation and by basing the determination on the analysis results. Such analysis processing involves specifying the position of the subject projected as image and/or the direction of the subject projected as image, and based on the projected position, the amount of parallel displacement is calculated, and based on the projected direction, the amount of rotational transfer is calculated. Then, the affine transformation is determined on the basis of the amount of parallel displacement, the amount of rotational transfer and the stored magnification information.

If the affine transformation information is stored at step 86, then, the conversion processor 434 executes the affine transformation based on this affine transformation information (i.e., the affine transformation that has been set up at step 85) on the new MPR image data.

(S89: Displaying a New MPR Image)

The display controller 411 displays an MPR image based on the new MPR image data on which the affine transformation has been executed at step 88, on the display unit 450. At this instant, the display controller 411 can display the new MPR image, which is based on the new MPR image data, at the same display resolution as the MPR image that was displayed at step 84. Since the MPR images before and after the affine transformation are displayed at the same resolution in this way, this can work as prevention against misinterpretation of the size of the projected object. For example, in a puncturing operation, prevention is made against misunderstanding the length of the puncture needle shown in the MPR image.

(S90: Examination Completed?)

If an instruction of examination completion is given at this stage (S90: YES), then the process of exemplary actions comes to completion. On the other hand, if the examination is continued (S90: NO), then steps 87-89 are repeated until an instruction of examination completion is given at step 90.

By the way, the affine transformation can be modified at any arbitrary stage while steps 87-89 are being repeated. If such modification is desired, then steps 85-86 are executed again so that new magnification information or affine transformation information is defined and stored in the storage 440, and the process of steps 87-89 is performed on the basis of the new magnification information or affine transformation information.

<Operation and Effects>

Now, the operation and effects of the X-ray CT system 100 as this embodiment are described.

The X-ray CT system 100 comprises a patient table 300, an acquisition system 2000, a volumetric data generator 432*a*, an MPR processor 433*a*, a conversion processor 434, a display unit 450, and a display controller 411. The acquisition system 2000 scans the subject E mounted on the patient table 300 with X-rays and gathers data. The volumetric data generator 432*a* generates volumetric data based on the data gathered by the acquisition system 2000. The MPR processor 433*a* executes MPR processing on the volumetric data, which have been generated by the volumetric data generator 432*a*, and generates MPR image data that represent a view in a predetermined sectional plane. The conversion processor 434 executes an affine transformation on the MPR image data, which have been generated by the MPR processor 433*a*. The display controller 411 displays an MPR image based on the MPR image data on which the affine transformation has been executed by the conversion processor 434, on the display unit 450.

According to such an X-ray CT system 100, MPR image data are processed with affine transformation. Thus, it is possible to facilitate the smooth execution of the operation by automatically modifying the conditions applied for projecting the subject in MPR images.

In addition, the X-ray CT system 100 comprises a storage 440, which stores magnification information that indicates the magnification applied in the affine transformation. After new MPR image data are generated by the MPR processor 433*a*, the conversion processor 434 executes the affine transformation on the new MPR image data, the affine transformation being magnification or reduction at the rate of magnification that is specified in the magnification information stored in the storage 440. Thereby, the affine transformation can be executed on the new MPR image data, with the same magnification that has been applied previously, so that MPR images in which the subject E is projected at the same magnification can be acquired automatically. This facilitates the smooth execution of the operation.

Furthermore, for a case where the storage 440 stores affine transformation information, the system is configured such that the conversion processor 434 executes the affine transformation based on the stored affine transformation information on the new MPR image data. Thereby, the new MPR image data are processed with the same affine transformation as has been applied previously, so that MPR images can be acquired automatically with the subject E being projected at the same position, in the same direction, and at the same magnification in the picture frame. This also facilitates the smooth execution of the work.

(Eighth Embodiment)

Figure 23:
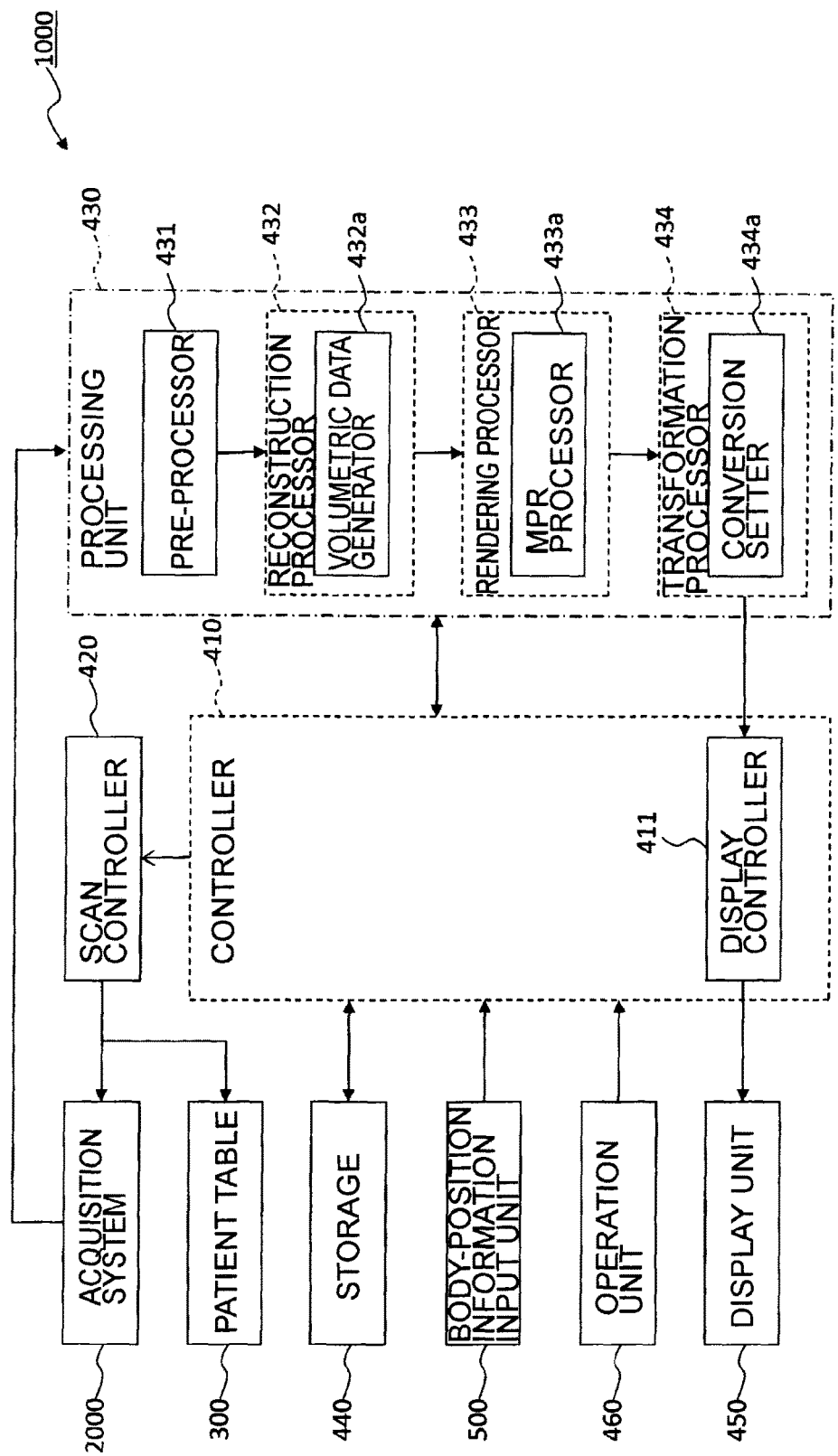
FIG. 23 is a block diagram showing the configuration of an X-ray CT system as an eighth embodiment.

This embodiment concerns an example in which MPR image data are processed with an affine transformation that corresponds to the body-position of the patient. FIG. 23 shows an exemplary configuration of the X-ray CT system as this embodiment. By the way, the entire configuration of this X-ray CT system is similar to that of the seventh embodiment, so reference should be appropriately made to FIG. 20. Accordingly, numerals applied in the seventh embodiment are also given here to the same parts in the configuration. Furthermore, the configuration and actions of the seventh embodiment can be combined arbitrarily with those of the eighth embodiment.

<System Configuration>

The X-ray CT system 1000 shown in FIG. 23 has a configuration similar to that of the seventh embodiment (refer to FIG. 21). As major differences from the configuration of the seventh embodiment, the eighth embodiment includes a body-position information input unit 500, and the conversion processor 434 is provided with a conversion setter 434*a*. These differences are mainly described in the following.

The body-position information input unit 500 is used for inputting body-position information that indicates the body position of the subject E placed on the patient table 300. The body-position information input unit 500 is a functional example of "input unit".

Body-position information may take an arbitrary in form in which the information can specify the body position of the subject E. For example, body-position information may be classification information that classifies the body position of the subject E, or it may be numerical information that expresses the body position in numerical values.

Examples of the classification information are information that indicates the mounted body direction of the subject E along the rostrocaudal direction (longitudinal direction of the top plate of the patient table 300) (first mounted body direction information), and information that indicates the mounted body direction of the subject E as direction of rotation around the rostrocaudal axis of the subject E as central axis (second mounted body direction information). The latter corresponds to the rotational position (angular degrees from a reference direction) around the body axis in a plane (axial section) that cuts the rostrocaudal axis at a right angle.

The classification of mounted body direction along the rostrocaudal axis (first mounted body direction information) includes, for example, two types of direction. One is that the head of the subject is positioned to the gantry apparatus 200, and the other is that the feet of the subject are positioned to the gantry apparatus 200. On the other hand, the classification of mounted body direction in the rotational direction around the rostrocaudal axis (second mounted body direction information) includes, four types of direction, for example, supine position, prone position, and lateral decubitus positions (rightward and leftward). When combined, the body positions of the subject E are classified in eight classes.

Now, an example of body-position information input unit 500 is described in connection with an operation of inputting classification information. At first, the display controller 411 presents a screen with selections of body position based on the classification information on the display unit 450. For example, each selection is presented as GUI items like an icon or a button that indicates a corresponding body position. Also, the selections can be shown in a pull-down menu format. The user specifies, with the operation unit 460, the selection that corresponds to the body position of the subject E from the presented selections. The control unit 410 recognizes the selected body position from the signal that is input by the operation unit 460 in response to the specification operation made by the user. As another example, hardware keys (buttons) can be provided in correspondence with the selections of body position. In these examples, the body-position information input unit 500 is configured to include the display unit 450 and the operation unit 460. By the way, in FIG. 23 the body-position information input unit 500 is depicted separately from the display unit 450 and the operation unit 460. However, in these examples, the body-position information input unit 500 is provided in a one-body with the operation unit 460 (and the display unit 450).

Instead of manually selecting the body position as in these examples, a detector may be provided to detect the body position of the subject E mounted on the patient table 300. The detector is configured to include, for example, a photographing unit that photographs the subject E placed on the patient table 300 and a specifier that specifies the body position by analyzing the photographed image. The photographing unit may be a digital camera or a digital video camera, or the acquisition system 2000 may play the role of the photographing unit. The specifier extracts a feature part of the subject E (i.e., a region that is depicted differently depending on how the body is positioned) in the photograph taken by the photographing unit, and the specifier specifies the body position on the basis of how the feature part is depicted. The specifier may execute this process by referring to a feature part that is observable on the body surface of the subject E (nose, navel, elbows, knees, toe-tips, etc.), or it may execute this process by referring to a feature part that is observed internally (i.e., the shape of an organ, placement of the organ, etc.). This process employs a well-known image-processing technique, for example, pattern matching.

Now, the above-mentioned numerical information is described. The numerical information is used, for example, to express information that indicates the mounted body direction of the subject E in axial section (second mounted body direction information). A predetermined reference direction can be set in axial section in advance. The reference direction is, for example, either in the direction of the x-coordinate axis or the y-coordinate axis (with the z-coordinate axis corresponding to the rostrocaudal axis) in the three-dimensional rectangular coordinate system (x, y, z) that is set to the three-dimensional region to be scanned (i.e., the region for which volumetric data are to be generated). In addition, the angular degree is defined in either clock-wise or counterclockwise direction from the reference direction. Moreover, the intervals (resolution) for the angular degree are defined arbitrarily.

Now, an example of body-position information input unit 500 is described in connection with an operation of inputting such numerical information. At first, the display controller 411 presents a screen for input of numerical information on the display unit 450. The user inputs numerical values that indicate the body position by using the operation unit 460. In addition, the system may be so configured to present a screen displaying a predetermined image like a schematically drawn subject and to acquire the numerical information that corresponds to the depicted rotational position the user has made by rotating the schematic image with the operation unit 460. In these examples, the body-position information input unit 500 is configured to include the display unit 450 and the operation unit 460. In addition, the system may be configured to include a detector and a specifier in the same way as in the case of the classification information, so that the numerical information can be input automatically.

Now, the conversion processor 434 of this embodiment is described. The conversion processor 434 is provided with a conversion setter 434a as previously described. The conversion setter 434a calculates an affine transformation for image inversion or rotational transfer in correspondence with the body-position information that has been input with the body-position information input unit 500. The following description details this process.

By the way, the MPR processor 433a generates MPR image data in the same way as in prior-art technologies, so that the direction of the subject E always agrees in images. For example, the image data for three-orthogonal-axis images are processed in the following conditions: axial image data are processed to show the abdomen of the subject to the upper side of the picture frame and the back of the subject to the lower side; sagittal image data are processed to show the front of the subject to the left side of the frame and the back to the right side; coronal image data are processed to show the front of the subject forward in the picture frame and the back of the subject farther away in the picture frame; and oblique image data are processed similarly such that the subject E is shown aligned in the direction in accordance with the same rules as in prior art.

The directions for MPR image data in accordance with the prior-art rules are hereinafter referred to as "standard directions". As a result, body positions can be related to standard directions. In other words, it is possible to preset a certain body position as standard (standard body position) before processing the data for both image inversion and rotational transfer. As a specific example, the mounted body direction in which the head of the subject is placed toward the gantry apparatus 200 is set as standard body position for the mounted body direction along the rostrocaudal axis, and supine position can be set as standard direction for the mounted body direction in axial section. If a body position that is not the standard body position is applied, then the need or no need of image inversion or rotational transfer or other considerations can be determined on the basis of the differences between the standard body position and the actual body position (described later).

Figure 24:
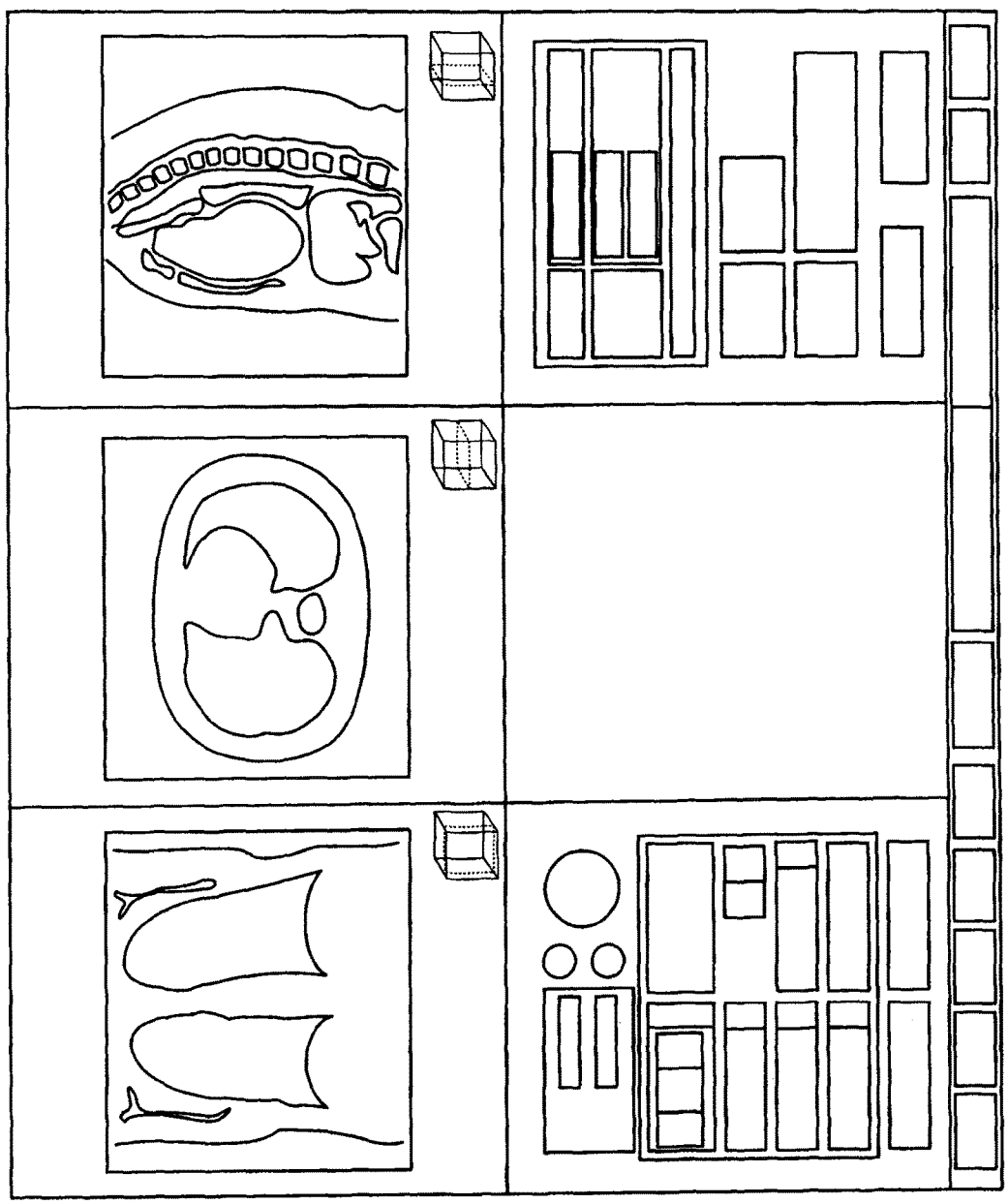
FIG. 24 is a schematic diagram for explaining actions taken by the X-ray CT system as an eighth embodiment.

FIG. 24 shows displaying conditions for three-orthogonal-axis images scanned with the standard body position. In the display screen shown, respectively, an axial image is shown in the middle on the upper side, a sagittal image is shown on the upper right side, and a coronal image is shown on the upper left side. Additionally, an arbitrary MPR image is presented in the middle on the lower side, and GUI items are provided on the lower right and left sides. The axial image in the standard body position is displayed with the abdomen being positioned to the upper side of the picture frame and the back of the subject being positioned to the lower side. The sagittal image in the standard body position is displayed with the front of the subject being positioned to the left side of the frame and the back of the subject to the right side. In other words, the sagittal image is displayed as an image in a sagittal section looked at from the left side of the subject. The coronal image in the standard body position is displayed with the front of the subject being positioned forward in the picture frame and the back of the subject rearward. In other words, the coronal image is displayed as an image in a coronal section looked at from the front of the subject.

The conversion setter 434a receives the body-position information, which has been input with the body-position information input unit 500, through the control unit 410. The conversion setter 434a determines the need or no need of image inversion and rotational transfer on the basis of the body position indicated in the body-position information and of the preset standard direction. If there is need for image inversion or rotational transfer, then the conversion setter 434a calculates an affine transformation by determining the contents of the image inversion or rotational transfer on the basis of the divergence of the direction of the body position indicated in the body-position information from the standard direction.

As an example in which the above-described classification information is used as body-position information, the X-ray CT system 1000 has, in memory beforehand, information (e.g., table information) that relates each classification of body position to conversion contents (contents of image inversion or rotational transfer) and to the types of sectional view (axial, sagittal, coronal, etc.). The table information is stored, for example, in the storage 440, and it is read out by the control unit 410 before the execution of the processing and is sent to the conversion setter 434a. Furthermore, if the conversion setter 434a is provided with a storage, then the table information is stored in this storage.

The conversion setter 434a specifies conversion contents in accordance with the body position indicated in the body-position information, which has been input with the body-position information input unit 500, and with the type of sectional view for the image to be displayed in (this is determined in advance) by referring to the table information. Furthermore, the conversion setter 434a sets an affine transformation on the basis of the specified conversion contents. Here, in a case where parallel displacement and magnification have already been set separately, the affine transformation is set up by taking into consideration of the values that have been assigned for these items of transformation.

The following is an example of table information. At first, about the body position in the rostrocaudal direction, if the standard direction is defined as the head of the subject being positioned to the gantry apparatus 200, then neither image inversion nor rotational transfer is executed for each type of sectional view. On the other hand, if the feet of the subject is positioned to the gantry apparatus 200, then image inversion is executed in the right and left direction of the picture frame for images in axial sectional view, but image inversion is executed in the up and down direction of the picture frame for images in sagittal sectional view or in coronal sectional view (or neither image inversion nor rotational transfer is executed).

Now, the description concerns the body position in the rotational direction in a plane (axial section) to which the rostrocaudal axis is normal. If the standard body position is supine position, then neither image inversion nor rotational transfer is executed for each type of sectional view. If the standard body position prone position, then image inversion is executed in the up and down direction of the picture frame for images in axial sectional view; image inversion is executed in the right and left direction of the picture frame for images in sagittal sectional view; and neither image inversion nor rotational transfer is executed for images in coronal sectional view. If the standard body position is lateral decubitus position (rightward or leftward), then rotational transfer of 90 degrees is executed depending on the direction of the subject for images in axial sectional view, and neither image inversion nor rotational transfer is executed for images in sagittal or coronal sectional view.

In the case where the body-position information (classification information) includes both the body position defined in the rostrocaudal direction and the body position defined in the rotational direction in axial section, the conversion setter 434a can set an affine transformation by combining two sets of conversion contents that correspond, respectively, to the body positions defined in these two directions. For example, if the subject is positioned with the feet to the gantry apparatus 200 and in prone position, then axial image data are inverted both in the right and left direction and in the up and down direction. Furthermore, the conversion contents that correspond to the body position defined in either of the directions may be prioritized in execution. For example, if the body position defined in the rotational direction in axial section is given priority, then in a case where the subject is positioned with the feet to the gantry apparatus 200 and in prone position, axial image data are inverted only in the up and down direction.

By the way, the above-mentioned table information is only an example. It is also possible to configure the table information to allow arbitrary modification to its table contents. In such a case, the user can arbitrarily specify which sectional views to be inverted and which sectional views not to (also in consideration of other conditions).

In the case where the body position defined in the rotational direction in axial section is expressed as numerical information, rotational transfer is executed on images in the direction of rotation in accordance with the angle defined between the direction indicated by the numerical information and the above-mentioned standard direction. The direction of rotation in this case can be determined in the same way as the case of lateral decubitus position in the classification information.

<Actions>

Figure 25:
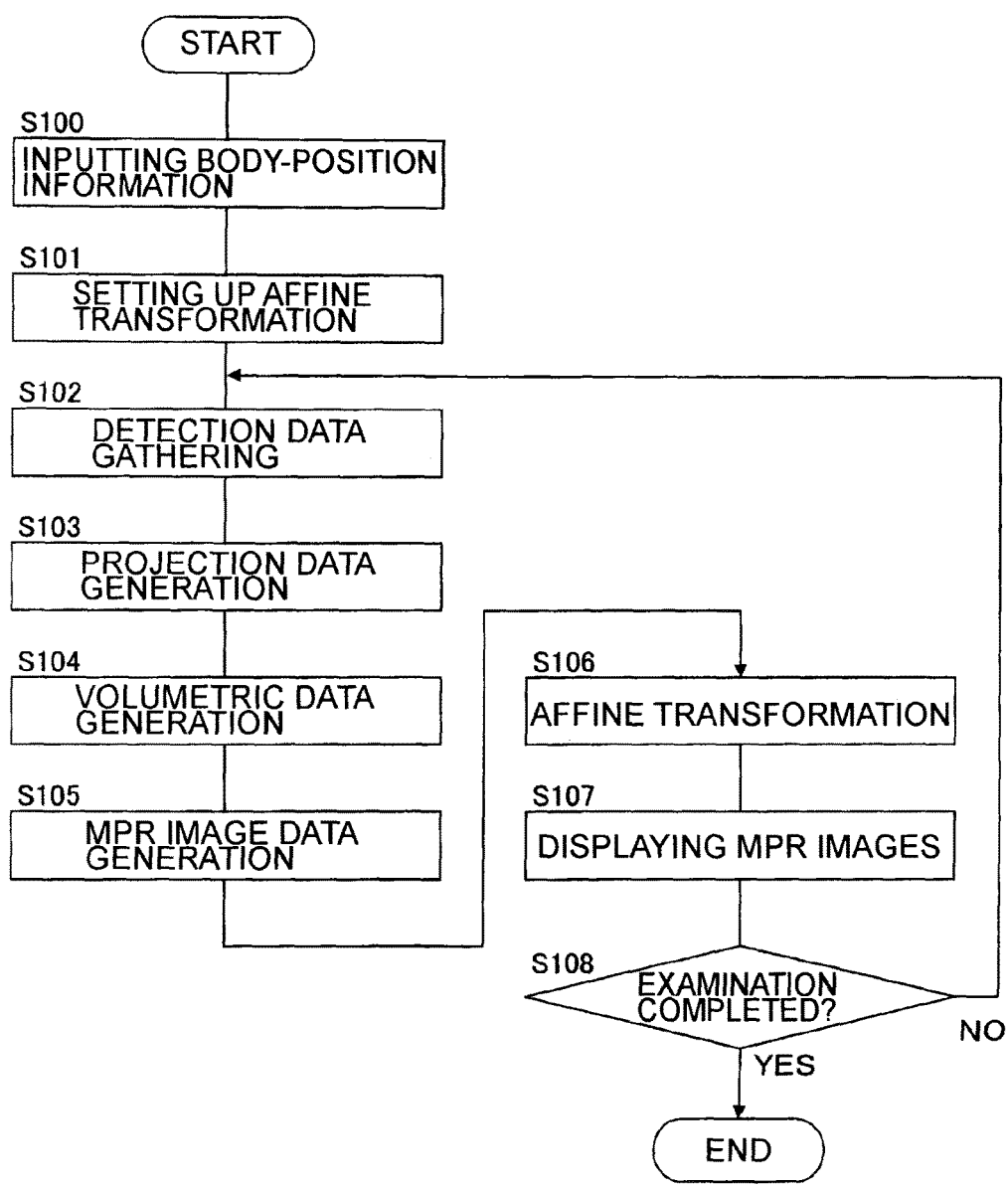
FIG. 25 is a flow chart showing exemplary actions taken by the X-ray CT system as an eighth embodiment.

Now, actions taken by the X-ray CT system 1000 as this embodiment are described. FIG. 25 shows exemplary actions taken by the X-ray CT system 1000.

(S100: Inputting Body-Position Information)

At first, a subject E is placed on the top plate of the patient table 300 and inserted into the through-opening of the gantry apparatus 200. The body-position information input unit 500 is used for inputting body-position information that indicates the body position of the subject E to the control unit 410. The control unit 410 sends the body-position information to the conversion setter 434a.

(S101: Setting Up Affine Transformation)

The conversion setter 434a calculates contents of image inversion or rotational transfer (conversion contents) for each type of sectional view on the basis of the body position indicated in the body-position information and the above-mentioned table information. Furthermore, the conversion setter 434a sets an affine transformation for each type of sectional view on the basis of the conversion contents (together with parallel displacement and/or magnification). By the way, this step of processing may be executed at an arbitrary timing before the execution of the affine transformation (i.e., anywhere from step 100 to step 106).

(S102: Detection Data Gathering)

When a predetermined scanning-initiation operation is made, the control unit 410 sends control signals to the scanning-control unit 420. The scanning-control unit 420, upon receiving the control signals, controls the high voltage generator 204, the gantry drive 205, and the collimator drive 207 to irradiate the subject E with X-rays for scanning. The X-ray detector 202 detects X-rays that have passed through the subject E. The data acquisition system 208 gathers detection data being generated by the X-ray detector 202 during the scanning. The data acquisition system 208 sends the gathered detection data to the preprocessor 431.

(S103: Projection Data Generation)

The preprocessor 431 executes a predetermined preprocessing on the detection data, which have been received from the data acquisition system 208, and the preprocessor generates projection data.

(S104: Volumetric Data Generation)

The reconstruction processor 432 executes reconstruction-processing on the projection data, which have been generated by the preprocessor 431, and the reconstruction processor generates plural sets of tomographic data. Furthermore, the volumetric data generator 432a generates volumetric data based on the sets of tomographic data.

(S105: MPR Image Data Generation)

The MPR processor 433a generates MPR image data on the basis of the volumetric data, which have been generated by the volumetric data generator 432a. Let's suppose that the MPR image data are image data for three-orthogonal-axis images. In other words, axial image data, sagittal image data, and coronal image data are generated from one set of volumetric data.

(S106: Affine Transformation)

The conversion processor 434 converts each set of the axial image data, the sagittal image data, and the coronal image data, which have been generated at step 105, by applying the affine transformation, which has been set up at step 101.

(S107: Displaying MPR Images)

The display controller 411 displays on the display unit 450, an axial image, a sagittal image and a coronal image based on the axial image data, the sagittal image data, and the coronal image data that have been processed with the affine transformation at step 106.

(S108: Examination Completed?)

If an instruction of examination completion is given at this stage (S108: YES), then the process of exemplary actions comes to an end. On the other hand, if the examination is continued (S108: NO), then steps 102-107 are repeated until an instruction of examination completion is given at step 108.

By the way, if the body position of the subject is changed at an arbitrary stage while steps 102-107 are being repeated, then a new affine transformation is set up on the basis of the new body position. Correspondingly, the directions of the MPR images displayed are changed.

<Display Examples>

Figure 26:
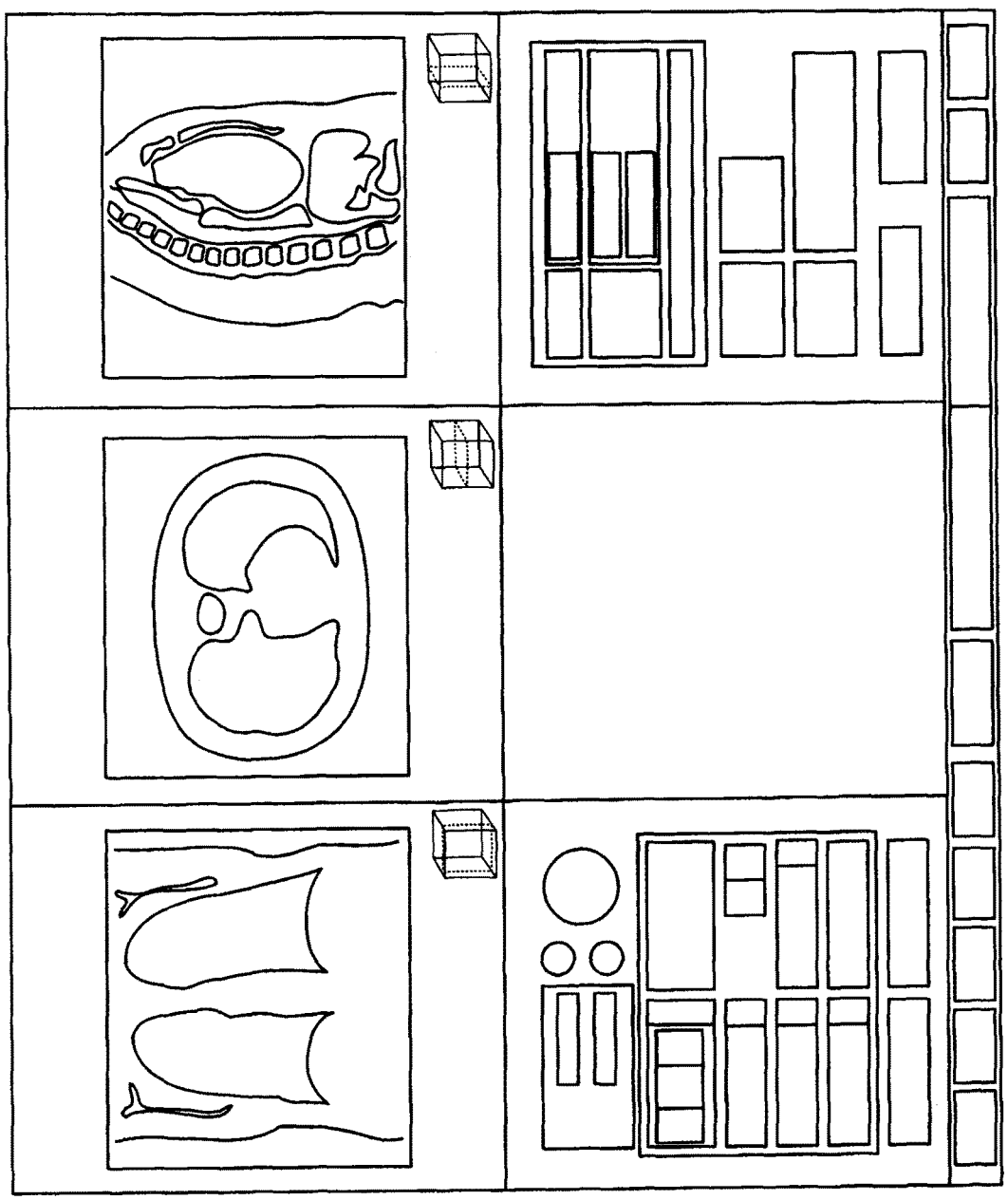
FIG. 26 is a schematic diagram for explaining actions taken by the X-ray CT system as an eighth embodiment.

The following is a description of conditions applied for displaying images by the above-mentioned actions. FIG. 26 shows examples of MPR image achieved with the body position being prone, for a case where the above-mentioned table information is applied. Here, comparison is made with the displaying conditions applied for the standard direction as shown in FIG. 24. The axial image shown in FIG. 26 (a view shown in the middle on the upper side) is an inversion of the axial image shown in FIG. 24 in the up and down direction. Also, the sagittal image shown in FIG. 26 (a view shown on the upper right side) is an inversion of the sagittal image shown in FIG. 24 in the right and left direction. As for the coronal images, both the views are in the same displaying conditions. These inversion conditions are applied to the case of prone position in accordance with the above-mentioned table information. According to this embodiment, the displaying directions of MPR images are changed in accordance with the body position in this way. In this embodiment, in the same way as the seventh embodiment, application of the same resolution for displaying the MPR images can prevent misunderstanding of the size of displayed objects.

<Operation and Effects>

Now, the operation and effects of the X-ray CT system 1000 as this embodiment are described.

The X-ray CT system 1000 comprises a patient table 300, an acquisition system 2000, a volumetric data generator 432a, an MPR processor 433a, a conversion processor 434, a display unit 450, and a display controller 411. The acquisition system 2000 scans the subject E mounted on the patient table 300 with X-rays and gathers data. The volumetric data generator 432a generates volumetric data based on the data gathered by the acquisition system 2000. The MPR processor 433a executes MPR processing on the volumetric data, which have been generated by the volumetric data generator 432a, and generates MPR image data that represent a view in a predetermined sectional plane. The conversion processor 434 executes an affine transformation on the MPR image data, which have been generated by the MPR processor 433a. The display controller 411 displays, on the display unit 450, an MPR image based on the MPR image data on which the affine transformation has been executed by the conversion processor 434.

According to such an X-ray CT system 1000, MPR image data are processed with affine transformation. This facilitates the smooth execution of the operation by automatically modifying the displaying conditions of MPR images depicting the subject E.

The X-ray CT system 1000 further comprises a body-position information input unit 500 (input unit), which is used for inputting body-position information that indicates the body position of the subject E placed on the patient table 300. Furthermore, the conversion processor 434 comprises a conversion setter 434a, which calculates an affine transformation that includes conversion contents (image inversion or rotational transfer) applied in accordance with the body-position information, which has been input with the body-position information input unit 500. The conversion processor 434 executes the affine transformation, which has been calculated by the conversion setter 434a, on MPR image data.

According to such an X-ray CT system 1000, the direction of the displayed MPR image is changed in accordance with the body position of the subject E. This facilitates the smooth execution of the work by automatically modifying the displaying conditions of the MPR images depicting the subject E. Furthermore, as the system eliminates the divergence that may otherwise result between the direction of the subject E being actually seen (i.e., the direction of the subject E in the real space) and the direction of the MPR image being displayed, it contributes greatly to the smooth execution of the work.

In addition, in the case where the MPR processor 433a generates plural sets of MPR image data that represent different sectional views on the basis of volumetric data, the conversion processor 434 can execute an affine transformation calculated by the conversion setter 434a selectively on plural sets of MPR image data generated by the MPR processor 433a. In the example presented above, axial image data, sagittal image data, and coronal image data are generated, and then the affine transformation is executed on a set of image data that is selected arbitrarily from these sets of image data.

Furthermore, a set of MPR image data can be arbitrarily specified for the affine transformation, and the specification operation is performed by using the operation unit 460. Moreover, the contents of the affine transformation to be executed on the MPR image data can be modified arbitrarily.

According to such an X-ray CT system 1000, it is possible to display an MPR image in such a direction as desired by the user because a desirable affine transformation can be applied to a desirable set of MPR image data.

The configuration and actions of the above X-ray CT system 1000 can be combined with the configuration and actions of the X-ray CT system 100 described previously as a seventh embodiment. For example, the X-ray CT system 1000 as this embodiment is configured such that the storage 440 stores magnification information that indicates a magnification to be applied in affine transformation. When new MPR image data are generated by the MPR processor 433a, the conversion setter 434a sets an affine transformation on the basis of the body position indicated in the body-position information, which has been input with the body-position information input unit 500, and of the magnification information stored in the storage 440. Then, the conversion processor 434 executes the affine transformation on the new MPR image data. As another combination example, the storage 440 stores affine transformation information that includes the above-mentioned magnification information. This affine transformation information may or may not include information for image inversion and rotational transfer. The conversion setter 434a sets a new affine transformation on the basis of the body position indicated in the body-position information, which has been input with the body-position information input unit 500, and of the affine transformation information stored in the storage 440. As for the parameters for image inversion or rotational transfer in this new affine transformation, for example, parameters included in the affine transformation information or parameters that correspond to the body position (i.e., parameters indicated in the above-mentioned table information) are applied for the standard body position, and parameters that correspond to the body position are applied for other cases. The conversion processor 434 executes this new affine transformation on the new MPR image data.

Some embodiments of the present invention have been described above; however, these embodiments are merely presented as examples without intending to limit the scope of the invention. These embodiments can be implemented in various other modes, and various omissions, replacements, and changes can be made without departing form the scope of the invention. These embodiments and their modifications are included not only within the scope and spirit of the invention but also in the invention set forth in the claims and any scope equivalent thereto.

DESCRIPTIONS OF NUMBERED PARTS

Numeral 1 designates an X-ray CT system;
10, gantry apparatus;
11, X-ray generator;
12, X-ray detector;
13, rotating body;
14, high voltage generator;
15, gantry drive;
16, collimator;
17, collimator drive;
18, data acquisition system;
30, patient table;
32, bed drive;
33, couch top;
34, pedestal;
40, console device;
41, scanning-control unit;
42, processing unit;
42a, preprocessor;
42b, reconstruction processor;
42c, moving-image creator;
42d, MPR processor;
43, display controller;
44, storage;
45, display unit;
46, input unit; and
47, control unit.

What is claimed is:

1. An X-ray CT system, comprising:
   processing circuitry configured to
      acquire data by scanning, with X-rays, a subject placed on a patient table;
      generate volumetric data based on the acquired data;
      generate sectional images corresponding to an axial section, a sagittal section, and a coronal section based on the volumetric data so that the subject in each image is oriented in a preset standard direction regardless of an actual body position of the subject,
      acquire body-position information corresponding to the actual body position of the subject,
      determine, for each of the sectional images, necessity of a coordinate transformation, based on the actual body position and the preset standard direction in each of the sectional images,
      apply the coordinate transformation to at least one of the sectional images for which it is determined that the coordinate transformation is necessary, so that the subject in the at least one of the sectional images is oriented in a direction corresponding to the actual body position, and
      cause a display to display the sectional ages including at least one image to which the coordinate transformation is applied,
   wherein the processing circuitry is further configured to specify a particular sectional image from among the sectional images according to an input from an operator, and determine the necessity of the coordinate transformation for only the specified image.

2. The X-ray CT system according to claim 1,
   further comprising a memory that stores coordinate transformation information that describes the determined coordinate transformation and includes magnification information; and
   the processing circuitry is further configured to execute, on sectional image data, the determined coordinate transformation based on the stored coordinate transformation information.

3. The X-ray CT system according to claim 1, wherein the processing circuitry is further configured to:
   generate plural sets of sectional image data that represent views in different sectional planes, based on the volumetric data; and
   execute the determined coordinate transformation selectively on the plural sets of sectional image data.

4. The X-ray CT system according to claim 3, further comprising an operation interface configured to receive selection of one or more of the plural sets of sectional image data, wherein the processing circuitry is further configured to execute the determined coordinate transformation on each of the selected sets of sectional image data.

5. The X-ray CT system according to claim 3, wherein the plural sets of sectional image data are one or more sets of axial image data, sagittal image data, and coronal image data.

6. The X-ray CT system according to claim 1, wherein the body-position information comprises at least one of first mounted body direction information, which indicates a longitudinal position along a rostrocaudal axis of the subject, and second mounted body direction information, which indicates a rotational direction around the rostrocaudal axis as a center of rotation.

7. The X-ray CT system according to claim 1, wherein the processing circuitry is further configured to display, on the display at a same resolution, first sectional image based on first sectional image data that has not been processed with the determined coordinate transformation and second sectional image based on second sectional image data that has been processed with the determined coordinate transformation.

8. The X-ray CT system according to claim 1, wherein the processing circuitry is further configured to apply the determined coordinate transformation to second sectional image data when a second sectional image based on the second sectional image data is displayed with first sectional image.

9. The X-ray CT system of claim 1, wherein the processing circuitry is further configured to determine the coordinate transformation by analyzing the particular sectional image, including specifying at least one of a position and direction of the subject, and calculating at least one of an amount of parallel displacement and an amount of rotational transfer.

10. The X-ray CT system of claim 1, wherein the processing circuitry is further configured to apply the determined coordinate transformation to second sectional image data to magnify or reduce the second sectional image data automatically at a rate of magnification specified by the stored magnification information, which is arbitrarily set.

11. The X-ray CT system of claim 1, wherein the coordinate transformation includes an affine transformation.

12. An X-ray CT system, comprising:
processing circuitry configured to
acquire data by scanning, with X-rays, a subject placed on a patient table;
generate volumetric data based on the acquired data;
generate sectional images corresponding to an axial section, a sagittal section, and a coronal section based on the volumetric data so that the subject in each image is oriented in a preset standard direction regardless of an actual body position of the subject,
acquire body position information corresponding to the actual body-position of the subject,
determine, for each of the sectional images, necessity of a coordinate transformation, based on the actual body position and the preset standard direction in each of the sectional image,
apply the coordinate transformation to at least one of the sectional images for which it is determined that the coordinate transformation is necessary, so that the subject in the at least one of the sectional images is oriented in a direction corresponding to the actual body position, and
cause a display to display the sectional images including at least one image to which the coordinate transformation is applied,
wherein the body-position information corresponds to one of eight classes that are combinations of two directions along a body direction of the subject and four directions along rotational direction around the body direction.

* * * * *